(12) United States Patent
Machiya et al.

(10) Patent No.: US 6,875,768 B1
(45) Date of Patent: Apr. 5, 2005

(54) PHTHALAMIDE DERIVATIVES, INTERMEDIATES IN THE PRODUCTION THEREOF, AND AGRICULTURAL/HORTICULTURAL INSECTICIDES AND METHOD FOR USING THE SAME

(75) Inventors: Kouzou Machiya, Osaka (JP); Kazuyoshi Endoh, Kawachinagano (JP); Takashi Furuya, Izumisano (JP); Hayami Nakao, Kawachinagano (JP); Makoto Gotoh, Sakai (JP); Eiji Kohno, Bisai (JP); Masanori Tohnishi, Sakai (JP); Kazuyuki Sakata, Kawachinagano (JP); Masayuki Morimoto, Kawachinagano (JP); Akira Seo, Hashimoto (JP)

(73) Assignee: Nihon Nohyako Co., Ltd., Tokyo (JP)

( * ) Notice: Subject to any disclaimer, the term of this patent is extended or adjusted under 35 U.S.C. 154(b) by 250 days.

(21) Appl. No.: 10/018,464

(22) PCT Filed: Jul. 4, 2000

(86) PCT No.: PCT/JP00/04444

§ 371 (c)(1),
(2), (4) Date: Apr. 24, 2002

(87) PCT Pub. No.: WO01/02354

PCT Pub. Date: Jan. 11, 2001

(30) Foreign Application Priority Data

Jul. 5, 1999 (JP) .......................................... 11-190746
Mar. 22, 2000 (JP) ....................................... 2000-080991

(51) Int. Cl.$^7$ .................... C07D 401/12; C07D 401/14; A01N 43/40

(52) U.S. Cl. ....................... 514/256; 514/313; 514/332; 514/333; 514/337; 514/338; 514/339; 514/349; 514/352; 546/162; 546/255; 546/256; 546/269.1; 546/269.7; 546/271.4; 546/272.4; 546/275.4; 546/280.4; 546/283.4; 546/309; 544/333

(58) Field of Search .................. 546/162, 255, 546/256, 269.1, 269.7, 271.4, 272.4, 275.4, 280.4, 283.4, 309; 544/333; 514/256, 313, 332, 333, 337, 338, 339, 349, 352

(56) References Cited

U.S. PATENT DOCUMENTS 4,173,639 A 11/1979 Lilly
4,840,662 A 6/1989 Ciba-Geigy

FOREIGN PATENT DOCUMENTS

| EP | 919542 | 6/1999 |
|---|---|---|
| EP | 1006107 | 6/2000 |
| HU | 158697 | 10/1970 |
| HU | 179545 | 11/1982 |
| HU | 31706 | 5/1984 |
| HU | 206584 | 12/1992 |
| JP | 59-163353 | 9/1984 |
| JP | 5-345779 | 12/1993 |
| JP | 7-196628 | 8/1995 |
| WO | WO 00/26202 | 5/2000 |

OTHER PUBLICATIONS

Popova et al. "Synthesis and characterization of some new fluorinated pyrimidine derivatives" J. Fluorine Chem. (1999) vol. 96 No. 1 pp. 51–56.

Gallucci et al. "Addition of functional amines to perfluoro-akylethynes", J. Fluorine Chem. (1980) vol. 15, No. 4 pp. 333–7.

Bognitskii et al. "Reactions of 2,4,6-tris(perfluoro alkyl)-1,3,5-triazines with ammonia and dimethyamine", Zh. Vses. Khim. O–va, (1979), vol. 24, No. 1, p. 101.

*Primary Examiner*—Mark L. Berch
*Assistant Examiner*—Kahsay Habte
(74) *Attorney, Agent, or Firm*—Paul E. White, Jr.; Manelli Denison & Selter PLLC

(57) ABSTRACT

Heterocyclic amine derivatives represented by general formula (I):

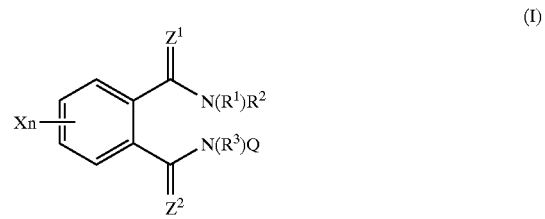

wherein $R^1$, $R^2$ and $R^3$ represent each H, optionally halogenated $C_{3-6}$ cycloalkyl, etc.; Q represents an optionally substituted heterocycle containing O, S or N; X represents halogeno, cyano, halo($C_{1-6}$)alkyl, etc.; n is from 1 to 4; and $Z^1$ and $Z^2$ represent each O or S; and intermediates thereof represented by the following general formula (IV'): Q'—$NH_2$ wherein Q' represents a definite heterocycle selected from among those represented by Q. Agricultural/horticultural insecticides having a remarkable effect of controlling pest insects of crops such as rice, fruit trees and vegetables, as well as various agricultural, forestry, horticultural and stored grain pest insects.

6 Claims, No Drawings

PHTHALAMIDE DERIVATIVES, INTERMEDIATES IN THE PRODUCTION THEREOF, AND AGRICULTURAL/HORTICULTURAL INSECTICIDES AND METHOD FOR USING THE SAME

This application is the national phase of international application PCT/JP00/04444 filed 4 Jul. 2000 which designated the U.S.

BACKGROUND OF THE INVENTION

1. Field of the Invention

The present invention relates to phthalamide derivatives, production intermediates thereof, agrohorticultural insecticides containing said compounds as active ingredient, and a method for using said insecticides.

2. Related Art

A part of the phthalamide derivatives of the present invention are disclosed in JP-A-59-163353, JP-A-61-180753, Journal of Chemical Society (J.C.S.), Perkin I, 1338–1350 (1978), etc. Neither description nor suggestion about usefulness of these compounds as an agrihorticultural insecticide, however, is made therein at all. On the other hand, the heterocyclic amine derivatives represented by the general formula (IV), which serve as intermediate compounds for production of said phthalamide derivatives, are novel compounds not found in literature.

SUMMARY OF THE INVENTION

The present inventors have conducted repeated studies on the development of a novel agrohorticultural agent. As a result, it has been found that the phthalamide derivatives of the present invention represented by the general formula (I) which are novel compounds and some known compounds disclosed in prior art are useful as novel agrohorticultural insecticides. It has further been found that the heterocyclic amine derivatives represented by the formulas (IV') which are novel compounds not found in literature are useful as intermediates for production of a variety of physiologically active compounds usable as medical drugs, pesticides, etc. Based on these findings, the present invention has been accomplished.

DETAILED DESCRIPTION OF THE INVENTION

The present invention relates to phthalamide derivatives represented by the general formula (I):

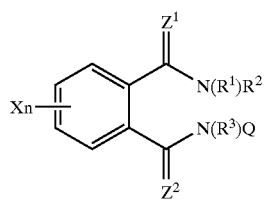

(I)

{wherein $R^1$, $R^2$ and $R^3_1$ which may be same or different, represent hydrogen atom, $C_3$–$C_6$ cycloalkyl group, halo $C_3$–$C_6$ cycloalkyl group or —$A^1$—$(G)_r$ (in this formula, $A^1$ represents $C_1$–$C_8$ alkylene group, $C_3$–$C_6$ alkenylene group or $C_3$–$C_6$ alkynylene group; G, which may be same or different, represents hydrogen atom, halogen atom, cyano group, nitro group, halo $C_1$–$C_6$ alkyl group, $C_3$–$C_6$ cycloalkyl group, halo $C_3$–$C_6$ cycloalkyl group, $C_1$–$C_6$ alkoxycarbonyl group, di($C_1$–$C_6$)alkoxyphosphoryl group in which the ($C_1$–$C_6$) alkoxy groups may be same or different, di($C_1$–$C_6$) alkoxythiophosphoryl group in which the ($C_1$–$C_6$)alkoxy groups may be same or different, diphenylphosphino group, diphenylphosphono group, phenyl group, substituted phenyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkyl-sulfinyl group, $C_1$–$C_6$ alkylsulfonyl group and halo $C_1$–$C_6$ alkylsulfonyl group, heterocyclic group (as used herein, the term "heterocyclic group" means pyridyl group, pyridine-N-oxide group, pyrimidinyl group, furyl group, tetrahydrofuryl group, thienyl group, tetrahydrothienyl group, tetrahydropyranyl group, oxazolyl group, isoxazolyl group, oxadiazolyl group, thiazolyl group, isothiazolyl group, thiadiazolyl group, imidazolyl group, triazolyl group or pyrazolyl group), substituted heterocyclic group (the term heterocyclic group is as defined above) having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, —$Z^3$—$R^4$ (in this formula, $Z^3$ represents —O—, —S—, —SO—, —$SO_2$—, —$N(R^5)$— (in this formula, $R^5$ represents hydrogen atom, $C_1$–$C_6$ alkylcarbonyl group, halo $C_1$–$C_6$ alkylcarbonyl group, $C_1$–$C_6$ alkoxycarbonyl group, phenylcarbonyl group, substituted phenylcarbonyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, phenyl $C_1$–$C_4$ alkoxycarbonyl group, substituted phenyl $C_1$–$C_4$ alkoxycarbonyl group having, on the ring thereof, at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, $C_1$–$C_6$ alkylsulfonyl group or halo $C_1$–$C_6$ alkylsulfonyl group), —C(=O)— or —C(=$NOR^6$)— (in this formula, $R^6$ represents hydrogen atom, $C_1$–$C_6$ alkyl group, halo $C_1$–$C_6$ alkyl group, $C_3$–$C_6$ alkenyl group, halo $C_3$–$C_6$ alkenyl group, $C_3$–$C_6$ alkynyl group, $C_3$–$C_6$ cycloalkyl group, phenyl $C_1$–$C_4$ alkyl group, or substituted phenyl $C_1$–$C_4$ alkyl group having, on the ring thereof, at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group), and $R^4$ represents hydrogen atom, $C_1$–$C_6$ alkyl group, halo $C_1$–$C_6$ alkyl group, $C_3$–$C_6$ alkenyl group, halo $C_3$–$C_6$ alkenyl group, $C_3$–$C_6$ alkynyl group, halo $C_3$–$C_6$ alkynyl group, $C_3$–$C_6$ cycloalkyl group, halo $C_3$–$C_6$ cycloalkyl group, $C_1$–$C_6$ alkoxy $C_1$–$C_6$ alkyl group, $C_1$–$C_6$ alkylthio $C_1$–$C_6$ alkyl group, formyl group, $C_1$–$C_6$ alkylcarbonyl group, halo $C_1$–$C_6$ alkylcarbonyl group, $C_1$–$C_6$ alkoxycarbonyl group, mono ($C_1$–$C_6$)alkylaminocarbonyl group, di($C_1$–$C_6$)

alkylaminocarbonyl group in which the $(C_1-C_6)$alkyl groups may be same or different, mono$(C_1-C_6)$ alkylaminothiocarbonyl group, di$(C_1-C_6)$ alkylaminothiocarbonyl group in which the $(C_1-C_6)$alkyl groups may be same or different, di$(C_1-C_6)$ alkoxyphosphoryl group in which the $(C_1-C_6)$alkoxy groups may be same or different, di$(C_1-C_6)$ alkoxythiophosphoryl group in which the $(C_1-C_6)$alkoxy groups may be same or different, phenyl group, substituted phenyl group having at least one, same or different substituents selected from the group consisting of halogen atom, $C_1-C_6$ alkyl group, halo $C_1-C_6$ alkyl group, $C_1-C_6$ alkoxy group, halo $C_1-C_6$ alkoxy group, $C_1-C_6$ alkylthio group, halo $C_1-C_6$ alkylthio group, $C_1-C_6$ alkylsulfinyl group, halo $C_1-C_6$ alkylsulfinyl group, $C_1-C_6$ alkylsulfonyl group and halo $C_1-C_6$alkylsulfonyl group, phenyl $C_1-C_4$ alkyl group, substituted phenyl $(C_1-C_4)$ alkyl group having, on the ring thereof, at least one, same or different substituents selected from the group consisting of halogen atom, $C_1-C_6$ alkyl group, halo $C_1-C_6$ alkyl group, $C_1-C_6$ alkoxy group, halo $C_1-C_6$ alkoxy group, $C_1-C_6$ alkylthio group, halo $C_1-C_6$ alkylthio group, $C_1-C_6$ alkylsulfinyl group, halo $C_1-C_6$ alkylsulfinyl group, $C_1-C_6$ alkylsulfonyl group and halo $C_1-C_6$ alkylsulfonyl group, heterocyclic group (the term heterocyclic group is as defined above), or substituted heterocyclic group (the term heterocyclic group is as defined above) having at least one, same or different substituents selected from the group consisting of halogen atom, $C_1-C_6$ alkyl group, halo $C_1-C_6$ alkyl group, $C_1-C_6$ alkoxy group, halo $C_1-C_6$ alkoxy group, $C_1-C_6$ alkylthio group, halo $C_1-C_6$ alkylthio group, $C_1-C_6$ alkylsulfinyl group, halo $C_1-C_6$ alkylsulfinyl group, $C_1-C_6$ alkylsulfonyl group and halo $C_1-C_6$ alkylsulfonyl group); and r represents an integer of 1 to 4); further, $R^1$ and $R^2$ may be taken conjointly to form 4- to 7-membered rings which may be intercepted by 1 to 3, same or different oxygen atom, sulfur atom or nitrogen atom;

X, which may be same or different, represents halogen atom, cyano group, nitro group, $C_3-C_6$ cycloalkyl group, halo $C_3-C_6$ cycloalkyl group, phenyl group, substituted phenyl group having at least one, same or different substituents selected from the group consisting of halogen atom, $C_1-C_6$ alkyl group, halo $C_1-C_6$ alkyl group, $C_1-C_6$ alkoxy group, halo $C_1-C_6$ alkoxy group, $C_1-C_6$ alkylthio group, halo $C_1-C_6$ alkylthio group, $C_1-C_6$ alkylsulfinyl group, halo $C_1-C_6$ alkylsulfinyl group, $C_1-C_6$ alkylsulfonyl group and halo $C_1-C_6$ alkylsulfonyl group, heterocyclic group (the term heterocyclic group is as defined above), substituted heterocyclic group (the term heterocyclic group is as defined above) having at least one, same or different substituents selected from the group consisting of halogen atom, $C_1-C_6$ alkyl group, halo $C_1-C_6$ alkyl group, $C_1-C_6$ alkoxy group, halo $C_1-C_6$ alkoxy group, $C_1-C_6$ alkylthio group, halo $C_1-C_6$ alkylthio group, $C_1-C_6$ alkylsulfinyl group, halo $C_1-C_6$ alkylsulfinyl group, $C_1-C_6$ alkylsulfonyl group and halo $C_1-C_6$ alkylsulfonyl group, or $—A^2—R^7$ [in this formula, $A^2$ represents $—O—$, $—S—$, $—SO—$, $—SO_2—$, $—NR^6—$ (in this formula $R^8$ represents hydrogen atom, $C_1-C_6$ alkylcarbonyl group, halo $C_1-C_6$ alkylcarbonyl group, $C_1-C_6$ alkoxycarbonyl group, phenylcarbonyl group, substituted phenylcarbonyl group having at least one, same or different substituents selected from the group consisting of halogen atom, $C_1-C_6$ alkyl group, halo $C_1-C_6$ alkyl group, $C_1-C_6$ alkoxy group, halo $C_1-C_6$ alkoxy group, $C_1-C_6$ alkylthio group, halo $C_1-C_6$ alkylthio group, $C_1-C_6$ alkylsulfinyl group, halo $C_1-C_6$ alkylsulfinyl group, $C_1-C_6$ alkylsulfonyl group and halo $C_1-C_6$ alkylsulfonyl group, phenyl $C_1-C_4$ alkoxycarbonyl group or substituted phenyl $C_1-C_4$ alkoxycarbonyl group having, on the ring thereof, at least one, same or different substituents selected from the group consisting of halogen atom, $C_1-C_6$ alkyl group, halo $C_1-C_6$ alkyl group, $C_1-C_6$ alkoxy group, halo $C_1-C_6$ alkoxy group, $C_1-C_6$ alkylthio group, halo $C_1-C_6$ alkylthio group, $C_1-C_6$ alkylsulfinyl group, halo $C_1-C_6$ alkylsulfinyl group, $C_1-C_6$ alkylsulfonyl group and halo $C_1-C_6$ alkylsulfonyl group), $—C(=O)—$, $—C(=NOR^6)—$ (in this formula, $R^6$ is as defined above), $C_1-C_6$ alkylene group, halo $C_1-C_6$ alkylene group, $C_2-C_6$ alkenylene group, halo $C_2-C_6$ alkenylene group, $C_{2-C6}$ alkynylene group or halo $C_3-C_6$ alkynylene group; and (1) in cases where $A^2$ represents $—O—$, $—S—$, $—SO—$, $—SO_2—$ or $—NR^3—$ (in this formula, $R^8$ is as defined above), $R^7$ represents hydrogen atom, halo $C_3-C_6$ cycloalkyl group, halo $C_3-C_6$ cycloalkenyl group, phenyl group, substituted phenyl group having at least one, same or different substituents selected from the group consisting of halogen atom, $C_1-C_6$ alkyl group, halo $C_1-C_6$ alkyl group, $C_1-C_6$ alkoxy group, halo $C_1-C_6$ alkoxy group, $C_1-C_6$ alkylthio group, halo $C_1-C_6$ alkylthio group, $C_1-C_6$ alkylsulfinyl group, halo $C_1-C_6$ alkylsulfinyl group, $C_1-C_6$ alkylsulfonyl group and halo $C_1-C_6$ alkylsulfonyl group, heterocyclic group (the term heterocyclic group is as defined above), substituted heterocyclic group (the term heterocyclic group is as defined above) having at least one, same or different substituents selected from the group consisting of halogen atom, $C_1-C_6$ alkyl group, halo $C_1-C_6$ alkyl group, $C_1-C_6$ alkoxy group, halo $C_1-C_6$ alkoxy group, $C_1-C_6$ alkylthio group, halo $C_1-C_6$ alkylthio group, $C_1-C_6$ alkylsulfinyl group, halo $C_1-C_6$ alkylsulfinyl group, $C_1-C_6$ alkylsulfonyl group and halo $C_1-C_6$ alkylsulfonyl group, or $—A^3—R^9$ (in this formula, $A^3$ represents $C_1-C_6$ alkylene group, halo $C_1-C_6$ alkylene group, $C_3-C_6$ alkenylene group, halo $C_3-C_6$ alkenylene group, $C_3-C_6$ alkynylene group or halo $C_3-C_6$ alkynylene group; and $R^9$ represents hydrogen atom, halogen atom, $C_3-C_6$ cycloalkyl group, halo $C_3-C_6$ cycloalkyl group, $C_1-C_6$ alkoxycarbonyl group, phenyl group, substituted phenyl group having at least one, same or different substituents selected from the group consisting of halogen atom, $C_1-C_6$ alkyl group, halo $C_1-C_6$ alkyl group, $C_1-C_6$ alkoxy group, halo $C_1-C_6$ alkoxy group, $C_1-C_6$ alkylthio group, halo $C_1-C_6$ alkylthio group, $C_1-C_6$ alkylsulfinyl group, halo $C_1-C_6$ alkylsulfinyl group, $C_1-C_6$ alkylsulfonyl group and halo $C_1-C_6$ alkylsulfonyl group, or $—A^4—R^{10}$ (in this formula, $A^4$ represents $—O—$, $—S—$, $—SO—$, $—SO_2—$ or $—C(=O)—$; and $R^{10}$ represents $C_1-C_6$ alkyl group, halo $C_1-C_6$ alkyl group, $C_3-C_6$ alkenyl group, halo $C_3-C_6$ alkenyl group, $C_3-C_6$ cycloalkyl group, halo $C_3-C_6$ cycloalkyl group, phenyl group, substituted phenyl group having at least one, same or different substituents selected from the group consisting of halogen atom, $C_1-C_6$ alkyl group, halo $C_1-C_6$ alkyl group, $C_1-C_6$ alkoxy group, halo $C_1-C_6$ alkoxy group, $C_1-C_6$ alkylthio group, halo $C_1-C_6$ alkylthio group, $C_1-C_6$ alkylsulfinyl group, halo $C_1-C_6$ alkylsulfinyl group, $C_1-C_6$ alkylsulfonyl group and halo $C_1-C_6$ alkylsulfonyl group, heterocyclic group (the term heterocyclic group is as defined above), or substituted heterocyclic group (the term heterocyclic group is as defined above) having at least one, same or different substituents selected from the group consisting of halogen atom, $C_1-C_6$ alkyl group, halo $C_1-C_6$ alkyl group, $C_1-C_6$ alkoxy group, halo $C_1-C_6$ alkoxy group, $C_1-C_6$ alkylthio group, halo $C_1-C_6$ alkylthio group, $C_1-C_6$ alkylsulfinyl group, halo $C_1-C_6$ alkylsulfinyl group, $C_1-C_6$ alkylsulfonyl group and halo $C_1-C_6$ alkylsulfonyl group));

(2) in cases where $A^2$ represents —C(=O)— or —C(=NOR$^6$)— (in this formula, $R^6$ is as defined above), $R^7$ represents hydrogen atom, $C_1$–$C_6$ alkyl group, halo $C_1$–$C_6$ alkyl group, $C_2$–$C_6$ alkenyl group, halo $C_2$–$C_6$ alkenyl group, $C_3$–$C_6$ cycloalkyl group, halo $C_3$–$C_6$ cycloalkyl group, $C_1$–$C_6$ alkoxy group, $C_1$–$C_6$ alkylthio group, mono($C_1$–$C_6$)alkylamino group, di($C_1$–$C_6$) alkylamino group in which the ($C_1$–$C_6$)alkyl groups may be same or different, phenyl group, substituted phenyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, phenylamino group, substituted phenylamino group having, on the ring thereof, at least one, same or different substituents selected from the group consisting of halogen atom, $C_1$–$C_6$ alkyl group, halo $C_1C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group (the term heterocyclic group is as defined above), or substituted heterocyclic.group (the term heterocyclic group is as defined above) having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group; and (3) in cases where $A^2$ represents $C_1$–$C_6$ alkylene group, halo $C_1$–$C_6$ alkylene group, $C_2$–$C_6$ alkenylene group, halo $C_2$–$C_6$ alkenylene group, $C_2$–$C_6$ alkynylene group or halo $C_3$–$C_6$ alkynylene group, $R^7$ represents hydrogen atom, halogen atom, $C_3$–$C_6$ cycloalkyl group, halo $C_3$–$C_6$ cycloalkyl group, $C_1$–$C_6$ alkoxycarbonyl group, tri ($C_1$–$C_6$) alkylsilyl group in which the ($C_1$–$C_6$)alkyl groups may be same or different, phenyl group, substituted phenyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group (the term heterocyclic group is as defined above), substituted heterocyclic group (the term heterocyclic group is as defined above) having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, or —A$^5$—R$^{11}$ (in this formula, $A^5$ represents —O—, —S—, —SO— or —SO$_2$—; and $R^{11}$ represents $C_3$–$C_6$ cycloalkyl group, halo $C_3$–$C_6$ cycloalkyl group, phenyl group, substituted phenyl group having at lest one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group (the term heterocyclic group is as defined above), substituted heterocyclic group (the term heterocyclic group is as defined above) having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, or —A$^6$—R$^{12}$ (in this formula, $A^6$ represents $C_1$–$C_6$ alkylene group, halo $C_1$–$C_6$ alkylene group, $C_2$–$C_6$ alkenylene group, halo $C_2$–$C_6$ alkenylene group, $C_2$–$C_6$ alkynylene group or halo $C_3$–$C_6$ alkynylene group; and $R^{12}$ represents hydrogen atom, halogen atom, $C_3$–$C_6$ cycloalkyl group, halo $C_1$–$C_6$ cycloalkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, phenyl group, substituted phenyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, phenoxy group, substituted phenoxy group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, phenylthio group, substituted phenylthio group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group (the term heterocyclic group is as defined above), or substituted heterocyclic group (the term heterocyclic group is as defined above) having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group))];

n represents an integer of 0 to 4; further, X may be taken conjointly with the adjacent carbon atom on the phenyl ring to form a fused ring (as used herein, the term fused ring means naphthalene, tetrahydronaphthalene, indene, indane, quinoline, quinazoline, chroman, isochroman, indole, indoline, benzodioxane, benzodioxole, benzofuran, dihydrobenzofuran, benzothiophene, dihydrobenzothiophene, benzoxazole, benzothiazole, benzimidazole or indazole), and said fused ring may have at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, phenyl group, substituted phenyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group (the term heterocyclic group is as defined above), and substituted heterocyclic group (the term heterocyclic group is as defined above) having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group;

Q represents an N-, S- or O-containing, optionally substituted, heterocyclic group or fused heterocyclic group, selected from the group consisting of the following formulas Q1 to Q60;

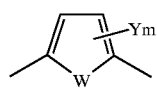
Q1

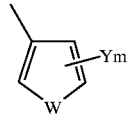
Q2

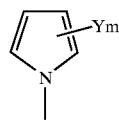
Q3

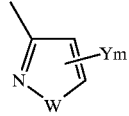
Q4

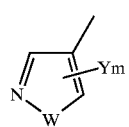
Q5

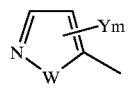
Q6

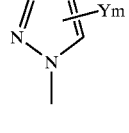
Q7

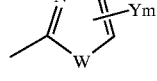
Q8

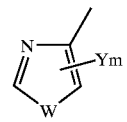
Q9

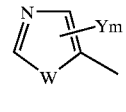
Q10

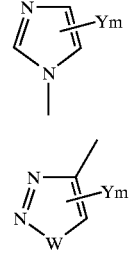
Q11

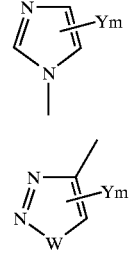
Q12

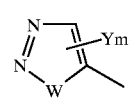
Q13

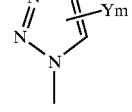
Q14

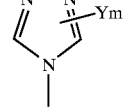
Q15

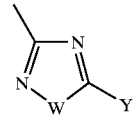
Q16

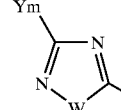
Q17

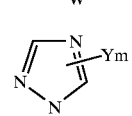
Q18

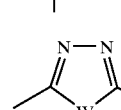
Q19

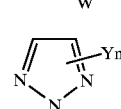
Q20

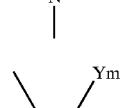
Q21

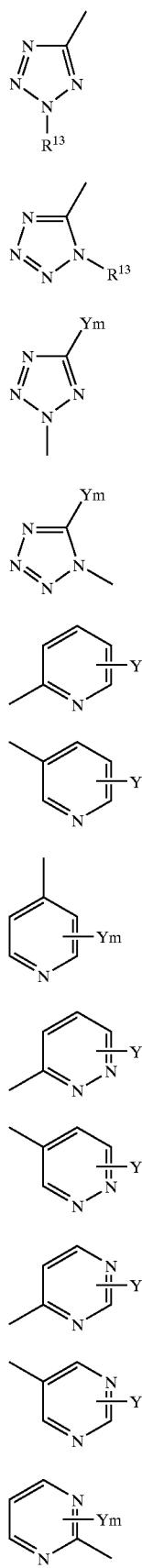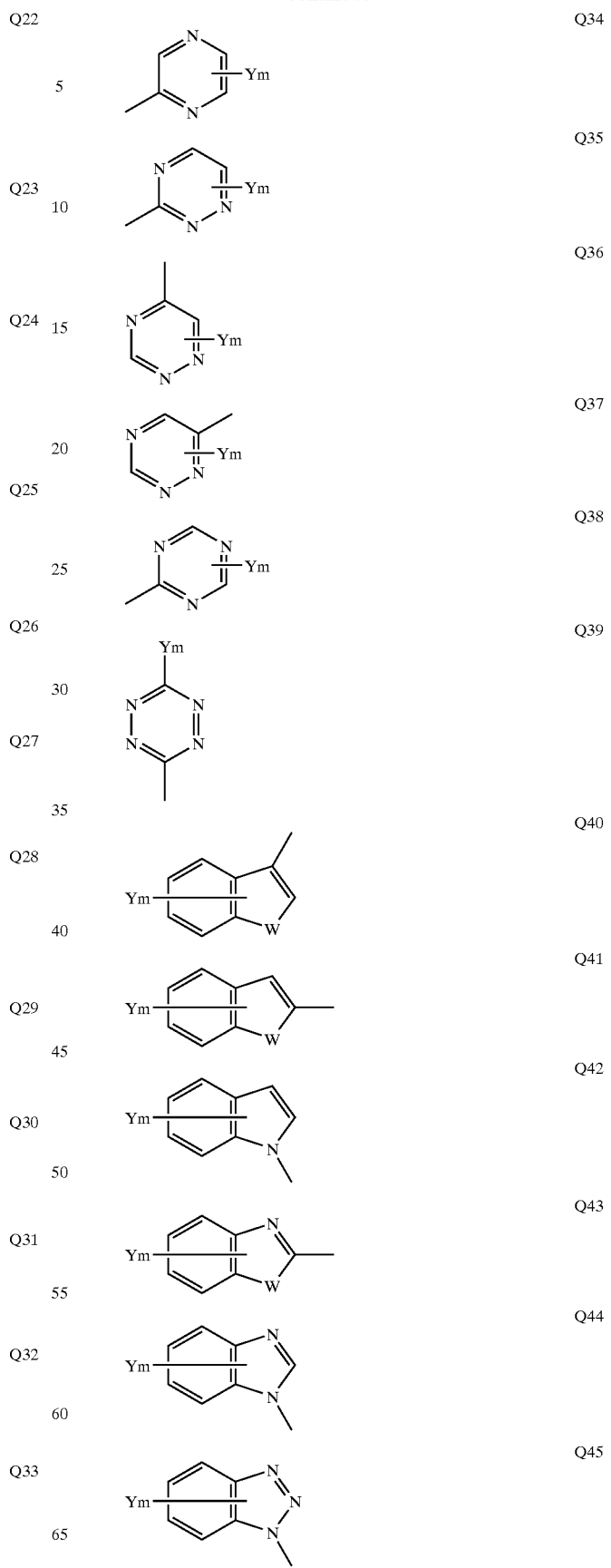

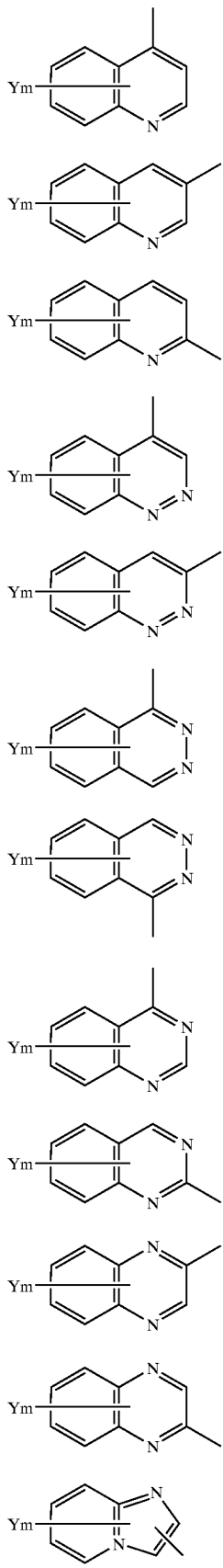
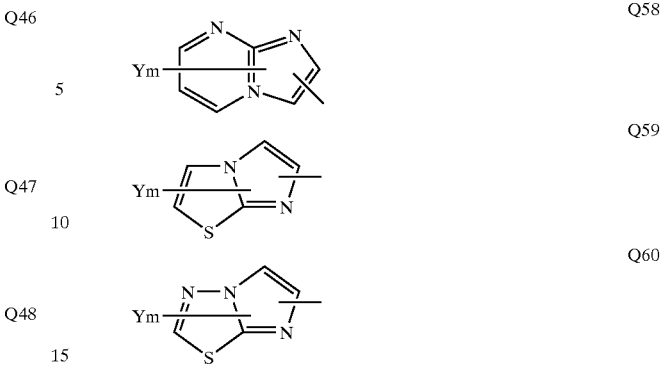

(in these formulas, Y, which may be same or different, represents halogen atom, cyano group, nitro group, halo $C_3$–$C_6$ cycloalkyl group, phenyl group, substituted phenyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group (the term heterocyclic group is as defined above), substituted heterocyclic group (the term heterocyclic group is as defined above) having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, or —$A^2$—$R^7$ (in this formula, $A^2$ and $R^7$ are as defined above); m represents an integer of 0 to 6; $R^{13}$ in the formula Q22 and Q23 represents hydrogen atom, $C_1$–$C_6$ alkyl group, halo $C_1$–$C_6$ alkyl group, $C_3$–$C_6$ alkenyl group, halo $C_3$–$C_6$ alkenyl group, $C_3$–$C_6$ alkynyl group, halo $C_3$–$C_6$ alkynyl group, $C_3$–$C_6$ cycloalkyl group, halo $C_3$–$C_6$ cycloalkyl group, $C_1$–$C_6$ alkoxy $C_1$–$C_6$ alkyl group, halo $C_1$–$C_6$ alkoxy $C_1$–$C_6$ alkyl group, $C_1$–$C_6$ alkylthio $C_1$–$C_6$ alkyl group, halo $C_1$–$C_6$ alkylthio $C_1$–$C_6$ alkyl group, $C_1$–$C_6$ alkylsulfinyl $C_1$–$C_6$ alkyl group, halo $C_1$–$C_6$ alkylsulfinyl $C_1$–$C_6$ alkyl group, $C_1$–$C_6$ alkylsulfonyl $C_1$–$C_6$ alkyl group, halo $C_1$–$C_6$ alkylsulfonyl $C_1$–$C_6$ alkyl group, $C_1$–$C_6$ alkylsulfonyl group, halo $C_1$–$C_6$ alkylsulfonyl group, $C_1$–$C_6$ alkylcarbonyl group, halo $C_1$–$C_6$ alkylcarbonyl group, $C_1$–$C_6$ alkoxycarbonyl group, phenyl group, substituted phenyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, phenyl $C_1$–$C_4$ alkyl group, substituted phenyl $C_1$–$C_4$ alkyl group having, on the ring thereof, at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, phenylcarbonyl group, or substituted phenylcarbonyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group);

alternatively, Y may be taken conjointly with adjacent carbon atom on the ring to form a fused ring (the fused ring is as defined above), and said fused ring may have at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, phenyl group, substituted phenyl group having at least one, same or different substituents selected from the group consisting of halogen atom, $C_1$–$C_5$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group (the term heterocyclic group is as defined above), and substituted heterocyclic group (the term heterocyclic group is as defined above) having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group;

W represents O, S or N—$R^{13}$ (in this formula, $R^{13}$ is as defined above); and $Z^1$ and $Z^2$ represent oxygen atom or sulfur atom;

provided that when X, $R^1$ and $R^3$ simultaneously represent hydrogen atom, $Z^1$ and $Z^2$ simultaneously represent oxygen atom, Q represents Q27, and Y is a chlorine atom of 2-position, then $R^2$ is not 1,2,2-trimethylpropyl group};

and to an agrohorticultural insecticide, and a method for using the same.

The present invention further relates to a heterocyclic amine derivative represented by the following general formula (IV'):

Q'—NH$_2$ (IV')

wherein:

(1) in cases where Q' represents one of the following formulas Q26, Q28–Q31 and Q33–Q39,

Q26

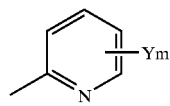
Q28

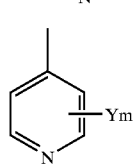
Q29

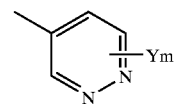
Q30

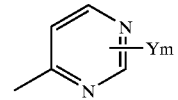
Q31

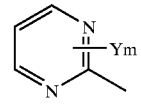
Q33

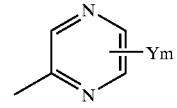
Q34

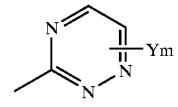
Q35

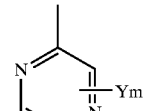
Q36

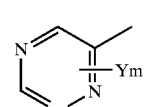
Q37

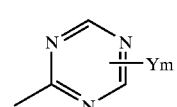
Q38

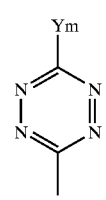
Q39

Y, which may be same or different, represents hydrogen atom, halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group or halo $C_1$–$C_6$ alkylsulfonyl group, m represents an integer of 1 to 4, and at least one of Y, of which total number is m, is perfluoro $C_2$–$C_6$ alkyl group; and (2) in a case where Q' represents Q27 and Q32:

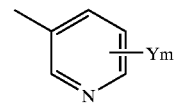
Q27

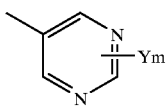

Q32

Y, which may be same or different, represents hydrogen atom, halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group or halo $C_1$–$C_6$ alkylsulfonyl group, m represents an integer of 1 to 4, and at least one of Y, of which total number is m, is perfluoro $C_2$–$C_6$ alkyl group, halo $C_1$–$C_6$ alkoxy group, halo $C_1$–$C_6$ alkoxy halo $C_1$–$C_6$ alkoxy group or halo $C_1$–$C_6$ alkylthio group.

The heterocyclic amine derivative of the formula (IV') is useful for an intermediate compound for production of the phthalamide derivatives of the formula (I).

In the definition of the general formula (I) of the phthalamide derivative of the present invention, "halogen atom" means chlorine atom, bromine atom, iodine atom or fluorine atom; "$C_1$–$C_6$ alkyl" means a straight or branched chain alkyl group having 1 to 6 carbon atoms such as methyl, ethyl, n-propyl, i-propyl, n-butyl, i-butyl, s-butyl, t-butyl, n-pentyl, n-hexyl or the like; "halo $C_1$–$C_6$ alkyl" means a straight or branched chain alkyl group having 1 to 6 carbon atoms substituted with at least one, same or different halogen atoms; and "$C_1$–$C_8$ alkylene" means a straight or branched chain alkylene group having 1 to 8 carbon atoms such as methylene, ethylene, propylene, trimethylene, dimethylmethylene, tetramethylene, isobutylene, dimethylethylene, octamethylene or the like.

As examples of the "$R^1$ and $R^2$ taken conjointly to form a 4- to 7-membered ring which may be intercepted by 1 to 3, same or different oxygen atom, sulfur atom or nitrogen atom", there can be referred to azetidine ring, pyrrolidine ring, pyrroline ring, piperidine ring, imidazolidine ring, imidazoline ring, oxazolidine ring, thiazolidine ring, isoxazolidine ring, isothiazolidine ring, tetrahydropyridine ring, piperazine ring, morpholine ring, thiomorpholine ring, dioxazine ring, dithiazine ring, and the like.

Some of the phthalamide derivatives of the present invention represented by the general formula (I) have an asymmetric carbon atom or asymmetric center in the structural formulas thereof, and there can exist two optical isomers sometimes. The present invention includes all such optical isomers and their mixtures at arbitrary proportions, and sometimes includes salts and hydrates thereof.

In the phthalamide derivatives of the present invention represented by the general formula (I), preferable substituents are as follows. Thus, the phthalamide derivative of the invention is preferably a phthalamide derivative of the general formula (I) wherein $R^1$, $R^2$ and $R^3$ may be same or different and represent hydrogen atom or —$A^1$—G (in this formula, $A^1$ represents $C_1$–$C_8$ alkylene group and G represents hydrogen atom, $C_1$–$C_6$ alkylthio group, $C_1$–$C_6$ alkylsulfinyl group, $C_1$–$C_6$ alkylsulfonyl group, $C_1$–$C_6$ alkylcarbonylamino group or $C_1$–$C_6$ alkoxycarbonylamino group); X may be same or different and represents halogen atom, nitro group, halo $C_1$–$C_6$ alkyl group, halo $C_1$–$C_6$ alkoxy group or halo $C_1$–$C_6$ alkylthio group; n represents an integer of 0 to 4; Q represents Q27; Y may be same or different and represents halogen atom, $C_1$–$C_6$ alkyl group, $C_1$–$C_6$ alkoxy group, halo $C_1$–$C_6$ alkoxy group, halo $C_1$–$C_6$ alkoxy halo $C_1$–$C_6$ alkoxy group, $C_1$–$C_6$ alkylthio group, halo $C_1$–$C_6$ alkylthio group, halo $C_1$–$C_6$ alkoxy halo $C_1$–$C_6$ alkylthio group, halo $C_1$–$C_6$ alkylsulfinyl group or halo $C_1$–$C_6$ alkylsulfonyl group; m represents an integer of 0 to 4; $Z^1$ and $Z^2$ represent oxygen atom. Further preferably, the phthalamide derivative of the invention is a phthalamide derivative of general formula (I) wherein $R^1$ and $R^3$ represent hydrogen atom; $R^2$ represents $C_1$–$C_6$ alkylthio $C_1$–$C_6$ alkyl group; X represents halogen atom; n represents an integer of 1 to 2; Q represents Q27; Y may be same or different and represents halogen atom, $C_1$–$C_6$ alkyl group, halo $C_1$–$C_6$ alkyl group, $C_1$–$C_6$ alkoxy group or halo $C_1$–$C_6$ alkoxy group; m represents an integer of 1 to 2; and $Z^1$ and $Z^2$ represent oxygen atom.

The compounds of the present invention can be produced according to Schemes 1 and 2 mentioned below, though the compounds of the present invention can also be produced by the process described in JP-A-11-240857.

Production Process 1

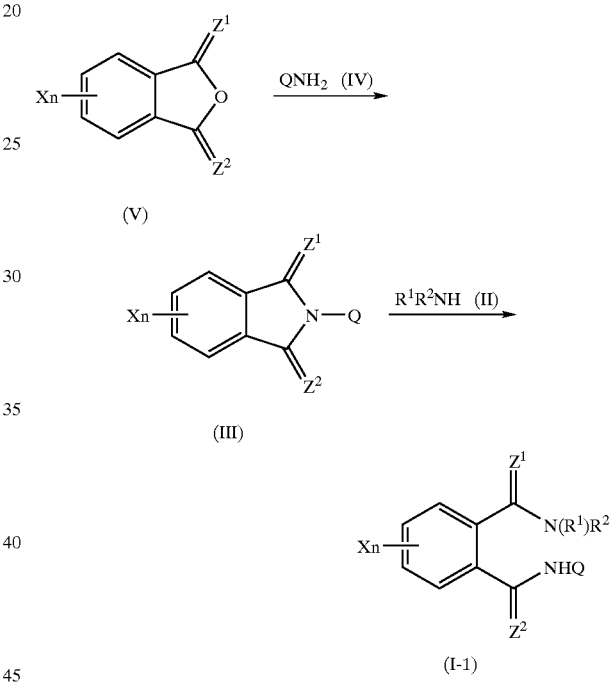

wherein $R^1$, $R^2$, $Z^1$, $Z^2$, X, Q and n are as defined above.

A phthalic anhydride derivative represented by general formula (V) is reacted with a heterocyclic amine derivative represented by general formula (IV) in the presence of an inert solvent to form a phthalimide derivative represented by general formula (III). After isolating or without isolating the phthalimide derivative (III), (III) is reacted with an amine represented by general formula (II). Thus, a phthalamide derivative represented by general formula (I-1) can be produced.

(1) General formula (V)→General formula (III)

As the inert solvent used in this reaction, any solvent may be used so far as it does not disturb the progress of the reaction markedly. Examples of the inert solvent which can be used include aromatic hydrocarbons such as benzene, toluene, xylene and the like, halogenated hydrocarbons such as methylene chloride, chloroform, carbon tetrachloride and the like, chlorinated aromatic hydrocarbons such as chlorobenzene, dichlorobenzene and the like, acyclic and cyclic ethers such as diethyl ether, dioxane, tetrahydrofuran and the like, esters such as ethyl acetate and the like, amides such as dimethylformamide, dimethylacetamide and the like, acids such as acetic acid and the like, dimethyl sulfoxide, 1,3-dimethyl-2-imidazolidinone, etc. These inert solvents may be used either singly or in combination or two or more solvents.

Since this reaction is an equimolar reaction, the reactants may be used in equimolar amounts. If desired, however, any one reactant may be also used in excess. According to the need, this reaction may be carried out under a dehydrating condition.

The reaction may be carried out in a temperature range from room temperature to the refluxing temperature of the used inert solvent. Although the reaction time may vary depending on scale and temperature of the reaction, it may be appropriately selected in a range from several minutes to 48 hours.

After completion of the reaction, the objective product is isolated from the reaction system in the conventional manner and purified by the method of recrystallization, column chromatography, etc. according to the need, whereby the objective product can be obtained. It is also possible to feed the objective product to the subsequent step without isolation.

The phthalic anhydride derivative represented by the general formula (V) can be produced according to the method described in J. Org. Chem., 52, 129 (1987); J. Am. Chem. Soc., 51, 1865 (1929); ibid., 63, 1542 (1941), etc. The heterocyclic amine derivative represented by the general formula (IV) can be produced according to the method described in J. Org. Chem., 18, 138 (1953); J. Org. Chem., 28, 1877 (1963); Chem. Ber., 89, 2742 (1956); Proc. Indian Acad. Sci., 37A, 758 (1953); J. Heterocycl. Chem., 17, 143 (1980); JP-A-62-96479; JP-A-10-340345; JP-A-11-302233; etc.

(2) General formula (III)→General formula (I-1)

As the inert solvents usable in this reaction, the same ones as those usable in the above-mentioned reaction (1) can be referred to. Since this reaction is an equimolar reaction, the reactants may be used in equimolar amounts, though the amine of the general formula (II) may be used in excess, if desired. The reaction can be carried out in a temperature range falling in a range from room temperature to the refluxing temperature of the used inert solvent. Although the reaction time varies depending on scale and temperature of the reaction, it may be selected appropriately in a range from several minutes to 48 hours.

After completion of the reaction, the objective product is isolated from the reaction system containing the product in a conventional manner. According to the need, the product is purified by the method of recrystallization, column chromatography, etc., whereby the objective product can be obtained.

Production Process 2

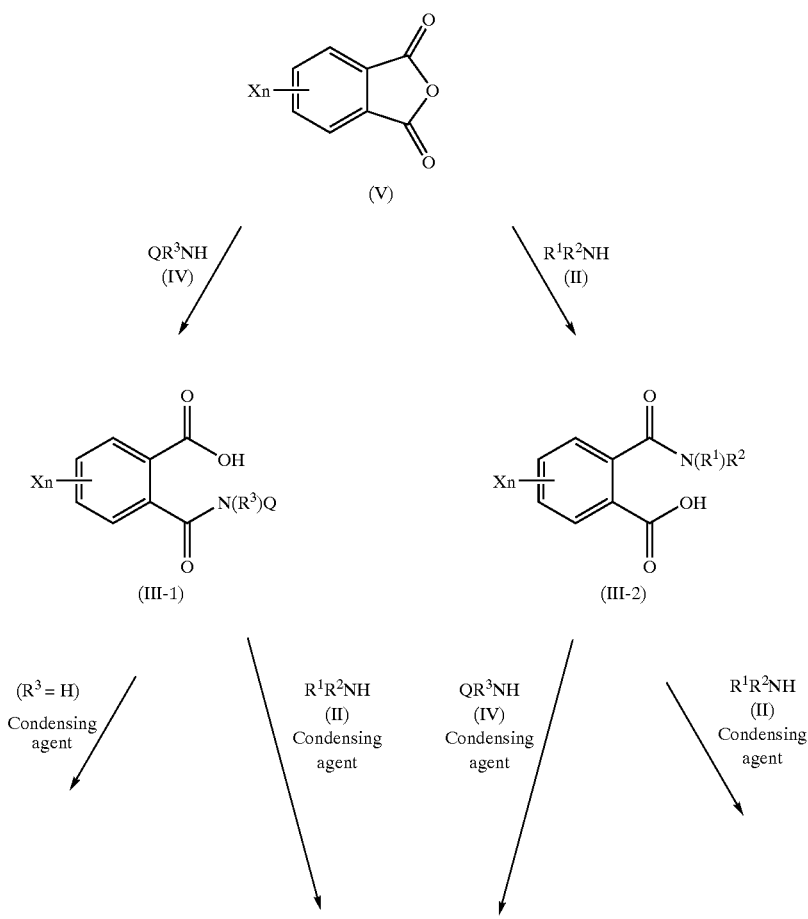

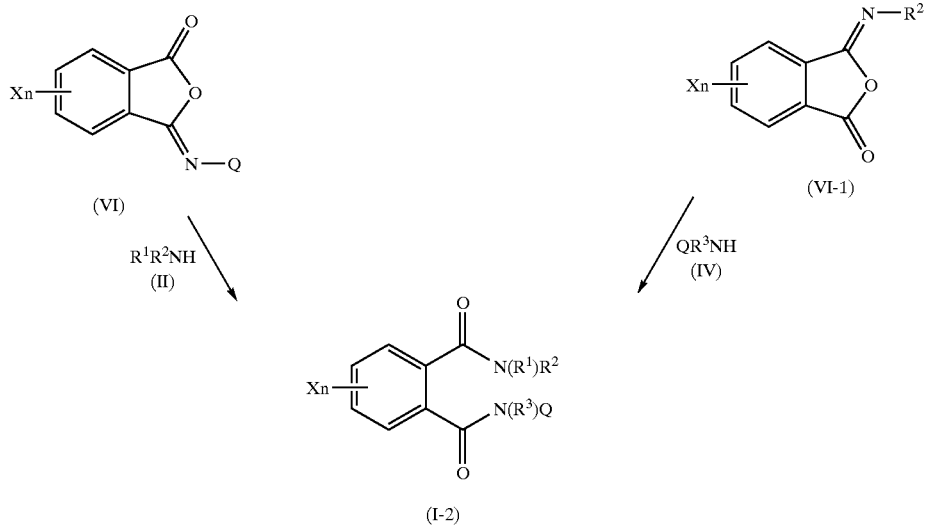

wherein $R^1$, $R^2$, $R^3$, X, Q and n are as defined above.

A phthalic anhydride derivative represented by general formula (V) is reacted with an amine represented by general formula (II) in the presence of an inert solvent to form a phthalamide represented by general formula (III-2). In cases where $R^1$ in (III-2) is hydrogen atom, the phthalamide (III-2) is isolated or not isolated and then subjected to a condensation reaction in the presence of a condensing agent to form a compound represented by general formula (VI-1), and after isolating or without isolating (VI-1), the compound (VI-1) is reacted with a heterocyclic amine derivative represented by general formula (IV) in the presence of an inert solvent. In cases where $R^1$ in phthalamide (III-2) is not hydrogen atom, (III-2) having been isolated or not isolated is subjected to a condensation reaction with a heterocyclic amine represented by general formula (IV) in the presence of a condensing agent. In these manners, a phthalamide derivative represented by general formula (I-2) can be produced.

Alternatively, a phthalic anhydride derivative represented by general formula (V) is reacted with a heterocyclic amine derivative represented by general formula (IV) in the presence of an inert solvent to form a phthalamide represented by general formula (III-1). In cases where $R^3$ in (III-1) is hydrogen atom, the phthalamide (III-1) is isolated or not isolated, and then subjected to a condensation reaction in the presence of a condensing agent to form a compound represented by general formula (VI), and after isolating or not isolating the compound (VI), (VI) is subjected to a reaction with an amine represented by general formula (II) in the presence of an inert solvent. In cases where $R^3$ in phthalamide (III-1) is not hydrogen atom, the phthalamide (III-1) having been isolated or not isolated is subjected to a condensation reaction with an amine represented by general formula (II) in the presence of a condensing agent. In these manners, a phthalamide derivative represented by general formula (I-2) can be obtained.

(1) General formula (V)→General formula (III-2) or General formula (VI-1)—General formula (I-2)

This reaction can be practiced in the same manner as in Production process 1-(2), whereby the objective product can be obtained.

(2) General formula (III-1)→General formula (VI) or General formula (III-2)→General formula (VI-1)

This reaction can be practiced according to the description of J. Med. Chem., 10, 982 (1967), whereby the objective product can be obtained.

(3) General formula (VI)→General formula (I-2) or General formula (V)→General formula (III-2)

This reaction can be practiced in the same manner as in Production process 1-(2), whereby the objective product can be obtained.

(4) General formula (III-1) or General formula (III-2) →General formula (I-2)

This reaction can be practiced by reacting a phthalamide derivative represented by general formula (III-1) or (III-2) with an amine represented by general formula (II) or (IV) in the presence of a condensing agent and an inert solvent. This reaction may be practiced in the presence of a base, if necessary.

As examples of the inert solvent used in this reaction, tetrahydrofuran, diethyl ether, dioxane, chloroform, methylene chloride and the like can be referred to. As examples of the condensing agent used in this reaction, those used in the conventional production of amides can be used, of which examples include Mukaiyama reagent (2-chloro-N-methylpyridinium iodide), DCC (1,3-dicyclohexylcarbodiimide), CDI (carbonyl diimidazole), DEPC (diethyl cyanophosphonate), etc. The amount of the condensing agent may be appropriately selected in a range from an equimolar amount to an excessive molar amount based on the phthalamide derivative represented by general formula (III-1) or (III-2).

As examples of the base which can be used in this reaction, organic bases such as triethylamine, pyridine and the like, and inorganic bases such as potassium carbonate and the like can be referred to. The amount of the base may be appropriately selected in the range from an equimolar amount to an excessive molar amount based on the phthalamide derivative represented by general formula (III-1) or (III-2).

The reaction can be carried out in a temperature range from 0° C. to the boiling point of the used inert solvent. Although the reaction time may vary depending on scale and temperature of the reaction, it is in the range of from several minutes to 48 hours.

After completion of the reaction, the objective product is isolated from the reaction system by the conventional method, and the product may be purified by recrystallization, column chromatography, etc. according to the need, whereby the objective product can be obtained.

Next, typical examples of the heterocyclic amine derivative represented by general formula (IV') are listed in Table 1, and typical examples of the phthalamide derivative represented by general formula (I) are listed in Tables 2 to 12.

The present invention is by no means limited by the compounds shown herein. In the tables shown below, "Me" means methyl, "Et" means ethyl, "Pr" means propyl, "Bu" means butyl, "Ac" means acetyl, "Ph" means phenyl, the expression "c-" means an alicyclic hydrocarbon, "mp" means melting point, and "nD" means refractive index.

General Formula (IV')

$$Q'-NH_2 \qquad (IV')$$

TABLE 1

Q': Q26, Q27, Q32, Q34

| No. | Q' | Ym | mp (° C.) or $^1$H-NMR [δ (ppm/CDCl$_3$)] |
|---|---|---|---|
| IV'-1 | Q26 | 3-Me-5-C$_2$F$_5$ | 2.17(s. 3H), 4.82(br. 2H), 7.42(d. 1H), 8.16(s. 1H). |
| IV'-2 | Q26 | 3-Me-5-n-C$_3$F$_7$ | 2.18(s. 3H), 4.94(br. 2H), 7.41(d. 1H), 8.19(s. 1H). |
| IV'-3 | Q26 | 3-Me-5-i-C$_3$F$_7$ | 2.18(s. 3H), 4.80(br. 2H), 7.42(d. 1H), 8.15(s. 1H). |
| IV'-4 | Q27 | 2-n-C$_3$F$_7$ | 4.08(br. 2H), 7.04(dd. 1H), 7.43(d. 1H), 8.16(d. 1H). |
| IV'-5 | Q27 | 6-Cl-2-n-C$_3$F$_7$ | 4.65(br. 2H), 7.17(d. 1H), 7.57(d. 1H). |
| IV'-6 | Q27 | 2-C$_2$F$_5$ | 3.72(br. 2H), 7.04(dd. 1H), 7.46(d. 1H), 8.16(d. 1H). |
| IV'-7 | Q27 | 2-i-C$_3$F$_7$ | 4.12(br. 2H), 7.06(dd. 1H), 7.44(dd. 1H), 8.13(d. 1H). |
| IV'-8 | Q27 | 4-Me-2-i-C$_3$F$_7$ | 2.22(s. 3H), 4.12(br. 2H), 7.34(d. 1H), 8.07(s. 1H). |
| IV'-9 | Q27 | 4-Me-6-i-C$_3$F$_7$ | 2.21(s. 3H), 4.26(br. 2H), 7.09(dd. 1H), 7.98(d. 1H). |
| IV'-10 | Q27 | 6-Me-2-i-C$_3$F$_7$ | 2.42(s. 3H), 4.12(br. 2H), 6.98(d. 1H), 7.31(dd. 1H). |
| IV'-11 | Q27 | 6-Cl-2-i-C$_3$F$_7$ | 4.40(br. 2H), 7.12(d. 1H), 7.41(dd. 1H). |
| IV'-12 | Q27 | 6-F-2-i-C$_3$F$_7$ | |
| IV'-13 | Q27 | 6-i-C$_3$F$_7$ | 4.28(br. 2H), 7.04(dd. 1H), 7.18(m. 1H), 8.07(d. 1H). |
| IV'-14 | Q27 | 4,6-Cl$_2$-2-i-C$_3$F$_7$ | 4.80(br. 2H), 7.53(d. 1H). |
| IV'-15 | Q27 | 6-MeO-2-i-C$_3$F$_7$ | 3.96(s. 3H.), 4.03(br. 2H), 6.91(d. 1H), 7.10(dd. 1H). |
| IV'-16 | Q27 | 6-MeS-2-i-C$_3$F$_7$ | 2.58(s. 3H), 4.00(br. 2H), 6.91(d. 1H), 7.22(dd. 1H). |
| IV'-17 | Q27 | 6-MeSO-2-i-C$_3$F$_7$ | |
| IV'-18 | Q27 | 6-MeSO$_2$-2-I-C$_3$F$_7$ | |
| IV'-19 | Q32 | 4-Me-2-i-C$_3$F$_7$ | 2.46(s. 3H), 3.94(br. 2H), 8.15(s. 1H). |
| IV'-20 | Q32 | 4-Me-6-i-C$_3$F$_7$ | 2.49(s. 3H), 4.35(br. 2H), 8.55(s. 1H). |
| IV'-21 | Q34 | 5-i-C$_3$F$_7$ | 5.0(br. 2H), 8.01(s. 1H), 8.31(s. 1H). |
| IV'-22 | Q27 | 2-OCF$_2$CHF$_2$ | 3.43(br. 2H), 6.13(tt. 1H), 6.88(d. 1H), 7.08(dd. 1H), 7.74(d. 1H). |
| IV'-23 | Q27 | 2-OCHF$_2$ | 3.60(br. 2H), 6.72(d. 1H), 7.07(dd. 1H), 7.26(dd. 1H), 7.63(d. 1H). |
| IV'-24 | Q27 | 6-Me-2-OCHF$_2$ | 1.30(s. 3H), 3.45(br. 2H), 6.58(d. 1H), 6.98(d. 1H), 7.30(t. 1H). |
| IV'-25 | Q27 | 2-SCHF$_2$ | 3.81(br. 2H), 6.94(dd. 1H), 7.24(t. 1H), 7.25(d. 1H), 8.06(d. 1H). |
| IV'-26 | Q27 | 6-Me-2-SCHF$_2$ | 44–46° C. |
| IV'-27 | Q27 | 2-OCH(CF$_3$)$_2$ | 3.70(br. 2H), 6.40(m. 1H), 6.76(d. 1H), 7.08(dd. 1H), 7.59(d. 1H). |
| IV'-28 | Q27 | 6-Me-2-OCH(CF$_3$)$_2$ | 2.33(s. 3H), 3.45(br. 2H), 6.49(m. 1H), 6.64(d. 1H), 7.03(d. 1H). |
| IV'-29 | Q27 | 6-Cl-2-OCH(CF$_3$)$_2$ | 3.89(br. 2H), 6.24(m. 1H), 6.76(d. 1H), 7.16(d. 1H). |
| IV'-30 | Q27 | 6-F-2-OCH(CF$_3$)$_2$ | |
| IV'-31 | Q27 | 6-OMe-2-OCH(CF$_3$)$_2$ | 3.15–3.60(br. 2H), 3.95(s. 3H), 6.15(m. 1H), 6.38(d. 1H), 6.99(d. 1H). |
| IV'-32 | Q27 | 6-Cl-2-SCH(CF$_3$)$_2$ | |
| IV'-33 | Q27 | 6-Me-2-SCH(CF$_3$)$_2$ | |
| IV'-34 | Q27 | 6-F-2-SCH(CF$_3$)$_2$ | |
| IV'-35 | Q27 | 6-OMe-2-SCH(CF$_3$)$_2$ | |
| IV'-36 | Q27 | 2-OCF$_2$CHFOCF$_3$ | |
| IV'-37 | Q27 | 6-Me-2-OCF$_2$CHFOCF$_3$ | 2.35(s. 3H), 3.50(br. 2H), 6.31(dt. 1H), 6.77(d. 1H), 7.01(d. 1H). |
| IV'-38 | Q27 | 6-Cl-2-OCF$_2$CHFOCF$_3$ | |
| IV'-39 | Q27 | 2-OCF$_2$CHFO-n-C$_3$F$_7$ | 3.20(br. 2H), 6.43(dt. 1H), 6.84(d. 1H), 7.08(dd. 1H), 7.73(d. 1H). |
| IV'-40 | Q27 | 6-Me-2-OCF$_2$CHFO-n-C$_3$F$_7$ | 2.35(s. 3H), 3.60(br. 2H), 6.50(dt. 1H), 6.74(d. 1H), 7.02(d. 1H). |
| IV'-41 | Q27 | 6-Cl-2-OCF$_2$CHFO-n-C$_3$F$_7$ | 3.40(br. 2H), 6.37(dt. 1H), 6.85(d. 1H), 7.14(d. 1H). |
| IV'-42 | Q27 | 6-Me-2-OCF$_2$CHFCF$_3$ | 2.36(s. 3H), 3.30(br. 2H), 5.35(m. 1H), 6.76(d. 1H), 7.01(d. 1H). |
| IV'-43 | Q27 | 6-Me-2-OCF=CFCF$_3$ | 2.04(s. 3H), 3.10(br. 2H), 6.65(d. 0.5H), 6.69(d. 0.5H), 7.03(d. 1H). (E, Z mixture) |
| IV'-44 | Q27 | 6-Me-2-OCH(CF$_3$)$_2$ | 2.20(s. 3H), 3.20–3.60(br. 2H), 6.41(m. 1H), 6.67(s. 1H), 7.55(s. 1H). |
| IV'-45 | Q27 | 6-Me-2-OCF$_2$CHF$_2$ | 2.37(s. 3H), 3.40(br. 2H), 6.16(tt. 1H), 6.79(d. 1H), 7.06(d. 1H). |
| IV'-46 | Q27 | 6-Cl-2-OCF$_2$CHF$_2$ | 3.50(br. 2H), 6.11(tt. 1H), 6.88(d. 1H), 7.15(d. 1H). |
| IV'-47 | Q27 | 6-Me-2-OCH$_2$C$_2$F$_5$ | 2.31(s. 3H), 3.33(br. 2H), 4.75(t. 2H), 6.55(d. 1H), 6.98(d. 1H). |

General Formula (I)

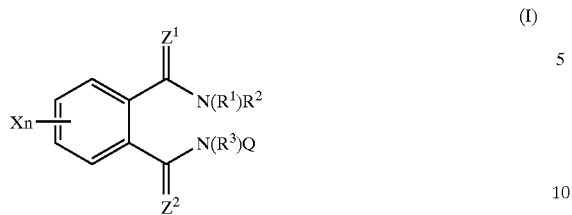

TABLE 2

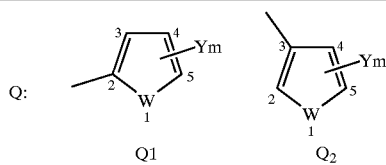

$(Z^1 = Z^2 = O)$

| Q | No. | Xn | R¹ | R² | R³ | W | Ym | mp (° C.) |
|---|---|---|---|---|---|---|---|---|
| Q1 | 1-1 | 3-Cl | H | i-Pr | H | O | H | |
| Q1 | 1-2 | 3-Cl | H | i-Pr | H | O | 3-Me-5-$C_2F_5$ | |
| Q1 | 1-3 | 3-Cl | H | i-Pr | H | S | 4,5-$Br_2$ | 143 |
| Q1 | 1-4 | 3-Br | H | i-Pr | H | O | 3-Me-5-n-$C_3F_7$ | |
| Q1 | 1-5 | 3-$NO_2$ | H | i-Pr | H | O | 3-Me-5-i-$C_3F_7$ | |
| Q1 | 1-6 | 3-I | H | i-Pr | H | S | H | |
| Q1 | 1-7 | 3-I | H | i-Pr | H | S | 3-Me | 207 |
| Q1 | 1-8 | 3-I | H | i-Pr | H | S | 5-Cl | |
| Q1 | 1-9 | 3-I | H | i-Pr | H | S | 5-$C_2F_5$ | |
| Q1 | 1-10 | 3-I | H | i-Pr | H | S | 5-n-$C_3F_7$ | |
| Q1 | 1-11 | 3-I | H | i-Pr | H | S | 5-i-$C_3F_7$ | |
| Q1 | 1-12 | 3-I | H | i-Pr | H | S | 3-Me-5-t-Bu | 160 |
| Q1 | 1-13 | 3-I | H | i-Pr | H | S | 3-Me-5-Br | |
| Q1 | 1-14 | 3-I | H | i-Pr | H | S | 3-Me-5-$C_2F_5$ | |
| Q1 | 1-15 | 3-I | H | i-Pr | H | S | 3-Me-5-n-$C_3F_7$ | |
| Q1 | 1-16 | 3-I | H | i-Pr | H | S | 3-Me-5-i-$C_3F_7$ | |
| Q1 | 1-17 | 3-I | H | i-Pr | H | S | 3-Me-4-$C_2F_5$ | |
| Q1 | 1-18 | 3-I | H | i-Pr | H | S | 3-Me-4-n-$C_3F_7$ | |
| Q1 | 1-19 | 3-I | H | i-Pr | H | S | 3-Me-4-i-$C_3F_7$ | |
| Q1 | 1-20 | 3-I | H | t-Bu | H | NMe | 5-i-$C_3F_7$ | |
| Q1 | 1-21 | 3-I | H | t-Bu | H | NMe | 5-$C_2F_5$ | |
| Q1 | 1-22 | 3-I | H | t-Bu | H | NMe | 5-n-$C_3F_7$ | |
| Q1 | 1-23 | 3-I | H | t-Bu | H | NMe | 3-Me-5-i-$C_3F_7$ | |
| Q1 | 1-24 | 3-I | H | $CH(CH_3)CH_2SCH_3$ | H | S | 3-Me-5-i-$C_3F_7$ | |
| Q1 | 1-25 | 3-I | H | $CH(CH_3)CH_2SOCH_3$ | H | S | 3-Me-5-i-$C_3F_7$ | |
| Q1 | 1-26 | 3-I | H | $CH(CH_3)CH_2SO_2CH_3$ | H | S | 3-Me-5-i-$C_3F_7$ | |
| Q1 | 1-27 | 3-I | H | $C(CH_3)_2CH_2SCH_3$ | H | S | 3-Me-5-i-$C_3F_7$ | |
| Q1 | 1-28 | 3-I | H | $C(CH_3)_2CH_2SOCH_3$ | H | S | 3-Me-5-i-$C_3F_7$ | |
| Q1 | 1-29 | 3-I | H | $C(CH_3)_2CH_2SO_2CH_3$ | H | S | 3-Me-5-i-$C_3F_7$ | |
| Q1 | 1-30 | 3-I | H | $CH(CH_3)CH_2NHAc$ | H | S | 3-Me-5-i-$C_3F_7$ | |
| Q1 | 1-31 | 3-I | H | $C(CH_3)_2CH_2NHAc$ | H | S | 3-Me-5-i-$C_3F_7$ | |
| Q1 | 1-32 | 3-I | H | $CH(CH_3)CH_2CH_2OCH_3$ | H | S | 3-Me-5-i-$C_3F_7$ | |
| Q1 | 1-33 | 3-I | H | $C(CH_3)_2CH_2CH_2OCH_3$ | H | S | 3-Me-5-i-$C_3F_7$ | |
| Q1 | 1-34 | 3-I | Et | Et | H | O | H | |
| Q1 | 1-35 | 3-I | Et | Et | H | O | 3-Me-5-$C_2F_5$ | |
| Q1 | 1-36 | 3-I | Et | Et | H | O | 3-Me-5-n-$C_3F_7$ | |
| Q1 | 1-37 | 3-I | Et | Et | H | O | 3-Me-5-i-$C_3F_7$ | |
| Q1 | 1-38 | 3-I | Et | Et | H | O | 5-Cl | |
| Q1 | 1-39 | 3-I | Et | Et | H | O | 5-Br | |
| Q1 | 1-40 | 3-I | Et | Et | H | O | 5-n-$C_3F_7$ | |
| Q1 | 1-41 | 6-I | H | i-Pr | H | S | 3-Me-5-t-Bu | 97 |
| Q1 | 1-42 | 6-I | H | i-Pr | H | S | 3-Me | 168 |
| Q1 | 1-43 | 3-$CF_3$ | H | i-Pr | H | NMe | 3-Me-5-$C_2F_5$ | |
| Q1 | 1-44 | 3-Ph | H | i-Pr | H | NMe | 3-Me-5-n-$C_3F_7$ | |
| Q1 | 1-45 | 3-$SOCF_3$ | H | i-Pr | H | NMe | 3-Me-5-i-$C_3F_7$ | |
| Q1 | 1-46 | 3-$C_2F_5$ | H | i-Pr | H | NMe | 3-Me-5-$C_2F_5$ | |
| Q1 | 1-47 | 3-I-4-Cl | H | i-Pr | H | NMe | 3-Me-5-n-$C_3F_7$ | |
| Q1 | 1-48 | 3-I-4-$CF_3$ | H | i-Pr | H | S | 3-Me-5-i-$C_3F_7$ | |
| Q1 | 1-49 | 3-$CF_3$-4-Cl | H | i-Pr | H | S | 3-Me-5-$C_2F_5$ | |
| Q1 | 1-50 | 3-$OCF_2O$-4 | H | i-Pr | H | S | 3-Me-5-n-$C_3F_7$ | |

TABLE 2-continued

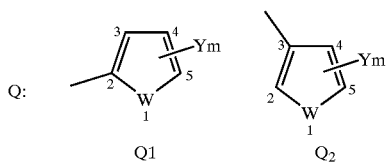

$(Z^1 = Z^2 = O)$

| Q | No. | Xn | $R^1$ | $R^2$ | $R^3$ | W | Ym | mp (° C.) |
|---|---|---|---|---|---|---|---|---|
| Q1 | 1-51 | 3-OCF$_2$CF$_2$O-4 | H | i-Pr | H | S | 3-Me-5-i-C$_3$F$_7$ | |
| Q2 | 2-1 | 3-I | H | i-Pr | H | 5 | 2-Me-5-C$_2$F$_5$ | |
| Q2 | 2-2 | 3-I | H | i-Pr | H | S | 2-Me-5-n-C$_3$F$_7$ | |
| Q2 | 2-3 | 3-I | H | i-Pr | H | S | 2-Me-5-i-C$_3$F$_7$ | |
| Q2 | 2-4 | 3-I | H | i-Pr | H | S | 4-Me-5-C$_2$F$_5$ | |
| Q2 | 2-5 | 3-I | H | i-Pr | H | S | 4-Me-n-C$_3$F$_7$ | |
| Q2 | 2-6 | 3-I | H | i-Pr | H | S | 4-Me-5-i-C$_3$F$_7$ | |
| Q2 | 2-7 | 3-I | H | t-Bu | H | NMe | 5-i-C$_3$F$_7$ | |
| Q2 | 2-8 | 3-I | H | t-Bu | H | NMe | 5-C$_2$F$_5$ | |
| Q2 | 2-9 | 3-I | H | t-Bu | H | NMe | 5-n-C$_3$F$_7$ | |
| Q2 | 2-10 | 3-I | H | t-Bu | H | NMe | 4-Me-5-i-C$_3$F$_7$ | |
| Q2 | 2-11 | 3-I | H | CH(CH$_3$)CH$_2$SCH$_3$ | H | S | 4-Me-5-i-C$_3$F$_7$ | |
| Q2 | 2-12 | 3-I | H | CH(CH$_3$)CH$_2$SOCH$_3$ | H | S | 4-Me-5-i-C$_3$F$_7$ | |
| Q2 | 2-13 | 3-I | H | CH(CH$_3$)CH$_2$SO$_2$CH$_3$ | H | S | 4-Me-5-i-C$_3$F$_7$ | |
| Q2 | 2-14 | 3-I | H | C(CH$_3$)$_2$CH$_2$SCH$_3$ | H | S | 2-Me-5-i-C$_3$F$_7$ | |
| Q2 | 2-15 | 3-I | H | C(CH$_3$)$_2$CH$_2$SOCH$_3$ | H | S | 2-Me-5-i-C$_3$F$_7$ | |
| Q2 | 2-16 | 3-I | H | C(CH$_3$)$_2$CH$_2$SO$_2$CH$_3$ | H | S | 2-Me-5-i-C$_3$F$_7$ | |
| Q2 | 2-17 | 3-I | H | CH(CH$_3$)CH$_2$NHAc | H | S | 2-Me-5-i-C$_3$F$_7$ | |
| Q2 | 2-18 | 3-I | H | C(CH$_3$)$_2$CH$_2$NHAc | H | S | 2-Me-5-i-C$_3$F$_7$ | |
| Q2 | 2-19 | 3-I | H | CH(CH$_3$)CH$_2$CH$_2$OCH$_3$ | H | S | 2-Me-5-i-C$_3$F$_7$ | |
| Q2 | 2-20 | 3-I | H | C(CH$_3$)$_2$CH$_2$CH$_2$OCH$_3$ | H | S | 4-Me-5-i-C$_3$F$_7$ | |
| Q2 | 2-21 | 3-I | Et | Et | H | O | H | |
| Q2 | 2-22 | 3-I | Et | Et | H | O | 2-Me-5-C$_2$F$_5$ | |
| Q2 | 2-23 | 3-I | Et | Et | H | O | 2-Me-5-n-C$_3$F$_7$ | |
| Q2 | 2-24 | 3-I | Et | Et | H | O | 4-Me-5-i-C$_3$F$_7$ | |

TABLE 3

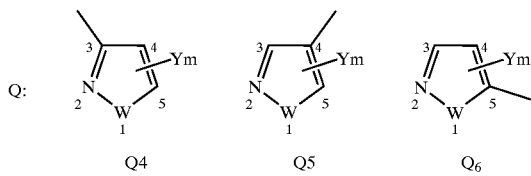

$(Z^1 = Z^2 = O)$

| Q | No. | Xn | $R^1$ | $R^2$ | $R^3$ | W | Ym | mp (° C.) |
|---|---|---|---|---|---|---|---|---|
| Q4 | 4-1 | H | H | i-Pr | H | O | 5-Me | 185 |
| Q4 | 4-2 | 3-Cl | H | i-Pr | H | O | H | |
| Q4 | 4-3 | 3-Cl | H | i-Pr | H | O | 4-Me-5-C$_2$F$_5$ | |
| Q4 | 4-4 | 3-Cl | H | i-Pr | H | O | 4,5-Br$_2$ | |
| Q4 | 4-5 | 3-Cl | H | i-Pr | H | O | 5-Me | 136 |
| Q4 | 4-6 | 3-Cl | H | i-Pr | H | O | 5-(4-Br-Ph) | 158 |
| Q4 | 4-7 | 3-Cl | H | i-Pr | H | O | 4-Me-5-(4-Cl-Ph) | 184 |
| Q4 | 4-8 | 6-Cl | H | i-Pr | H | O | 4-Me-5-(4-Cl-Ph) | 101 |
| Q4 | 4-9 | 3-Br | H | i-Pr | H | O | 4-Me-5-n-C$_3$F$_7$ | |
| Q4 | 4-10 | 3-NO$_2$ | H | i-Pr | H | O | 4-Me-5-i-C$_3$F$_7$ | |
| Q4 | 4-11 | 3-I | H | i-Pr | H | O | 4-Me | 144 |
| Q4 | 4-12 | 3-I | H | i-Pr | H | O | 4-Me-5-CF$_3$ | 151 |
| Q4 | 4-13 | 3-I | H | i-Pr | H | S | H | |
| Q4 | 4-14 | 3-I | H | i-Pr | H | S | 4-Me | |
| Q4 | 4-15 | 3-I | H | i-Pr | H | S | 5-Cl | |
| Q4 | 4-16 | 3-I | H | i-Pr | H | S | 5-C$_2$F$_5$ | |
| Q4 | 4-17 | 3-I | H | i-Pr | H | S | 5-n-C$_3$F$_7$ | |
| Q4 | 4-18 | 3-I | H | i-Pr | H | S | 5-i-C$_3$F$_7$ | |
| Q4 | 4-19 | 3-I | H | i-Pr | H | S | 4-Me-5-t-Bu | |
| Q4 | 4-20 | 3-I | H | i-Pr | H | S | 4-Me-5-Br | |
| Q4 | 4-21 | 3-I | H | i-Pr | H | S | 4-Me-5-C$_2$F$_5$ | |
| Q4 | 4-22 | 3-I | H | i-Pr | H | S | 4-Me-5-n-C$_3$F$_7$ | |
| Q4 | 4-23 | 3-I | H | i-Pr | H | S | 4-Me-5-i-C$_3$F$_7$ | |

TABLE 3-continued

Q:  Q4, Q5, Q6 (pyrazole structures with N2-W1, positions 3,4,5, Ym substituent)

($Z^1 = Z^2 = O$)

| Q | No. | Xn | $R^1$ | $R^2$ | $R^3$ | W | Ym | mp (° C.) |
|---|---|---|---|---|---|---|---|---|
| Q4 | 4-24 | 3-I | H | t-Bu | H | NMe | 5-i-$C_3F_7$ | |
| Q4 | 4-25 | 3-I | H | t-Bu | H | NMe | 5-$C_2F_7$ | |
| Q4 | 4-26 | 3-I | H | t-Bu | H | NMe | 5-n-$C_3F_7$ | |
| Q4 | 4-27 | 3-I | H | t-Bu | H | NMe | 4-Me-5-i-$C_3F_7$ | |
| Q4 | 4-28 | 3-I | H | CH(CH$_3$)CH$_2$SCH | H | S | 4-Me-5-i-$C_3F_7$ | |
| Q4 | 4-29 | 3-I | H | CH(CH$_3$)CH$_2$SOCH$_3$ | H | S | 4-Me-5-i-$C_3F_7$ | |
| Q4 | 4-30 | 3-I | H | CH(CH$_3$)CH$_2$SO$_2$CH$_3$ | H | S | 4-Me-5-i-$C_3F_7$ | |
| Q4 | 4-31 | 3-I | H | C(CH$_3$)$_2$CH$_2$SCH$_3$ | H | S | 4-Me-5-i-$C_3F_7$ | |
| Q4 | 4-32 | 3-I | H | C(CH$_3$)$_2$CH$_2$SOCH$_3$ | H | S | 4-Me-5-i-$C_3F_7$ | |
| Q4 | 4-33 | 3-I | H | C(CH$_3$)$_2$CH$_2$SO$_2$CH$_3$ | H | S | 4-Me-5-i-$C_3F_7$ | |
| Q4 | 4-34 | 3-I | H | CH(CH$_3$)CH$_2$NHAc | H | S | 4-Me-5-i-$C_3F_7$ | |
| Q4 | 4-35 | 3-I | H | C(CH$_3$)$_2$CH$_2$NHAc | H | S | 4-Me-5-i-$C_3F_7$ | |
| Q4 | 4-36 | 3-I | H | CH(CH$_3$)CH$_2$CH$_2$OCH$_3$ | H | S | 4-Me-5-i-$C_3F_7$ | |
| Q4 | 4-37 | 3-I | H | C(CH$_3$)$_2$CH$_2$CH$_2$OCH$_3$ | H | S | 4-Me-5-i-$C_3F_7$ | |
| Q4 | 4-38 | 3-I | Et | Et | | H | O | H |
| Q4 | 4-39 | 3-I | Et | Et | | H | O | 4-Me-5-$C_2F_5$ |
| Q4 | 4-40 | 3-I | Et | Et | | H | O | 4-Me-5-n-$C_3F_7$ |
| Q4 | 4-41 | 3-I | Et | Et | | H | O | 4-Me-5-i-$C_3F_7$ |
| Q4 | 4-42 | 3-I | Et | Et | | H | O | 5-Cl |
| Q4 | 4-43 | 3-I | Et | Et | | H | O | 5-Br |
| Q4 | 4-44 | 3-I | Et | Et | | H | O | 5-n-$C_3F_7$ |
| Q4 | 4-45 | 6-I | H | i-Pr | H | O | 4-Me-5-$CF_3$ | 143 |
| Q4 | 4-46 | 3-$CF_3$ | H | i-Pr | H | NMe | 4-Me-5-$C_2F_5$ | |
| Q4 | 4-47 | 3-Ph | H | i-Pr | H | NMe | 4-Me-5-n-$C_3F_7$ | |
| Q4 | 4-48 | 3-SOCF$_3$ | H | i-Pr | H | NMe | 4-Me-5-i-$C_3F_7$ | |
| Q4 | 4-49 | 3-$C_2F_5$ | H | i-Pr | H | NMe | 4-Me-5-$C_2F_5$ | |
| Q4 | 4-50 | 3-I-4-Cl | H | i-Pr | H | NMe | 4-Me-5-n-$C_3F_7$ | |
| Q4 | 4-51 | 3-I-4-$CF_3$ | H | i-Pr | H | S | 4-Me-5-i-$C_3F_7$ | |
| Q4 | 4-52 | 3-$CF_3$-4-Cl | H | i-Pr | H | S | 4-Me-5-$C_2F_5$ | |
| Q4 | 4-53 | 3-OCF$_2$O-4 | H | i-Pr | H | S | 4-Me-5-n-$C_3F_7$ | |
| Q4 | 4-54 | 3-OCF$_2$CF$_2$O-4 | H | i-Pr | H | S | 4-Me-5-i-$C_3F_7$ | |
| Q5 | 5-1 | 3-Cl | H | i-Pr | H | O | H | |
| Q5 | 5-2 | 3-Cl | H | i-Pr | H | O | 3-Me-5-Cl | |
| Q5 | 5-3 | 3-Cl | H | i-Pr | H | O | 3,5-Br$_2$ | |
| Q5 | 5-4 | 3-Cl | H | i-Pr | H | NMe | 3-Me | 180 |
| Q5 | 5-5 | 3-Cl | H | i-Pr | H | NMe | 3-Me-5-OMe | 220 |
| Q5 | 5-6 | 3-Cl | H | n-Pr | H | NMe | 3-Me-5-OMe | 90 |
| Q5 | 5-7 | 3-Cl | H | n-Pr | H | NMe | 3-Me-5-OPh | 190 |
| Q5 | 5-8 | 6-Cl | H | i-Pr | H | NMe | 3-Me-5-OPh | 245 |
| Q5 | 5-9 | 6-Cl | H | i-Pr | H | NMe | 3-Me-5-OMe | 175 |
| Q5 | 5-10 | 3-Br | H | i-Pr | H | O | 3,5-Me$_2$ | |
| Q5 | 5-11 | 3-NO$_2$ | H | i-Pr | H | O | 3,5-Me$_2$ | |
| Q5 | 5-12 | 3-I | H | i-Pr | H | O | 3-$CF_3$ | |
| Q5 | 5-13 | 3-I | H | i-Pr | H | O | 5-$CF_3$ | |
| Q5 | 5-14 | 3-I | H | i-Pr | H | S | H | |
| Q5 | 5-15 | 3-I | H | i-Pr | H | S | 3-Me | |
| Q5 | 5-16 | 3-I | H | i-Pr | H | S | 5-Cl | |
| Q5 | 5-17 | 3-I | H | i-Pr | H | S | 5-$C_2F_5$ | |
| Q5 | 5-18 | 3-I | H | i-Pr | H | S | 5-n-$C_3F_7$ | |
| Q5 | 5-19 | 3-I | H | i-Pr | H | S | 5-i-$C_3F_7$ | |
| Q5 | 5-20 | 3-I | H | i-Pr | H | S | 3-$C_2F_5$ | |
| Q5 | 5-21 | 3-I | H | i-Pr | H | S | 3-n-$C_3F_7$ | |
| Q5 | 5-22 | 3-I | H | i-Pr | H | S | 3-i-$C_3F_7$ | |
| Q5 | 5-23 | 3-I | H | i-Pr | H | S | 3-Me-5-Br | |
| Q5 | 5-24 | 3-I | H | i-Pr | H | S | 3-Me-5-$C_2F_5$ | |
| Q5 | 5-25 | 3-I | H | i-Pr | H | S | 3-Me-5-n-$C_3F_7$ | |
| Q5 | 5-26 | 3-I | H | i-Pr | H | S | 3-Me-5-i-$C_3F_7$ | |
| Q5 | 5-27 | 3-I | H | t-Bu | H | NMe | 5-i-$C_3F_7$ | |
| Q5 | 5-28 | 3-I | H | t-Bu | H | NMe | 5-$C_2F_5$ | |
| Q5 | 5-29 | 3-I | H | t-Bu | H | NMe | 5-n-$C_3F_7$ | |
| Q5 | 5-30 | 3-I | H | CH(CH$_3$)CH$_2$SCH$_3$ | H | NMe | 3,5-Me$_2$ | |
| Q5 | 5-31 | 3-I | H | CH(CH$_3$)CH$_2$SOCH$_3$ | H | NMe | 3,5-Me$_2$ | |
| Q5 | 5-32 | 3-I | H | CH(CH$_3$)CH$_2$SO$_2$CH$_3$ | H | NMe | 3,5-Me$_2$ | |
| Q5 | 5-33 | 3-I | H | C(CH$_3$)$_2$CH$_2$SCH$_3$ | H | NMe | 3,5-Me$_2$ | |
| Q5 | 5-34 | 3-I | H | C(CH$_3$)$_2$CH$_2$SOCH$_3$ | H | NMe | 3,5-Me$_2$ | |

TABLE 3-continued

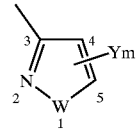

Q4  Q5  Q6

($Z^1 = Z^2 = O$)

| Q | No. | Xn | $R^1$ | $R^2$ | $R^3$ | W | Ym | mp (° C.) |
|---|---|---|---|---|---|---|---|---|
| Q5 | 5-35 | 3-I | H | C(CH$_3$)$_2$CH$_2$SO$_2$CH$_3$ | H | NMe | 3,5-Me$_2$ | |
| Q5 | 5-36 | 3-I | H | CH(CH$_3$)CH$_2$NHAC | H | NMe | 3,5-Me$_2$ | |
| Q5 | 5-37 | 3-I | H | C(CH$_3$)$_2$CH$_2$NHAC | H | NMe | 3,5-Me$_2$ | |
| Q5 | 5-38 | 3-I | H | CH(CH$_3$)CH$_2$CH$_2$OCH$_3$ | H | NMe | 3,5-Me$_2$ | |
| Q5 | 5-39 | 3-I | H | C(CH$_3$)$_2$CH$_2$CH$_2$OCH$_3$ | H | NMe | 3,5-Me$_2$ | |
| Q5 | 5-40 | 3-I | Et | Et | H | O | H | |
| Q5 | 5-41 | 3-I | Et | Et | H | O | 3-Me-5-C$_2$F$_5$ | |
| Q5 | 5-42 | 3-I | Et | Et | H | O | 3-Me-5-n-C$_3$F$_7$ | |
| Q5 | 5-43 | 3-I | Et | Et | H | O | 3-Me-5-i-C$_3$F$_7$ | |
| Q5 | 5-44 | 3-I | Et | Et | H | O | 5-Cl | |
| Q5 | 5-45 | 3-I | Et | Et | H | O | 5-Br | |
| Q5 | 5-46 | 3-I | Et | Et | H | O | 5-n-C$_3$F$_7$ | |
| Q5 | 5-47 | 3-I | Et | Et | H | O | 5-n-C$_3$F$_7$ | |
| Q5 | 5-48 | 3-CF$_3$ | H | i-Pr | H | NMe | 3-Me-5-C$_2$F$_5$ | |
| Q5 | 5-49 | 3-Ph | H | i-Pr | H | NMe | 3-Me-5-n-C$_3$F$_7$ | |
| Q5 | 5-50 | 3-SOCF$_3$ | H | i-Pr | H | NMe | 3-Me-5-i-C$_3$F$_7$ | |
| Q5 | 5-51 | 3-C$_2$F$_5$ | H | i-Pr | H | NMe | 3-Me-5-C$_2$F$_5$ | |
| Q5 | 5-52 | 3-I-4-Cl | H | i-Pr | H | NMe | 3-Me-5-n-C$_3$F$_7$ | |
| Q5 | 5-53 | 3-I-4-CF$_3$ | H | i-Pr | H | S | 3-Me-5-i-C$_3$F$_7$ | |
| Q5 | 5-54 | 3-CF$_3$-4-Cl | H | i-Pr | H | S | 3-Me-5-C$_2$F$_5$ | |
| Q5 | 5-55 | 3-OCF$_2$O-4 | H | i-Pr | H | S | 3-Me-5-n-C$_3$F$_7$ | |
| Q5 | 5-56 | 3-OCF$_2$CF$_2$O-4 | H | i-Pr | H | S | 3-Me-5-i-C$_3$F$_7$ | |
| Q6 | 6-1 | 3-Cl | H | i-Pr | H | O | H | |
| Q6 | 6-2 | 3-Cl | H | i-Pr | H | O | 4-Me-3-C$_2$F$_5$ | |
| Q6 | 6-3 | 3-Cl | H | i-Pr | H | O | 3,4-Br$_2$ | |
| Q6 | 6-4 | 3-Br | H | i-Pr | H | O | 4-Me-3-n-C$_3$F$_7$ | |
| Q6 | 6-5 | 3-NO$_2$ | H | i-Pr | H | O | 4-Me-3-i-C$_3$F$_7$ | |
| Q6 | 6-6 | 3-NO$_2$ | H | i-Pr | H | NMe | 3-Me | 176 |
| Q6 | 6-7 | 3-I | H | i-Pr | H | O | 4-Me-3-Et | 85 |
| Q6 | 6-8 | 3-I | H | i-Pr | H | O | 4-Me-3-CF$_3$ | 103 |
| Q6 | 6-9 | 3-I | H | i-Pr | H | S | H | |
| Q6 | 6-10 | 3-I | H | i-Pr | H | S | 4-Me | |
| Q6 | 6-11 | 3-I | H | i-Pr | H | S | 3-Cl | |
| Q6 | 6-12 | 3-I | H | i-Pr | H | S | 3-C$_2$F$_5$ | |
| QE | 6-13 | 3-I | H | i-Pr | H | S | 3-n-C$_3$F$_7$ | |
| Q6 | 6-14 | 3-I | H | i-Pr | H | S | 3-i-C$_3$F$_7$ | |
| Q6 | 6-15 | 3-I | H | i-Pr | H | S | 4-Me-3-t-Bu | |
| Q6 | 6-16 | 3-I | H | i-Pr | H | S | 4-Me-3-Br | |
| Q6 | 6-17 | 3-I | H | i-Pr | H | S | 4-Me-3-C$_2$F$_5$ | |
| Q6 | 6-18 | 3-I | H | i-Pr | H | S | 4-Me-3-n-C$_3$F$_7$ | |
| Q6 | 6-19 | 3-I | H | i-Pr | H | S | 4-Me-3-i-C$_3$F$_7$ | |
| Q6 | 6-20 | 3-I | H | t-Bu | H | NMe | 3-i-C$_3$F$_7$ | |
| Q6 | 6-21 | 3-I | H | t-Bu | H | NMe | 3-C$_2$F$_5$ | |
| Q6 | 6-22 | 3-I | H | t-Bu | H | NMe | 3-n-C$_3$F$_7$ | |
| Q6 | 6-23 | 3-I | H | t-Bu | H | NMe | 4-Me-3-i-C$_3$F$_7$ | |
| Q6 | 6-24 | 3-I | H | CH(CH$_3$)CH$_2$SCH$_3$ | H | S | 4-Me-3-i-C$_3$F$_7$ | |
| Q6 | 6-25 | 3-I | H | CH(CH$_3$)CH$_2$SOCH$_3$ | H | S | 4-Me-3-i-C$_3$F$_7$ | |
| Q6 | 6-26 | 3-I | H | CH(CH$_3$)CH$_2$SO$_2$CH$_3$ | H | S | 4-Me-3-i-C$_3$F$_7$ | |
| Q6 | 6-27 | 3-I | H | C(CH$_3$)$_2$CH$_2$SCH$_3$ | H | S | 4-Me-3-i-C$_3$F$_7$ | |
| Q6 | 6-28 | 3-I | H | C(CH$_3$)$_2$CH$_2$SOCH$_3$ | H | S | 4-Me-3-i-C$_3$F$_7$ | |
| Q6 | 6-29 | 3-I | H | C(CH$_3$)$_2$CH$_2$SO$_2$CH$_3$ | H | S | 4-Me-3-i-C$_3$F$_7$ | |
| Q6 | 6-30 | 3-I | H | CH(CH$_3$)CH$_2$NHAc | H | S | 4-Me-3-i-C$_3$F$_7$ | |
| Q6 | 6-31 | 3-I | H | C(CH$_3$)$_2$CH$_2$NHAc | H | S | 4-Me-3-i-C$_3$F$_7$ | |
| Q6 | 6-32 | 3-I | H | CH(CH$_3$)CH$_2$CH$_2$OCH$_3$ | H | S | 4-Me-3-i-C$_3$F$_7$ | |
| Q6 | 6-33 | 3-I | H | C(CH$_3$)$_2$CH$_2$CH$_2$OCH$_3$ | H | S | 4-Me-3-i-C$_3$F$_7$ | |
| Q6 | 6-34 | 3-I | Et | Et | H | O | H | |
| Q6 | 6-35 | 3-I | Et | Et | H | O | 4-Me-3-C$_2$F$_5$ | |
| Q6 | 6-36 | 3-I | Et | Et | H | O | 4-Me-3-n-C$_3$F$_7$ | |
| Q6 | 6-37 | 3-I | Et | Et | H | O | 4-Me-3-i-C$_3$F$_7$ | |
| Q6 | 6-38 | 3-I | Et | Et | H | O | 3-Cl | |
| Q6 | 6-39 | 3-I | Et | Et | H | O | 3-Br | |
| Q6 | 6-40 | 3-I | Et | Et | H | O | 3-n-C$_3$F$_7$ | |
| Q6 | 6-41 | 3-CF$_3$ | H | i-Pr | H | NMe | 4-Me-3-C$_2$F$_5$ | |
| Q6 | 6-42 | 3-Ph | H | i-Pr | H | NMe | 4-Me-3-n-C$_3$F$_7$ | |
| Q6 | 6-43 | 3-SOCF$_3$ | H | i-Pr | H | NMe | 4-Me-3-i-C$_3$F$_7$ | |

TABLE 3-continued

Q: Q4, Q5, Q6 (pyrazole structures with positions 1-5, W at 1, N at 2, methyl at 3, Ym at 4 for Q4 and Q5; Q6 has methyl at 5 and Ym at 4)

($Z^1 = Z^2 = O$)

| Q | No. | Xn | $R^1$ | $R^2$ | $R^3$ | W | Ym | mp (° C.) |
|---|---|---|---|---|---|---|---|---|
| Q6 | 6-44 | 3-$C_2F_5$ | H | i-Pr | H | NMe | 4-Me-3-$C_2F_5$ | |
| Q6 | 6-45 | 3-I-4-Cl | H | i-Pr | H | NMe | 4-Me-3-n-$C_3F_7$ | |
| Q6 | 6-46 | 3-I-4-$CF_3$ | H | i-Pr | H | S | 4-Me-3-i-$C_3F_7$ | |
| Q6 | 6-47 | 3-$CF_3$-4-Cl | H | i-Pr | H | S | 4-Me-3-$C_2F_5$ | |
| Q6 | 6-48 | 3-$OCF_2$O-4 | H | i-Pr | H | S | 4-Me-3-n-$C_3F_7$ | |
| Q6 | 6-49 | 3-$OCF_2CF_2$O-4 | H | i-Pr | H | S | 4-Me-3-i-$C_3F_7$ | |

TABLE 4

Q: Q8, Q9, Q10 (imidazole structures)

($Z^1 = Z^2 = O$)

| Q | No. | Xn | $R^1$ | $R^2$ | $R^3$ | W | Ym | mp (° C.) |
|---|---|---|---|---|---|---|---|---|
| Q8 | 8-1 | 3-Cl | H | i-Pr | H | S | H | 137 |
| Q8 | 8-2 | 3-Cl | H | i-Pr | H | S | 4-Me | 175 |
| Q8 | 8-3 | 3-Cl | H | i-Pr | H | S | 4-$CF_3$ | 185 |
| Q8 | 8-4 | 3-Cl | H | i-Pr | H | S | 4-Ph | 175 |
| Q8 | 8-5 | 3-Cl | H | i-Pr | H | S | 4-Ph-5-Cl | 205 |
| Q8 | 8-6 | 3-Cl | H | i-Pr | H | O | 4-Me-5-Cl | |
| Q8 | 8-7 | 3-Cl | H | i-Pr | H | O | 4,5-$Br_2$ | |
| Q8 | 8-8 | 3-Cl | H | i-Pr | H | NMe | 4-Me | |
| Q8 | 8-9 | 3-Cl | H | i-Pr | H | NMe | 4-Me-5-OMe | |
| Q8 | 8-10 | 3-Cl | H | n-Pr | H | NMe | 4-Me-5-OMe | |
| Q8 | 8-11 | 3-Cl | H | n-Pr | H | NMe | 4-Me-5-OPh | |
| Q8 | 8-12 | 6-Cl | H | i-Pr | H | S | 4-$CH_3$ | 155 |
| Q8 | 8-13 | 6-Cl | H | i-Pr | H | S | 4-$CF_3$ | 165 |
| Q8 | 8-14 | 6-Cl | H | i-Pr | H | S | 4-Ph | 155 |
| Q8 | 8-15 | 6-Cl | H | i-Pr | H | S | 4-Ph-5-Cl | 155 |
| Q8 | 8-16 | 3-Br | H | i-Pr | H | O | 4,5-$Me_2$ | |
| Q8 | 8-17 | 3-$NO_2$ | H | i-Pr | H | O | 4,5-$Me_2$ | |
| Q8 | 8-18 | 3-I | H | i-Pr | H | O | 4-$CF_3$ | |
| Q8 | 8-19 | 3-I | H | i-Pr | H | O | 5-$CF_3$ | |
| Q8 | 8-20 | 3-I | H | i-Pr | H | S | H | |
| Q8 | 8-21 | 3-I | H | i-Pr | H | S | 4-Me | |
| Q8 | 8-22 | 3-I | H | i-Pr | H | S | 5-Cl | |
| Q8 | 8-23 | 3-I | H | i-Pr | H | S | 5-$C_2F_5$ | |
| Q8 | 8-24 | 3-I | H | i-Pr | H | S | 5-n-$C_3F_7$ | |
| Q8 | 8-25 | 3-I | H | i-Pr | H | S | 5-i-$C_3F_7$ | |
| Q8 | 8-26 | 3-I | H | i-Pr | H | S | 4-$C_2F_5$ | |
| Q8 | 8-27 | 3-I | H | i-Pr | H | S | 4-n-$C_3F_7$ | |
| Q8 | 8-28 | 3-I | H | i-Pr | H | S | 4-i-$C_3F_7$ | |
| Q8 | 8-29 | 3-I | H | i-Pr | H | S | 4-Me-5-Br | |
| Q8 | 8-30 | 3-I | H | i-Pr | H | S | 4-Me-5-$C_2F_5$ | |
| Q8 | 8-31 | 3-I | H | i-Pr | H | S | 4-Me-5-n-$C_3F_7$ | |
| Q8 | 8-32 | 3-I | H | i-Pr | H | S | 4-Me-5-i-$C_3F_7$ | |
| Q8 | 8-33 | 3-I | H | t-Bu | H | NMe | 5-i-$C_3F_7$ | |
| Q8 | 8-34 | 3-I | H | t-Bu | H | NMe | 5-$C_2F_5$ | |
| Q8 | 8-35 | 3-I | H | t-Bu | H | NMe | 5-n-$C_3F_7$ | |
| Q8 | 8-36 | 3-I | H | CH($CH_3$)$CH_2SCH_3$ | H | NMe | 4,5-$Me_2$ | |
| Q8 | 8-37 | 3-I | H | CH($CH_3$)$CH_2SO_2CH_3$ | H | NMe | 4,5-$Me_2$ | |
| Q8 | 8-38 | 3-I | H | CH($CH_3$)$_2SOCH_3$ | H | NMe | 4,5-$Me_2$ | |
| Q8 | 8-39 | 3-I | H | C($CH_3$)$_2CH_2SCH_3$ | H | NMe | 4,5-$Me_2$ | |
| Q8 | 8-40 | 3-I | H | C($CH_3$)$_2CH_2OCH_3$ | H | NMe | 4,5-$Me_2$ | |
| Q8 | 8-41 | 3-I | H | C($CH_3$)$_2CH_2SO_2CH_3$ | H | NMe | 4,5-$Me_2$ | |

TABLE 4-continued

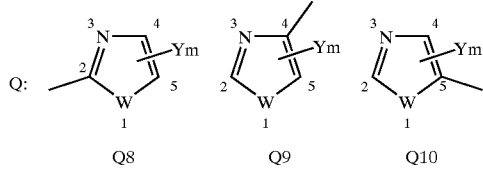

Q8　　　　　　　　Q9　　　　　　　　Q10

($Z^1 = Z^2 = O$)

| Q | No. | Xn | $R^1$ | $R^2$ | $R^3$ | W | Ym | mp (° C.) |
|---|---|---|---|---|---|---|---|---|
| Q8 | 8-42 | 3-I | H | CH(CH$_3$)CH$_2$NHAc | H | NMe | 4,5-Me$_2$ | |
| Q8 | 8-43 | 3-I | H | C(CH$_3$)$_2$CH$_2$NHAc | H | NMe | 4,5-Me$_2$ | |
| Q8 | 8-44 | 3-I | H | CH(CH$_3$)CH$_2$CH$_2$OCH$_3$ | H | NMe | 4,5-Me$_2$ | |
| Q8 | 8-45 | 3-I | H | C(CH$_3$)$_2$CH$_2$CH$_2$OCH$_3$ | H | NMe | 4,5-Me$_2$ | |
| Q8 | 8-46 | 3-I | Et | Et | H | O | H | |
| Q8 | 8-47 | 3-I | Et | Et | H | O | 5-C$_2$F$_5$ | |
| Q8 | 8-48 | 3-I | Et | Et | H | O | 4-n-C$_3$F$_7$ | |
| Q8 | 8-49 | 3-I | Et | Et | H | O | 4-i-C$_3$F$_7$ | |
| Q8 | 8-50 | 3-I | Et | Et | H | O | 5-Cl | |
| Q8 | 8-51 | 3-I | Et | Et | H | O | 5-Br | |
| Q8 | 8-52 | 3-I | Et | Et | H | O | 5-n-C$_3$F$_7$ | |
| Q8 | 8-53 | 3-I | Et | Et | H | S | 4-(4-Cl-Ph) | 139 |
| Q8 | 8-54 | 3-CF$_3$ | H | i-Pr | H | NMe | 5-C$_2$F$_5$ | |
| Q8 | 8-55 | 3-Ph | H | i-Pr | H | NMe | 4-n-C$_3$F$_7$ | |
| Q8 | 8-56 | 3-SOCF$_3$ | H | i-Pr | H | NMe | 4-i-C$_3$F$_7$ | |
| Q8 | 8-57 | 3-C$_2$F$_5$ | H | i-Pr | H | NMe | 5-C$_2$F$_5$ | |
| Q8 | 8-58 | 3-I-4-Cl | H | i-Pr | H | NMe | 4-n-C$_3$F$_7$ | |
| Q8 | 8-59 | 3-I-4-CF$_3$ | H | i-Pr | H | S | 4-i-C$_3$F$_7$ | |
| Q8 | 8-60 | 3-CF$_3$-4-Cl | H | i-Pr | H | S | 5-C$_2$F$_5$ | |
| Q8 | 8-61 | 3-OCF$_2$O-4 | H | i-Pr | H | S | 4-n-C$_3$F$_7$ | |
| Q8 | 8-62 | 3-OCF$_2$F$_2$O-4 | H | i-Pr | H | S | 4-i-C$_3$F$_7$ | |
| Q8 | 8-63 | 3-I | H | i-Pr | H | S | 4-S-Et | 86 |
| Q8 | 8-64 | 6-I | H | i-Pr | H | S | 4-S-Et | 135 |
| Q8 | 8-65 | 3-I | H | i-Pr | H | S | 4-Me-5-CO$_2$-Et | Amorphoussolid |
| Q9 | 9-1 | 3-Cl | H | i-Pr | H | O | H | |
| Q9 | 9-2 | 3-Cl | H | i-Pr | H | O | 5-Me-2-C$_2$F$_5$ | |
| Q9 | 9-3 | 3-Cl | H | i-Pr | H | O | 2,5-Br$_2$ | |
| Q9 | 9-4 | 3-Cl | H | i-Pr | H | S | 2-Ph | 131 |
| Q9 | 9-5 | 3-Br | H | i-Pr | H | O | 5-Me-2-n-C$_3$F$_7$ | |
| Q9 | 9-6 | 3-NO$_2$ | H | i-Pr | H | O | 5-Me-2-i-C$_3$F$_7$ | |
| Q9 | 9-7 | 3-I | H | i-Pr | H | O | 5-Me-2-CF$_3$ | |
| Q9 | 9-8 | 3-I | H | i-Pr | H | S | H | |
| Q9 | 9-9 | 3-I | H | i-Pr | H | S | 2-Me | |
| Q9 | 9-10 | 3-I | H | i-Pr | H | S | 2-Cl | |
| Q9 | 9-11 | 3-I | H | i-Pr | H | S | 2-C$_2$F$_5$ | |
| Q9 | 9-12 | 3-I | H | i-Pr | H | S | 2-n-C$_3$F$_7$ | |
| Q9 | 9-13 | 3-I | H | i-Pr | H | S | 2-i-C$_3$F$_7$ | |
| Q9 | 9-14 | 3-I | H | i-Pr | H | S | 5-Me-2-t-Bu | |
| Q9 | 9-15 | 3-I | H | i-Pr | H | S | 5-Me-2-I | 135 |
| Q9 | 9-16 | 3-I | H | i-Pr | H | S | 5-Me-2-C$_2$F$_5$ | |
| Q9 | 9-17 | 3-I | H | i-Pr | H | S | 5-Me-2-n-C$_3$F$_7$ | |
| Q9 | 9-18 | 3-I | H | i-Pr | H | S | 5-Me-2-i-C$_3$F$_7$ | |
| Q9 | 9-19 | 3-I | H | i-Pr | H | S | 5-Me-2-I | 191 |
| Q9 | 9-20 | 3-I | H | t-Bu | H | NMe | 2-i-C$_3$F$_7$ | |
| Q9 | 9-21 | 3-I | H | t-Bu | H | NMe | 2-C$_2$F$_5$ | |
| Q9 | 9-22 | 3-I | H | t-Bu | H | NMe | 2-n-C$_3$F$_7$ | |
| Q9 | 9-23 | 3-I | H | t-Bu | H | NMe | 5-Me-2-i-C$_3$F$_7$ | |
| Q9 | 9-24 | 3-I | H | CH(CH$_3$)CH$_2$SCH$_3$ | H | S | 5-Me-2-i-C$_3$F$_7$ | |
| Q9 | 9-25 | 3-I | H | CH(CH$_3$)CH$_2$SOCH$_3$ | H | S | 5-Me-2-i-C$_3$F$_7$ | |
| Q9 | 9-26 | 3-I | H | CH(CH$_3$)CH$_2$SO$_2$CH$_3$ | H | S | 5-Me-2-i-C$_3$F$_7$ | |
| Q9 | 9-27 | 3-I | H | C(CH$_3$)$_2$CH$_2$SCH$_3$ | H | S | 5-Me-2-i-C$_3$F$_7$ | |
| Q9 | 9-28 | 3-I | H | C(CH$_3$)$_2$CH$_2$SOCH$_3$ | H | S | 5-Me-2-i-C$_3$F$_7$ | |
| Q9 | 9-29 | 3-I | H | C(CH$_3$)$_2$CH$_2$SO$_2$CH$_3$ | H | S | 5-Me-2-i-C$_3$F$_7$ | |
| Q9 | 9-30 | 3-I | H | CH(CH$_3$)CH$_2$NHAC | H | S | 5-Me-2-i-C$_3$F$_7$ | |
| Q9 | 9-31 | 3-I | H | C(CH$_3$)$_2$CH$_2$NHAc | H | S | 5-Me-2-i-C$_3$F$_7$ | |
| Q9 | 9-32 | 3-I | Et | Et | H | O | H | |
| Q9 | 9-33 | 3-I | Et | Et | H | O | 5-Me-2-C$_2$F$_5$ | |
| Q9 | 9-34 | 3-I | Et | Et | H | O | 5-Me-2-n-C$_3$F$_7$ | |
| Q9 | 9-35 | 3-I | Et | Et | H | O | 5-Me-2-i-C$_3$F$_7$ | |
| Q9 | 9-36 | 3-I | Et | Et | H | O | 2-Cl | |
| Q9 | 9-37 | 3-I | Et | Et | H | O | 2-Br | |
| Q9 | 9-38 | 3-I | Et | Et | H | O | 2-n-C$_3$F$_7$ | |
| Q9 | 9-39 | 3-CF$_3$ | H | i-Pr | H | NMe | 5-Me-2-C$_2$F$_5$ | |
| Q9 | 9-40 | 3-Ph | H | i-Pr | H | NMe | 5-Me-2-n-C$_3$F$_7$ | |
| Q9 | 9-41 | 3-SOCF$_3$ | H | i-Pr | H | NMe | 5-Me-2-i-C$_3$F$_7$ | |

TABLE 4-continued

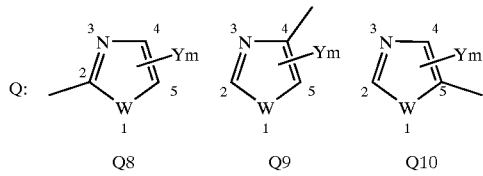

Q8  Q9  Q10

($Z^1 = Z^2 = O$)

| Q | No. | Xn | $R^1$ | $R^2$ | $R^3$ | W | Ym | mp (° C.) |
|---|---|---|---|---|---|---|---|---|
| Q9 | 9-42 | 3-$C_2F_5$ | H | i-Pr | H | NMe | 5-Me-2-$C_2F_5$ | |
| Q9 | 9-43 | 3-I-4-Cl | H | i-Pr | H | NMe | 5-Me-2-n-$C_3F_7$ | |
| Q9 | 9-44 | 3-I-4-$CF_3$ | H | i-Pr | H | S | 5-Me-2-i-$C_3F_7$ | |
| Q9 | 9-45 | 3-$CF_3$-4-Cl | H | i-Pr | H | S | 5-Me-2-$C_2F_5$ | |
| Q9 | 9-46 | 3-$OCF_2O$-4 | H | i-Pr | H | S | 5-Me-2-n-$C_3F_7$ | |
| Q9 | 9-47 | 3-$OCF_2F_2O$-4 | H | i-Pr | H | S | 5-Me-2-i-$C_3F_7$ | |
| Q10 | 10-1 | 3-Cl | H | i-Pr | H | O | H | |
| Q10 | 10-2 | 3-Cl | H | i-Pr | H | O | 4-Me-2-$C_2F_5$ | |
| Q10 | 10-3 | 3-Cl | H | i-Pr | H | O | 2,4-$Br_2$ | |
| Q10 | 10-4 | 3-Cl | H | i-Pr | H | O | 2-Ph | |
| Q10 | 10-5 | 3-Br | H | i-Pr | H | O | 4-Me-2-n-$C_3F_7$ | |
| Q10 | 10-6 | 3-$NO_2$ | H | i-Pr | H | O | 4-Me-2-i-$C_3F_7$ | |
| Q10 | 10-7 | 3-I | H | i-Pr | H | O | 4-Me | 230 |
| Q10 | 10-8 | 3-I | H | i-Pr | H | O | 4-Me-2-$CF_3$ | |
| Q10 | 10-9 | 3-I | H | i-Pr | H | S | H | |
| Q10 | 10-10 | 3-I | H | i-Pr | H | S | 4-Me | |
| Q10 | 10-11 | 3-I | H | i-Pr | H | S | 2-Cl | |
| Q10 | 10-12 | 3-I | H | i-Pr | H | S | 2-$C_2F_5$ | |
| Q10 | 10-13 | 3-I | H | i-Pr | H | S | 2-n-$C_3F_7$ | |
| Q10 | 10-14 | 3-I | H | i-Pr | H | S | 2-i-$C_3F_7$ | |
| Q10 | 10-15 | 3-I | H | i-Pr | H | S | 4-Me-2-t-Bu | |
| Q10 | 10-16 | 3-I | H | i-Pr | H | S | 4-Me-2-I | |
| Q10 | 10-17 | 3-I | H | i-Pr | H | S | 4-Me-2-$C_2F_5$ | |
| Q10 | 10-18 | 3-I | H | i-Pr | H | S | 4-Me-2-n-$C_3F_7$ | |
| Q10 | 10-19 | 3-I | H | i-Pr | H | S | 4-Me-2-i-$C_3F_7$ | |
| Q10 | 10-20 | 6-I | H | i-Pr | H | S | 4-Me | 198 |
| Q10 | 10-21 | 3-I | H | t-Bu | H | NMe | 2-i-$C_3F_7$ | |
| Q10 | 10-22 | 3-I | H | t-Bu | H | NMe | 2-$C_2F_5$ | |
| Q10 | 10-23 | 3-I | H | t-Bu | H | NMe | 2-n-$C_3F_7$ | |
| Q10 | 10-24 | 3-I | H | t-Bu | H | NMe | 4-Me-2-i-$C_3F_7$ | |
| Q10 | 10-25 | 3-I | H | $CH(CH_3)CH_2SCH_3$ | H | S | 4-Me-2-i-$C_3F_7$ | |
| Q10 | 10-26 | 3-I | H | $CH(CH_3)CH_2SOCH_3$ | H | S | 4-Me-2-i-$C_3F_7$ | |
| Q10 | 10-27 | 3-I | H | $CH(CH_3)CH_2SO_2CH_3$ | H | S | 4-Me-2-i-$C_3F_7$ | |
| Q10 | 10-28 | 3-I | H | $C(CH_3)_2CH_2SCH_3$ | H | S | 4-Me-2-i-$C_3F_7$ | |
| Q10 | 10-29 | 3-I | H | $C(CH_3)_2CH_2SOCH_3$ | H | S | 4-Me-2-i-$C_3F_7$ | |
| Q10 | 10-30 | 3-I | H | $C(CH_3)_2CH_2SO_2CH_3$ | H | S | 4-Me-2-i-$C_3F_7$ | |
| Q10 | 10-31 | 3-I | H | $CH(CH_3)CH_2NHAc$ | H | S | 4-Me-2-i-$C_3F_7$ | |
| Q10 | 10-32 | 3-I | H | $C(CH_3)_2CH_2NHAc$ | H | S | 4-Me-2-i-$C_3F_7$ | |
| Q10 | 10-33 | 3-I | Et | Et | H | O | H | |
| Q10 | 10-34 | 3-I | Et | Et | H | O | 4-Me-2-$C_2F_5$ | |
| Q10 | 10-35 | 3-I | Et | Et | H | O | 4-Me-2-n-$C_3F_7$ | |
| Q10 | 10-36 | 3-I | Et | Et | H | O | 4-Me-2-i-$C_3F_7$ | |
| Q10 | 10-37 | 3-I | Et | Et | H | O | 2-Cl | |
| Q10 | 10-38 | 3-I | Et | Et | H | O | 2-Br | |
| Q10 | 10-39 | 3-I | Et | Et | H | O | 2-n-$C_3F_7$ | |
| Q10 | 10-40 | 3-$CF_3$ | H | i-Pr | H | NMe | 4-Me-2-$C_2F_5$ | |
| Q10 | 10-41 | 3-Ph | H | i-Pr | H | NMe | 4-Me-2-n-$C_3F_7$ | |
| Q10 | 10-42 | 3-$SOCF_3$ | H | i-Pr | H | NMe | 4-Me-2-i-$C_3F_7$ | |
| Q10 | 10-43 | 3-$C_2F_5$ | H | i-Pr | H | NMe | 4-Me-2-$C_2F_5$ | |
| Q10 | 10-44 | 3-I-4-Cl | H | i-Pr | H | NMe | 4-Me-2-n-$C_3F_7$ | |
| Q10 | 10-45 | 3-I-4-$CF_3$ | H | i-Pr | H | S | 4-Me-2-i-$C_3F_7$ | |
| Q10 | 10-46 | 3-$F_3$-4-Cl | H | i-Pr | H | S | 4-Me-2-$C_2F_5$ | |
| Q10 | 10-47 | 3-$OCF_2O$-4 | H | i-Pr | H | S | 4-Me-2-n-$C_3F_7$ | |
| Q10 | 10-48 | 3-$OCF_2CF_2O$-4 | H | i-Pr | H | S | 4-Me-2-i-$C_3F_7$ | |

TABLE 5

Q: [structure Q13: triazole ring with positions labeled N2-N3-C4(Ym)-C5(Me)-W1]

Q13

($Z^1 = Z^2 = O$)

| Q | No. | Xn | $R^1$ | $R^2$ | $R^3$ | W | Ym | mp (° C.) |
|---|---|---|---|---|---|---|---|---|
| Q13 | 13-1 | 3-Cl | H | i-Pr | H | S | 4-Me | |
| Q13 | 13-2 | 3-Cl | H | i-Pr | H | O | 4-Me | |
| Q13 | 13-3 | 3-Cl | H | i-Pr | H | NMe | 4-Me | |
| Q13 | 13-4 | 3-I | H | i-Pr | H | S | H | |
| Q13 | 13-5 | 3-I | H | i-Pr | H | S | 4-Me | 60 |
| Q13 | 13-6 | 3-I | H | i-Pr | H | S | 4-Cl | |
| Q13 | 13-7 | 3-I | H | i-Pr | H | S | 4-$CF_3$ | |
| Q13 | 13-8 | 3-I | H | i-Pr | H | S | 4-$C_2F_5$ | |
| Q13 | 13-9 | 3-I | H | i-Pr | H | S | 4-n-$C_3F_7$ | |
| Q13 | 13-10 | 3-I | H | i-Pr | H | S | 4-i-$C_3F_7$ | |
| Q13 | 13-11 | 3-I | H | i-Pr | H | S | 4-t-Bu | |
| Q13 | 13-12 | 6-I | H | i-Pr | H | S | 4-Me | 73 |
| Q13 | 13-13 | 3-I | H | $CH(CH_3)CH_2SCH_3$ | H | S | 4-$CF_3$ | |
| Q13 | 13-14 | 3-I | H | $CH(CH_3)CH_2SOCH_3$ | H | S | 4-$CF_3$ | |
| Q13 | 13-15 | 3-I | H | $CH(CH_3)CH_2SO_2CH_3$ | H | S | 4-$CF_3$ | |
| Q13 | 13-16 | 3-I | H | $C(CH_3)_2CH_2SCH_3$ | H | S | 4-$CF_3$ | |
| Q13 | 13-17 | 3-I | H | $C(CH_3)_2CH_2SOCH_3$ | H | S | 4-$CF_3$ | |
| Q13 | 13-18 | 3-I | H | $C(CH_3)_2CH_2SO_2CH_3$ | H | S | 4-$CF_3$ | |
| Q13 | 13-19 | 3-I | H | $CH(CH_3)CH_2NHAc$ | H | S | 4-$CF_3$ | |
| Q13 | 13-20 | 3-I | H | $C(CH_3)_2CH_2NHAc$ | H | S | 4-$CF_3$ | |
| Q13 | 13-21 | 3-I | H | $CH(CH_3)CH_2CH_2OCH_3$ | H | S | 4-$CF_3$ | |
| Q13 | 13-22 | 3-I | H | $C(CH_3)_2CH_2CH_2OCH_3$ | H | S | 4-$CF_3$ | |
| Q13 | 13-23 | 3-I | Et | Et | H | S | H | |
| Q13 | 13-24 | 3-I | Et | Et | H | S | 4-$CF_3$ | |
| Q13 | 13-25 | 3-I | Et | Et | H | S | 4-$CF_3$ | |
| Q13 | 13-26 | 3-I | Et | Et | H | S | 4-$CF_3$ | |
| Q13 | 13-27 | 3-I | Et | Et | H | S | 4-$CF_3$ | |
| Q13 | 13-28 | 3-$CF_3$ | H | i-Pr | H | S | 3-$C_2F_5$ | |
| Q13 | 13-29 | 3-Ph | H | i-Pr | H | S | 3-n-$C_3F_7$ | |
| Q13 | 13-30 | 3-$SOCF_3$ | H | i-Pr | H | S | 3-i-$C_3F_7$ | |
| Q13 | 13-31 | 3-$C_2F_5$ | H | i-Pr | H | S | 3-$C_2F_5$ | |
| Q13 | 13-32 | 3-I-4-Cl | H | i-Pr | H | S | 3-n-$C_3F_7$ | |
| Q13 | 13-33 | 3-I-4-$CF_3$ | H | i-Pr | H | S | 3-i-$C_3F_7$ | |
| Q13 | 13-34 | 3-$CF_3$-4-Cl | H | i-Pr | H | S | 3-$C_2F_5$ | |
| Q13 | 13-35 | 3-$OCF_2$O-4 | H | i-Pr | H | S | 3-n-$C_3F_7$ | |
| Q13 | 13-36 | 3-$OCF_2CF_2$O-4 | H | i-Pr | H | S | 3-i-$C_3F_7$ | |

TABLE 6

Q: [structure Q19: thiadiazole-type ring with positions N3-N4-C5(Ym)-W1-C2]

Q19

($Z^1 = Z^2 = O$)

| Q | No. | Xn | $R^1$ | $R^2$ | $R^3$ | W | Ym | mp (° C.) |
|---|---|---|---|---|---|---|---|---|
| Q19 | 19-1 | 3-Cl | H | i-Pr | H | O | H | |
| Q19 | 19-2 | 3-Cl | H | i-Pr | H | O | 5-$C_2F_5$ | |
| Q19 | 19-3 | 3-Cl | H | i-Pr | H | S | 5-Me | 166 |
| Q19 | 19-4 | 3-Br | H | i-Pr | H | O | 5-n-$C_3F_7$ | |
| Q19 | 19-5 | 3-$NO_2$ | H | i-Pr | H | O | 5-i-$C_3F_7$ | |
| Q19 | 19-6 | 3-I | H | i-Pr | H | S | H | |
| Q19 | 19-7 | 3-I | H | i-Pr | H | S | 5-Me | |
| Q19 | 19-8 | 3-I | H | i-Pr | H | S | 5-Cl | |
| Q19 | 19-9 | 3-I | H | i-Pr | H | S | 5-$CF_3$ | 104 |
| Q19 | 19-10 | 3-I | H | i-Pr | H | S | 5-$C_2F_5$ | |
| Q19 | 19-11 | 3-I | H | i-Pr | H | S | 5-n-$C_3F_7$ | |

TABLE 6-continued

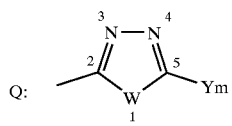

Q19

($Z^1 = Z^2 = O$)

| Q | No. | Xn | $R^1$ | $R^2$ | $R^3$ | W | Ym | mp (° C.) |
|---|---|---|---|---|---|---|---|---|
| Q19 | 19-12 | 3-I | H | i-Pr | H | S | 5-i-$C_3F_7$ | |
| Q19 | 19-13 | 3-I | H | i-Pr | H | S | 5-t-Bu | |
| Q19 | 19-14 | 3-I | H | i-Pr | H | S | 5-$CF_3$ | 176 |
| Q19 | 19-15 | 3-I | H | t-Bu | H | NMe | 5-i-$C_3F_7$ | |
| Q19 | 19-16 | 3-I | H | t-Bu | H | NMe | 5-$C_2F_5$ | |
| Q19 | 19-17 | 3-I | H | t-Bu | H | NMe | 5-n-$C_3F_7$ | |
| Q19 | 19-18 | 3-I | H | t-Bu | H | NMe | 5-$CF_3$ | |
| Q19 | 19-19 | 3-I | H | $CH(CH_3)CH_2SCH_3$ | H | S | 5-i-$C_3F_7$ | |
| Q19 | 19-20 | 3-I | H | $CH(CH_3)CH_2SOCH_3$ | H | S | 5-i-$C_3F_7$ | |
| Q19 | 19-21 | 3-I | H | $CH(CH_3)CH_2SO_2CH_3$ | H | S | 5-i-$C_3F_7$ | |
| Q19 | 19-22 | 3-I | H | $C(CH_3)_2CH_2SCH_3$ | H | S | 5-i-$C_3F_7$ | |
| Q19 | 19-23 | 3-I | H | $C(CH_3)_2CH_2SOCH_3$ | H | S | 5-i-$C_3F_7$ | |
| Q19 | 19-24 | 3-I | H | $C(CH_3)_2CH_2SO_2CH_3$ | H | S | 5-i-$C_3F_7$ | |
| Q19 | 19-25 | 3-I | H | $CH(CH_3)CH_2NHAc$ | H | S | 5-i-$C_3F_7$ | |
| Q19 | 19-26 | 3-I | H | $C(CH_3)_2CH_2NHAc$ | H | S | 5-i-$C_3F_7$ | |
| Q19 | 19-27 | 3-I | H | $CH(CH_3)CH_2CH_2OCH_3$ | H | S | 5-i-$C_3F_7$ | |
| Q19 | 19-28 | 3-I | H | $C(CH_3)_2CH_2CH_2OCH_3$ | H | S | 5-i-$C_3F_7$ | |
| Q19 | 19-29 | 3-I | Et | Et | H | O | H | |
| Q19 | 19-30 | 3-I | Et | Et | H | O | 5-$C_2F_5$ | |
| Q19 | 19-31 | 3-I | Et | Et | H | O | 5-n-$C_3F_7$ | |
| Q19 | 19-32 | 3-I | Et | Et | H | O | 5-i-$C_3F_7$ | |
| Q19 | 19-33 | 3-I | Et | Et | H | O | 5-Cl | |
| Q19 | 19-34 | 3-I | Et | Et | H | S | 5-t-Bu | 59 |
| Q19 | 19-35 | 3-$CF_3$ | H | i-Pr | H | NMe | 5-$C_2F_5$ | |
| Q19 | 19-36 | 3-Ph | H | i-Pr | H | NMe | 5-n-$C_3F_7$ | |
| Q19 | 19-37 | 3-$SOCF_3$ | H | i-Pr | H | NMe | 5-i-$C_3F_7$ | |
| Q19 | 19-38 | 3-$C_2F_5$ | H | i-Pr | H | NMe | 5-$C_2F_5$ | |
| Q19 | 19-39 | 3-I-4-Cl | H | i-Pr | H | NMe | 5-n-$C_3F_7$ | |
| Q19 | 19-40 | 3-I-4-$CF_3$ | H | i-Pr | H | S | 5-i-$C_3F_7$ | |
| Q19 | 19-41 | 3-$CF_3$-4-Cl | H | i-Pr | H | S | 5-$C_2F_5$ | |
| Q19 | 19-42 | 3-$OCF_2$O-4 | H | i-Pr | H | S | 5-n-$C_3F_7$ | |
| Q19 | 19-43 | 3-$OCF_2CF_2$O-4 | H | i-Pr | H | S | 5-i-$C_3F_7$ | |

TABLE 7

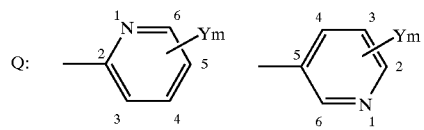

Q26　　Q27

($Z^1 = Z^2 = O$)

| Q | No. | Xn | $R^1$ | $R^2$ | $R^3$ | Ym | mp (° C.) |
|---|---|---|---|---|---|---|---|
| Q26 | 26-1 | H | H | i-Pr | H | 3-Cl-5-$CF_3$ | 85 |
| Q26 | 26-2 | 3-Cl | H | i-Pr | H | H | |
| Q26 | 26-3 | 3-Cl | H | i-Pr | H | 3-Me-5-$C_2F_5$ | |
| Q26 | 26-4 | 3-Br | H | i-Pr | H | 3-Me-5-n-$C_3F_7$ | |
| Q26 | 26-5 | 3-$NO_2$ | H | i-Pr | H | 3-Me-5-i-$C_3F_7$ | |
| Q26 | 26-6 | 3-I | H | i-Pr | H | 5-$C_2F_5$ | |
| Q26 | 26-7 | 3-I | H | i-Pr | H | 5-n-$C_3F_7$ | |
| Q26 | 26-8 | 3-I | H | i-Pr | H | 5-i-$C_3F_7$ | |
| Q26 | 26-9 | 3-I | H | i-Pr | H | 3-Me-5-$C_2F_5$ | |
| Q26 | 26-10 | 3-I | H | i-Pr | H | 3-Me-5-n-$C_3F_7$ | |
| Q26 | 26-11 | 3-I | H | i-Pr | H | 3-Me-5-i-$C_3F_7$ | 140 |
| Q26 | 26-12 | 3-I | H | i-Pr | H | 3-Me-4-$C_2F_5$ | |
| Q26 | 26-13 | 3-I | H | i-Pr | H | 3-Me-4-n-$C_3F_7$ | |
| Q26 | 26-14 | 3-I | H | i-Pr | H | 3-Me-4-i-$C_3F_7$ | |
| Q26 | 26-15 | 3-I | H | t-Bu | H | 5-i-$C_3F_7$ | |

TABLE 7-continued

Q: Q26 (pyridine with N at position 1, methyl at 2, Ym at 5/6 region) / Q27 (pyridine with N at position 1, methyl at 5, Ym at 2/3 region)

($Z^1 = Z^2 = O$)

| Q | No. | Xn | $R^1$ | $R^2$ | $R^3$ | Ym | mp (° C.) |
|---|---|---|---|---|---|---|---|
| Q26 | 26-16 | 3-I | H | t-Bu | H | 5-$C_2F_5$ | |
| Q26 | 26-17 | 3-I | H | t-Bu | H | 5-n-$C_3F_7$ | |
| Q26 | 26-18 | 3-I | H | t-Bu | H | 3-Me-5-i-$C_3F_7$ | |
| Q26 | 26-19 | 3-I | H | CH(CH$_3$)CH$_2$SCH$_3$ | H | 3-Me-5-i-$C_3F_7$ | |
| Q26 | 26-20 | 3-I | H | CH(CH$_3$)CH$_2$SOCH$_3$ | H | 3-Me-5-i-$C_3F_7$ | |
| Q26 | 26-21 | 3-I | H | CH(CH$_3$)CH$_2$SO$_2$CH$_3$ | H | 3-Me-5-i-$C_3F_7$ | |
| Q26 | 26-22 | 3-I | H | C(CH$_3$)$_2$CH$_2$SCH$_3$ | H | 3-Me-5-i-$C_3F_7$ | |
| Q26 | 26-23 | 3-I | H | C(CH$_3$)$_2$CH$_2$SOCH$_3$ | H | 3-Me-5-i-$C_3F_7$ | |
| Q26 | 26-24 | 3-I | H | C(CH$_3$)$_2$CH$_2$SO$_2$CH$_3$ | H | 3-Me-5-i-$C_3F_7$ | |
| Q26 | 26-25 | 3-I | H | CH(CH$_3$)CH$_2$SEt | H | 3-Me-5-i-$C_3F_7$ | |
| Q26 | 26-26 | 3-I | H | C(CH$_3$)$_2$CH$_2$SEt | H | 3-Me-5-i-$C_3F_7$ | |
| Q26 | 26-27 | 3-I | H | CH(CH$_3$)CH$_2$CH$_2$SCH$_3$ | H | 3-Me-5-i-$C_3F_7$ | |
| Q26 | 26-28 | 3-I | H | CH(CH$_3$)$_2$CH$_2$CH$_2$SCH$_3$ | H | 3-Me-5-i-$C_3F_7$ | |
| Q26 | 26-29 | 3-I | Et | Et | H | 3-Me-5-$C_2F_5$ | Paste |
| Q26 | 26-30 | 3-I | Et | Et | H | 3-Me-5-n-$C_3F_7$ | Paste |
| Q26 | 26-31 | 3-I | Et | Et | H | 3-Me-5-i-$C_3F_7$ | 159 |
| Q26 | 26-32 | 3-I | Et | Et | H | 5-Cl | 127 |
| Q26 | 26-33 | 3-I | Et | Et | H | 5-Br | 154 |
| Q26 | 26-34 | 3-$CF_3$ | H | i-Pr | H | 3-Me-5-$C_2F_5$ | |
| Q26 | 26-35 | 3-Ph | H | i-Pr | H | 3-Me-5-n-$C_3F_7$ | |
| Q26 | 26-36 | 3-SOCF$_3$ | H | i-Pr | H | 3-Me-5-i-$C_3F_7$ | |
| Q26 | 26-37 | 3-$C_2F_5$ | H | i-Pr | H | 3-Me-5-$C_2F_5$ | |
| Q26 | 26-38 | 3-I-4-Cl | H | i-Pr | H | 3-Me-5-n-$C_3F_7$ | |
| Q26 | 26-39 | 3-I-4-$CF_3$ | H | i-Pr | H | 3-Me-5-i-$C_3F_7$ | |
| Q26 | 26-40 | 3-$CF_3$-4-Cl | H | i-Pr | H | 3-Me-5-$C_2F_5$ | |
| Q26 | 26-41 | 3-OCF$_2$O-4 | H | i-Pr | H | 3-Me-5-n-$C_3F_7$ | |
| Q26 | 26-42 | 3-OCF$_2$CF$_2$O-4 | H | i-Pr | H | 3-Me-5-i-$C_3F_7$ | |
| Q26 | 26-43 | 3-I | H | i-Pr | H | 3-Me-5-i-$C_3F_7$ | 140 |
| Q27 | 27-1 | H | H | i-Pr | H | H | 139 |
| Q27 | 27-2 | H | H | i-Pr | H | 2-Me | |
| Q27 | 27-3 | H | H | i-Pr | H | 3-Me | |
| Q27 | 27-4 | H | H | i-Pr | H | 4-Me | |
| Q27 | 27-5 | H | H | i-Pr | H | 6-Me | |
| Q27 | 27-6 | H | H | i-Pr | H | 2-Cl | |
| Q27 | 27-7 | H | H | i-Pr | H | 3-Cl | |
| Q27 | 27-8 | H | H | i-Pr | H | 4-Cl | |
| Q27 | 27-9 | H | H | i-Pr | H | 6-Cl | |
| Q27 | 27-10 | 3-Cl | H | i-Pr | H | 2-$CF_3$ | |
| Q27 | 27-11 | 3-Cl | H | i-Pr | H | 3-$CF_3$ | |
| Q27 | 27-12 | 3-Cl | H | i-Pr | H | 4-$CF_3$ | |
| Q27 | 27-13 | 3-Cl | H | i-Pr | H | 6-$CF_3$ | |
| Q27 | 27-14 | 3-Cl | H | i-Pr | H | 2-$NO_2$ | |
| Q27 | 27-15 | 3-Cl | H | i-Pr | H | 3-$NO_2$ | |
| Q27 | 27-16 | 3-Cl | H | i-Pr | H | 4-$NO_2$ | |
| Q27 | 27-17 | 3-Cl | H | i-Pr | H | 6-$NO_2$ | |
| Q27 | 27-18 | 3-Cl | H | i-Pr | H | 2-Et | |
| Q27 | 27-19 | 3-Cl | H | i-Pr | H | 2-i-Pr | |
| Q27 | 27-20 | 3-Cl | H | i-Pr | H | 2-t-Bu | |
| Q27 | 27-21 | 3-Cl | H | i-Pr | H | 2-SCH$_3$ | |
| Q27 | 27-22 | 3-Cl | H | i-Pr | H | 2-SOCH$_3$ | |
| Q27 | 27-23 | 3-Cl | H | i-Pr | H | 2-SO$_2$CH$_3$ | |
| Q27 | 27-24 | 3-Cl | H | i-Pr | H | 2-SCF$_3$ | |
| Q27 | 27-25 | 3-Cl | H | i-Pr | H | 2-SCHF$_2$ | |
| Q27 | 27-26 | 3-Cl | H | i-Pr | H | 2-COCH$_3$ | |
| Q27 | 27-27 | 3-Cl | H | i-Pr | H | 2-CN | |
| Q27 | 27-28 | 3-Cl | H | i-Pr | H | 2-OCH$_3$ | |
| Q27 | 27-29 | 3-Cl | H | i-Pr | H | 2-O-(4-Br-Ph) | 101 |
| Q27 | 27-30 | 3-Cl | H | i-Pr | H | 2-O-(2,4-Cl$_2$-Ph) | 97 |
| Q27 | 27-31 | 3-Cl | H | i-Pr | H | 4-S-i-Pr | 193 |
| Q27 | 27-32 | 3-Cl | H | i-Pr | H | 4-S-i-Bu | 183 |
| Q27 | 27-33 | 3-Cl | H | i-Pr | H | 2-OCF$_2$CCl$_2$F | |
| Q27 | 27-34 | 3-Cl | H | i-Pr | H | 2-OCH$_2$CF$_3$ | |
| Q27 | 27-35 | 3-Cl | H | i-Pr | H | 2-OCH$_2$CF$_2$CHF$_2$ | |
| Q27 | 27-36 | 3-Cl | H | i-Pr | H | 2-CF$_2$CF$_3$ | |
| Q27 | 27-37 | 3-Cl | H | i-Pr | H | 2-COOCH(CF$_3$)$_2$ | |
| Q27 | 27-38 | 3-Cl | H | i-Pr | H | 2-Ph | |

TABLE 7-continued

Q:

Q26   Q27

($Z^1 = Z^2 = O$)

| Q | No. | Xn | $R^1$ | $R^2$ | $R^3$ | Ym | mp (° C.) |
|---|---|---|---|---|---|---|---|
| Q27 | 27-39 | 3-Cl | H | n-Bu | H | 2-Cl | |
| Q27 | 27-40 | 3-Cl | H | i-Bu | H | 2-Cl | |
| Q27 | 27-41 | 3-Cl | H | s-Bu | H | 2-Cl | |
| Q27 | 27-42 | 3-Cl | H | t-Bu | H | 2-Cl | |
| Q27 | 27-43 | 3-Cl | H | c-$C_3H_5$ | H | 2-Cl | |
| Q27 | 27-44 | 3-Cl | H | c-$C_4H_7$ | H | 2-Cl | |
| Q27 | 27-45 | 3-Cl | H | c-$C_5H_9$ | H | 2-Cl | |
| Q27 | 27-46 | 3-Cl | H | c-$C_6H_{11}$ | H | 2-Cl | |
| Q27 | 27-47 | 3-Cl | H | $CH_2CH=CH_2$ | H | 2-Cl | |
| Q27 | 27-48 | 3-Cl | H | $CH_2C\equiv CH$ | H | 2-Cl | |
| Q27 | 27-49 | 3-Cl | H | $CH_2Ph$ | H | 2-Cl | |
| Q27 | 27-50 | 3-Cl | H | $C(CH_3)_2C\equiv CH$ | H | 2-Cl | |
| Q27 | 27-51 | 3-Cl | H | $C(CH_3)_2C\equiv CPh$ | H | 2-Cl | |
| Q27 | 27-52 | 3-Cl | H | $CH_2CH_2SCH_3$ | H | 2-Cl | |
| Q27 | 27-53 | 3-Cl | H | $CH_2CH_2SPh$ | H | 2-Cl | |
| Q27 | 27-54 | 3-Cl | H | $CH_2CH_2SO_2Ph$ | H | 2-Cl | |
| Q27 | 27-55 | 3-Cl | H | $CH_2CH_2SO_2CH_3$ | H | 2-Cl | |
| Q27 | 27-56 | 3-Cl | H | $CH_2CH_2CO_2CH_3$ | H | 2-Cl | |
| Q27 | 27-57 | 3-Cl | H | $CH_2CH_2CONHCH_3$ | H | 2-Cl | |
| Q27 | 27-58 | 3-Cl | Et | Et | H | 2-Cl | |
| Q27 | 27-59 | 3-Cl | n-Pr | n-Pr | H | 2-Cl | |
| Q27 | 27-60 | 3-Cl | i-Pr | i-Pr | H | 2-Cl | |
| Q27 | 27-61 | 3-Cl | i-Pr | Me | H | 2-Cl | |
| Q27 | 27-62 | 3-Cl | i-Bu | Me | H | 2-Cl | |
| Q27 | 27-63 | 3-Cl | $CH_2CH=CH_2$ | $CH_2CH=CH_2$ | H | 2-Cl | |
| Q27 | 27-64 | 3-Cl | Et | Et | Me | 2-Cl | |
| Q27 | 27-65 | 3-Cl | n-Pr | i-Pr | Me | 2-Cl | |
| Q27 | 27-66 | 3-Cl | i-Pr | i-Pr | Me | 2-Cl | |
| Q27 | 27-67 | 3-Cl | Et | Et | Ac | 2-Cl | |
| Q27 | 27-68 | 3-Cl | n-Pr | i-Pr | Ac | 2-Cl | |
| Q27 | 27-69 | 3-Cl | i-Pr | i-Pr | Ac | 2-Cl | |
| Q27 | 27-70 | 3-Cl | —$(CH_2)_4$— | | H | 2-Cl | |
| Q27 | 27-71 | 3-Cl | —$(CH_2)_2O(CH_2)_2$— | | H | 2-Cl | |
| Q27 | 27-72 | 3-Cl | i-Pr | $SO_2CH_3$ | H | 2-Cl | |
| Q27 | 27-73 | 3-Cl | i-Pr | CN | H | 2-Cl | |
| Q27 | 27-74 | 3-Cl | i-Pr | $CO_2CH_3$ | H | 2-Cl | |
| Q27 | 27-75 | 3-Cl | i-Pr | $COCH_3$ | H | 2-Cl | |
| Q27 | 27-76 | 3-Cl | i-Pr | COPh | H | 2-Cl | |
| Q27 | 27-77 | 3-Cl | i-Pr | $NHCOCH_3$ | H | 2-Cl | |
| Q27 | 27-78 | 3-Cl | H | i-Pr | H | 2,4-$Me_2$ | |
| Q27 | 27-79 | 3-Cl | H | i-Pr | H | 2,4-$Cl_2$ | |
| Q27 | 27-80 | 3-Cl | H | i-Pr | H | 4,6-$Me_2$ | |
| Q27 | 27-81 | 3-Cl | H | i-Pr | H | 4-Me-2-Cl | 211 |
| Q27 | 27-82 | 3-Cl | H | i-Pr | H | 4-Me-2-F | |
| Q27 | 27-83 | 3-Cl | H | i-Pr | H | 4-Me-2-Br | |
| Q27 | 27-84 | 3-Cl | H | i-Pr | H | 4-Me-2-I | |
| Q27 | 27-85 | 3-Cl | H | i-Pr | H | 4-Me-2-$OCHF_2$ | |
| Q27 | 27-86 | 3-Cl | H | i-Pr | H | 4-Me-2-$OCF_3$ | |
| Q27 | 27-87 | 3-Cl | H | i-Pr | H | 4-Me-2-$NO_2$ | |
| Q27 | 27-88 | 3-Cl | H | i-Pr | H | 4-Me-2-$NMe_2$ | |
| Q27 | 27-89 | 3-Cl | H | i-Pr | H | 4-Me-2-C$\equiv$CH | |
| Q27 | 27-90 | 3-Cl | H | i-Pr | H | 4-Me-2-C$\equiv$C-t-Bu | |
| Q27 | 27-91 | 3-Cl | H | i-Pr | H | 4-Me-2-C$\equiv$CPh | |
| Q27 | 27-92 | 3-Cl | H | i-Pr | H | 4-Me-2-$CF_2CF_3$ | |
| Q27 | 27-93 | 3-Cl | H | i-Pr | H | 4-Me-2-i-$C_3F_7$ | |
| Q27 | 27-94 | 3-Cl | H | i-Pr | H | 4-Me-2-n-$C_3F_7$ | |
| Q27 | 27-95 | 3-Cl | H | i-Pr | H | 4-Me-2-$OCH_2OCH_3$ | |
| Q27 | 27-96 | 3-Cl | H | i-Pr | H | 4-Me-2-$OCF_2CHF_2$ | |
| Q27 | 27-97 | 3-Cl | H | i-Pr | H | 4-Me-2-OPh | |
| Q27 | 27-98 | 3-Cl | H | i-Pr | H | 4-Me-2-O-(4-Br-Ph) | 79 |
| Q27 | 27-99 | 3-Cl | H | i-Pr | H | 4-Me-2-$OSO_2Ph$ | |
| Q27 | 27-100 | 3-Cl | H | i-Pr | H | 4-Me-2-$OCH_2CO_2CH_3$ | |
| Q27 | 27-101 | 3-Cl | H | i-Pr | H | 4-Me-2-$CO_2CH_3$ | |
| Q27 | 27-102 | 3-Cl | H | i-Pr | H | 4-Me-2-S-i-Pr | |
| Q27 | 27-103 | 3-Cl | H | i-Pr | H | 4-Me-2-$SCHF_2$ | |
| Q27 | 27-104 | 3-Cl | H | i-Pr | H | 4-Me-2-$SOCHF_2$ | |

TABLE 7-continued

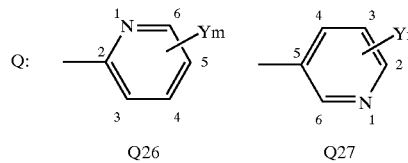

Q26        Q27

$(Z^1 = Z^2 = O)$

| Q | No. | Xn | R$^1$ | R$^2$ | R$^3$ | Ym | mp (° C.) |
|---|---|---|---|---|---|---|---|
| Q27 | 27-105 | 3-Cl | H | i-Pr | H | 4-Me-2-SO$_2$CHF$_2$ | |
| Q27 | 27-106 | 3-Cl | H | i-Pr | H | 4-Cl-2-CF$_3$ | |
| Q27 | 27-107 | 3-Cl | H | i-Pr | H | 4-Cl-2-OCF$_3$ | |
| Q27 | 27-108 | 3-Cl | H | i-Pr | H | 4-Cl-2-i-C$_3$F$_7$ | |
| Q27 | 27-109 | 3-Cl | H | i-Pr | H | 4-Cl-2-C$_2$F$_5$ | |
| Q27 | 27-110 | 3-Cl | H | i-Pr | H | 4-Cl-2-OCHF$_2$ | |
| Q27 | 27-111 | 3-Cl | H | i-Pr | H | 4-Cl-2-OSO$_2$Ph | |
| Q27 | 27-112 | 3-Cl | H | i-Pr | H | 4-OCH$_3$-2-Ph | |
| Q27 | 27-113 | 3-Cl | H | i-Pr | H | 4-CF$_3$-2-Cl | |
| Q27 | 27-114 | 3-Cl | H | i-Pr | H | 4-Me-3-CF$_3$ | |
| Q27 | 27-115 | 3-Cl | H | i-Pr | H | 4-Me-3-Cl | |
| Q27 | 27-116 | 3-Cl | H | i-Pr | H | 4-Me-3-OCF$_3$ | |
| Q27 | 27-117 | 3-Cl | H | i-Pr | H | 4-Me-3-CF$_2$CF$_3$ | |
| Q27 | 27-118 | 3-Cl | H | i-Pr | H | 4-Me-3-n-C$_3$F$_7$ | |
| Q27 | 27-119 | 3-Cl | H | i-Pr | H | 4-Me-3-i-C$_3$F$_7$ | |
| Q27 | 27-120 | 3-Cl | H | i-Pr | H | 3,4-Me$_2$-2-Cl | |
| Q27 | 27-121 | 3-Cl | H | i-Pr | H | 3,4-Me$_2$-2-OMe | |
| Q27 | 27-122 | 3-Cl | H | i-Pr | H | 3,4-Me$_2$-2-SMe | |
| Q27 | 27-123 | 3-Cl | H | i-Pr | H | 4-Me-2,3-Cl$_2$ | |
| Q27 | 27-124 | 6-Cl | H | i-Pr | H | 2-O-(4-Br-Ph) | 170 |
| Q27 | 27-125 | 6-Cl | H | i-Pr | H | 2-O-(2,4-Cl$_2$-Ph) | 189 |
| Q27 | 27-126 | 6-Cl | H | i-Pr | H | 2-S-i-Pr | 120 |
| Q27 | 27-127 | 6-Cl | H | i-Pr | H | 2-S-i-Bu | 187 |
| Q27 | 27-128 | 6-Cl | H | i-Pr | H | 4-Me-2-Cl | 230 |
| Q27 | 27-129 | 3-I | Et | Et | H | 6-Cl-2-n-C$_3$F$_7$ | 122 |
| Q27 | 27-130 | 3-I | Et | Et | H | 2-Cl | 203 |
| Q27 | 27-131 | 3-I | Et | Et | H | 2-n-C$_3$F$_7$ | 200 |
| Q27 | 27-132 | 3-I | Et | Et | H | 2-O-(4-Br-Ph) | 247 |
| Q27 | 27-133 | 3-I | H | i-Pr | H | 2-Cl | 215 |
| Q27 | 27-134 | 3-I | H | i-Pr | H | 2-C$_2$F$_5$ | Amorphous solid |
| Q27 | 27-135 | 3-I | H | i-Pr | H | 2-n-C$_3$F$_7$ | 200 |
| Q27 | 27-136 | 3-I | H | i-Pr | H | 2-i-C$_3$F$_7$ | 270 |
| Q27 | 27-137 | 3-I | H | i-Pr | H | 4-Me-2-i-C$_3$F$_7$ | 257 |
| Q27 | 27-138 | 3-I | H | i-Pr | H | 6-Me-2-i-C$_3$F$_7$ | 234 |
| Q27 | 27-139 | 3-I | H | t-Bu | H | 2-i-C$_3$F$_7$ | 275 |
| Q27 | 27-140 | 3-I | H | t-Bu | H | 2-C$_2$F$_5$ | 260 |
| Q27 | 27-141 | 3-I | H | t-Bu | H | 2-n-C$_3$F$_7$ | 245 |
| Q27 | 27-142 | 3-I | H | t-Bu | H | 4-Me-2-i-C$_3$F$_7$ | 250 |
| Q27 | 27-143 | 3-I | H | t-Bu | H | 6-Me-2-i-C$_3$F$_7$ | 246 |
| Q27 | 27-144 | 3-I | H | CH(CH$_3$)CH$_2$SCH$_3$ | H | 4-Me-2-i-C$_3$F$_7$ | 225 |
| Q27 | 27-145 | 3-I | H | CH(CH$_3$)CH$_2$SCH$_3$ | H | 6-Me-2-i-C$_3$F$_7$ | 229 |
| Q27 | 27-146 | 3-I | H | CH(CH$_3$)CH$_2$SOCH$_3$ | H | 4-Me-2-i-C$_3$F$_7$ | |
| Q27 | 27-147 | 3-I | H | CH(CH$_3$)CH$_2$SOCH$_3$ | H | 6-Me-2-i-C$_3$F$_7$ | |
| Q27 | 27-148 | 3-I | H | CH(CH$_3$)CH$_2$SO$_2$CH$_3$ | H | 4-Me-2-i-C$_3$F$_7$ | |
| Q27 | 27-149 | 3-I | H | CH(CH$_3$)CH$_2$SO$_2$CH$_3$ | H | 6-Me-2-i-C$_3$F$_7$ | |
| Q27 | 27-150 | 3-I | H | C(CH$_3$)$_2$CH$_2$SCH$_3$ | H | 4-Me-2-i-C$_3$F$_7$ | 173 |
| Q27 | 27-151 | 3-I | H | C(CH$_3$)$_2$CH$_2$SCH$_3$ | H | 6-Me-2-i-C$_2$F$_5$ | 213 |
| Q27 | 27-152 | 3-I | H | C(CH$_3$)$_2$CH$_2$SOCH$_3$ | H | 4-Me-2-i-C$_3$F$_7$ | |
| Q27 | 27-153 | 3-I | H | C(CH$_3$)$_2$CH$_2$SOCH$_3$ | H | 6-Me-2-i-C$_3$F$_7$ | Amorphous |
| Q27 | 27-154 | 3-I | H | C(CH$_3$)$_2$CH$_2$SO$_2$CH$_3$ | H | 4-Me-2-i-C$_3$F$_7$ | |
| Q27 | 27-155 | 3-I | H | C(CH$_3$)$_2$CH$_2$SO$_2$CH$_3$ | H | 6-Me-2-i-C$_3$F$_7$ | |
| Q27 | 27-156 | 3-I | H | i-Pr | H | 4-Me-2-i-C$_3$F$_7$ | |
| Q27 | 27-157 | 3-I | H | t-Bu | H | 6-Me-2-i-C$_3$F$_7$ | |
| Q27 | 27-158 | 3-F | H | C(CH$_3$)$_2$CH$_2$SCH$_3$ | H | 4-Me-2-i-C$_3$F$_7$ | |
| Q27 | 27-159 | 3-F | H | C(CH$_3$)$_2$CH$_2$SCH$_3$ | H | 6-Me-2-i-C$_3$F$_7$ | |
| Q27 | 27-160 | 3-Br | H | i-Pr | H | 4-Me-2-i-C$_3$F$_7$ | |
| Q27 | 27-161 | 3-Br | H | t-Bu | H | 6-Me-2-i-C$_3$F$_7$ | |
| Q27 | 27-162 | 3-Br | H | CH(CH$_3$)CH$_2$SCH$_3$ | H | 4-Me-2-i-C$_3$F$_7$ | |
| Q27 | 27-163 | 3-Br | H | C(CH$_3$)$_2$CH$_2$SCH$_3$ | H | 6-Me-2-i-C$_3$F$_7$ | |
| Q27 | 27-164 | 3-NO$_2$ | H | i-Pr | H | H | 209 |
| Q27 | 27-165 | 3-NO$_2$ | H | i-Pr | H | 4-Me-2-CF$_2$CF$_3$ | |
| Q27 | 27-166 | 3-NO$_2$ | H | i-Pr | H | 4-Me-2-n-C$_3$F$_7$ | |
| Q27 | 27-167 | 3-NO$_2$ | H | i-Pr | H | 4-Me-2-i-C$_3$F$_7$ | |
| Q27 | 27-168 | 3-NO$_2$ | H | i-Pr | H | 6-Me-2-CF$_2$CF$_3$ | |
| Q27 | 27-169 | 3-NO$_2$ | H | i-Pr | H | 6-Me-2-n-C$_3$F$_7$ | |
| Q27 | 27-170 | 3-NO$_2$ | H | i-Pr | H | 6-Me-2-i-C$_3$F$_7$ | |

TABLE 7-continued

Q: [Q26: pyridine structure with N at position 1, numbered 1-6, with methyl and Ym substituents] [Q27: pyridine structure with N at position 1, numbered 1-6, with methyl and Ym substituents]

$(Z^1 = Z^2 = O)$

| Q | No. | Xn | R$^1$ | R$^2$ | R$^3$ | Ym | mp (° C.) |
|---|---|---|---|---|---|---|---|
| Q27 | 27-171 | 3-NO$_2$ | H | i-Pr | H | 4-Me-2-Cl | |
| Q27 | 27-172 | 3-CN | Et | Et | H | 4-Me-2-CF$_2$CF$_3$ | |
| Q27 | 27-173 | 3-CN | Et | Et | H | 4-Me-2-n-C$_3$F$_7$ | |
| Q27 | 27-174 | 3-CN | Et | Et | H | 4-Me-2-i-C$_3$F$_7$ | |
| Q27 | 27-175 | 3-CN | Et | Et | H | 6-Me-2-CF$_2$CF$_3$ | |
| Q27 | 27-176 | 3-CN | Et | Et | H | 6-Me-2-n-C$_3$F$_7$ | |
| Q27 | 27-177 | 3-CN | Et | Et | H | 6-Me-2-i-C$_3$F$_7$ | |
| Q27 | 27-178 | 3-CN | Et | Et | H | 4-Me-2-Cl | |
| Q27 | 27-179 | 3-CF$_3$ | H | i-Pr | H | 4-Me-2-CF$_2$CF$_3$ | |
| Q27 | 27-180 | 3-CF$_3$ | H | i-Pr | H | 6-Me-2-n-C$_3$F$_7$ | |
| Q27 | 27-181 | 3-OCH$_3$ | H | i-Pr | H | 4-Me-2-i-C$_3$F$_7$ | |
| Q27 | 27-182 | 3-OCH$_3$ | H | i-Pr | H | 6-Me-2-CF$_2$CF$_3$ | |
| Q27 | 27-183 | 3-OCH$_3$ | H | i-Pr | H | 4-Me-2-n-C$_3$F$_7$ | |
| Q27 | 27-184 | 3-OCH$_3$ | H | i-Pr | H | 6-Me-2-i-C$_3$F$_7$ | |
| Q27 | 27-185 | 3-SCH$_3$ | H | i-Pr | H | 4-Me-2-CF$_2$CF$_3$ | |
| Q27 | 27-186 | 3-SCH$_3$ | H | i-Pr | H | 6-Me-2-n-C$_3$F$_7$ | |
| Q27 | 27-187 | 3-S-i-Pr | H | i-Pr | H | 4-Me-2-i-C$_3$F$_7$ | |
| Q27 | 27-188 | 3-S-i-Pr | H | i-Pr | H | 6-Me-2-CF$_2$CF$_3$ | |
| Q27 | 27-189 | 3-SOCH$_3$ | H | i-Pr | H | 4-Me-2-n-C$_3$F$_7$ | |
| Q27 | 27-190 | 3-SOCH$_3$ | H | i-Pr | H | 6-Me-2-i-C$_3$F$_7$ | |
| Q27 | 27-191 | 3-SO$_2$CH$_3$ | H | i-Pr | H | 4-Me-2-CF$_2$CF$_3$ | |
| Q27 | 27-192 | 3-SO$_2$CH$_3$ | H | i-Pr | H | 6-Me-2-n-C$_3$F$_7$ | |
| Q27 | 27-193 | 3-SCH$_2$CF$_3$ | H | i-Pr | H | 4-Me-2-i-C$_3$F$_7$ | |
| Q27 | 27-194 | 3-SCF$_3$ | H | i-Pr | H | 4-Me-2-CF$_2$CF$_3$ | |
| Q27 | 27-195 | 3-SOCF$_3$ | H | i-Pr | H | 4-Me-2-n-C$_3$F$_7$ | |
| Q27 | 27-196 | 3-SO$_2$CF3 | H | i-Pr | H | 4-Me-2-i-C$_3$F$_7$ | |
| Q27 | 27-197 | 3-SPh | H | i-Pr | H | 6-Me-2-CF$_2$CF$_3$ | |
| Q27 | 27-198 | 3-SOPh | H | i-Pr | H | 6-Me-2-n-C$_3$F$_7$ | |
| Q27 | 27-199 | 3-SO$_2$Ph | H | i-Pr | H | 6-Me-2-i-C$_3$F$_7$ | |
| Q27 | 27-200 | 3-OPh | H | i-Pr | H | 4-Me-2-CF$_2$CF$_3$ | |
| Q27 | 27-201 | 3-Ph | H | i-Pr | H | 4-Me-2-i-C$_3$F$_7$ | |
| Q27 | 27-202 | 3-C≡CH | H | i-Pr | H | 4-Me-2-i-C$_3$F$_7$ | |
| Q27 | 27-203 | 3-C≡C-t-Bu | H | i-Pr | H | 4-Me-2-i-C$_3$F$_7$ | |
| Q27 | 27-204 | 3-C≡CPh | H | i-Pr | H | 4-Me-2-i-C$_3$F$_7$ | |
| Q27 | 27-205 | 3-C$_2$F$_5$ | H | i-Pr | H | 4-Me-2-i-C$_3$F$_7$ | |
| Q27 | 27-206 | 3-CO$_2$CH$_3$ | H | i-Pr | H | 6-Me-2-i-C$_3$F$_7$ | |
| Q27 | 27-207 | 3-CONHCH$_3$ | H | i-Pr | H | 6-Me-2-i-C$_3$F$_7$ | |
| Q27 | 27-208 | 3-COCH$_3$ | H | i-Pr | H | 6-Me-2-i-C$_3$F$_7$ | |
| Q27 | 27-209 | 3-OCH$_3$(=NOCH$_3$) | H | i-Pr | H | 6-Me-2-i-C$_3$F$_7$ | |
| Q27 | 27-210 | 3,4-Cl$_2$ | H | i-Pr | H | 4-Me-2-i-C$_3$F$_7$ | |
| Q27 | 27-211 | 3,6-Cl$_2$ | H | i-Pr | H | 4-Me-2-n-C$_3$F$_7$ | |
| Q27 | 27-212 | 3,5-Cl$_2$ | H | i-Pr | H | 4-Me-2-i-C$_3$F$_7$ | |
| Q27 | 27-213 | 3,5-Cl$_2$ | H | i-Pr | H | 6-Me-2-CF$_2$CF$_3$ | |
| Q27 | 27-214 | 4,5-Cl$_2$ | H | i-Pr | H | 4-Me-2-n-C$_3$F$_7$ | |
| Q27 | 27-215 | 4,5-Cl$_2$ | H | i-Pr | H | 4-Me-2-i-C$_3$F$_7$ | |
| Q27 | 27-216 | 3-I-4-Cl | H | i-Pr | H | 4-Me-2-CF$_2$CF$_3$ | |
| Q27 | 27-217 | 3-I-4-F | H | i-Pr | H | 4-Me-2-n-C$_3$F$_7$ | |
| Q27 | 27-218 | 3-I-4CF$_3$ | H | i-Pr | H | 4-Me-2-i-C$_3$F$_7$ | |
| Q27 | 27-219 | 3-I-4-OCH$_3$ | H | i-Pr | H | 4-Me-2-CF$_2$CF$_3$ | |
| Q27 | 27-220 | 3-CF$_3$-4-Cl | H | i-Pr | H | 4-Me-2-n-C$_3$F$_7$ | |
| Q27 | 27-221 | 3-CF$_3$-4-OCH$_3$ | H | i-Pr | H | 6-Me-2-i-C$_3$F$_7$ | |
| Q27 | 27-222 | 3-OCH$_2$O-4 | H | i-Pr | H | 6-Me-2-i-C$_3$F$_7$ | |
| Q27 | 27-223 | 3-OCF$_2$O-4 | H | i-Pr | H | 6-Me-2-CF$_2$CF$_3$ | |
| Q27 | 27-224 | 3-OCH$_2$CH$_2$O-4 | H | i-Pr | H | 6-Me-2-n-C$_3$F$_7$ | |
| Q27 | 27-225 | 3-OCF$_2$CF$_2$O-4 | H | i-Pr | H | 6-Me-2-i-C$_3$F$_7$ | |
| Q27 | 27-226 | 3-CH=CH—CH=CH-4 | H | i-Pr | H | 6-Me-2-i-C$_3$F$_7$ | |
| Q27 | 27-227 | 3-I | H | i-Pr | H | 4-Me-3-CF$_2$CF$_3$ | |
| Q27 | 27-228 | 3-I | H | i-Pr | H | 4-Me-3-i-C$_3$F$_7$ | |
| Q27 | 27-229 | 3-I | H | i-Pr | H | 4-Me-3-n-C$_3$F$_7$ | |
| Q27 | 27-230 | 3-I | H | i-Pr | H | 6-Cl-2-i-C$_3$F$_7$ | 188 |
| Q27 | 27-231 | 3-I | Et | Et | H | 6-Cl-2-i-C$_3$F$_7$ | 164 |
| Q27 | 27-232 | 3-I | H | CH(Me)CH$_2$SMe | H | 6-Cl-2-i-C$_3$F$_7$ | 177 |
| Q27 | 27-233 | 3-I | H | C(Me)$_2$CH$_2$SMe | H | 2-i-C$_3$F$_7$ | 229 |
| Q27 | 27-234 | 3-I | H | C(Me)$_2$CH$_2$SMe | H | 6-Cl-2-i-C$_3$F$_7$ | 175 |
| Q27 | 27-235 | 3-I | H | C(Me)$_2$CH$_2$SOMe | H | 6-Cl-2-i-C$_3$F$_7$ | Paste |
| Q27 | 27-236 | 3-I | H | C(Me)$_2$CH$_2$SO$_2$Me | H | 6-Cl-2-i-C$_3$F$_7$ | Amorphous |

TABLE 7-continued

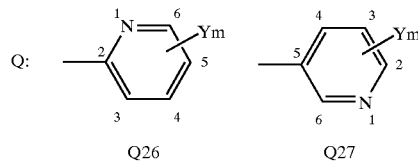

$(Z^1 = Z^2 = O)$

| Q | No. | Xn | R¹ | R² | R³ | Ym | mp (° C.) |
|---|---|---|---|---|---|---|---|
| Q27 | 27-237 | 3-I | H | C(Me)₂CH₂SMe | H | 6-i-C₃F₇ | 183 |
| Q27 | 27-238 | 3-I | H | C(Me)₂CH₂SOMe | H | 6-i-C₃F₇ | Amorphous |
| Q27 | 27-239 | 3-I | H | C(Me)₂CH₂SO₂Me | H | 6-i-C₃F₇ | Amorphous |
| Q27 | 27-240 | 3-I | H | C(Me)₂CH₂SMe | H | 4,6-Cl₂-2-i-C₃F₇ | 120 |
| Q27 | 27-241 | 3-I | H | CH(Me)CH₂SMe | H | 6-MeO-2-i-C₃F₇ | 134 |
| Q27 | 27-242 | 3-I | H | i-Pr | H | 6-MeO-2-i-C₃F₇ | 158 |
| Q27 | 27-243 | 3-I | H | C(Me)₂CH₂SMe | H | 6-Me-2-i-C₃F₇ | 134 |
| Q27 | 27-244 | 3-I | H | C(Me)₂CH₂SOMe | H | 6-Me-2-i-C₃F₇ | Amorphous |
| Q27 | 27-245 | 3-I | H | C(Me)₂CH₂SMe | H | 6-MeS-2-i-C₃F₇ | 179 |
| Q27 | 27-246 | 3-I | H | i-Pr | H | 6-MeS-2-i-C₃F₇ | 219 |
| Q27 | 27-247 | 3-I | H | i-Pr | H | 6-MeSO-2-i-C₃F₇ | Amorphous |
| Q27 | 27-248 | 3-I | H | C(Me)₂CH₂SMe | H | 2-OCHF₂ | 198 |
| Q27 | 27-249 | 3-I | H | C(Me)₂CH₂SO₂Me | H | 2-OCHF₂ | 207 |
| Q27 | 27-250 | 3-I | H | i-Pr | H | 2-OCHF₂ | 205 |
| Q27 | 27-251 | 3-I | H | C(Me)₂CH₂SMe | H | 2-SCHF₂ | 174 |
| Q27 | 27-252 | 3-I | H | i-Pr | H | 2-SCHF₂ | 226 |
| Q27 | 27-253 | 3-I | H | i-Pr | H | 2-SO₂CHF₂ | 230 |
| Q27 | 27-254 | 3-I | H | i-Pr | H | 6-Me-2-OCHF₂ | 252 |
| Q27 | 27-255 | 3-I | H | C(Me)₂CH₂SMe | H | 6-Me-2-OCHF₂ | 124 |
| Q27 | 27-256 | 3-I | H | C(Me)₂CH₂SOMe | H | 6-Me-2-OCHF₂ | 185 |
| Q27 | 27-257 | 3-I | H | C(Me)₂CH₂SO₂Me | H | 6-Me-2-OCHF₂ | 102 |
| Q27 | 27-258 | 3-I | H | i-Pr | H | 6-Me-2-SCHF₂ | 226 |
| Q27 | 27-259 | 3-I | H | C(Me)₂CH₂SMe | H | 6-Me-2-SCHF₂ | 198 |
| Q27 | 27-260 | 3-I | H | i-Pr | H | 6-Me-2-OCH(CF₃)₂ | 266 |
| Q27 | 27-261 | 3-I | H | C(Me)₂CH₂SMe | H | 6-Me-2-OCH(CF₃)₂ | 223 |
| Q27 | 27-262 | 3-I | H | i-Pr | H | 6-Cl-2-OCH(CF₃)₂ | 216 |
| Q27 | 27-263 | 3-I | H | C(Me)₂CH₂SMe | H | 6-Cl-2-OCH(CF₃)₂ | 100 |
| Q27 | 27-264 | 3-I | H | C(Me)₂CH₂SOMe | H | 6-Me-2-OCH(CF₃)₂ | 168 |
| Q27 | 27-265 | 3-I | H | C(Me)₂CH₂SO₂Me | H | 6-Me-2-OCH(CF₃)₂ | 134 |
| Q27 | 27-266 | 3-I | H | C(Me)₂CH₂SOMe | H | 6-Cl-2-OCH(CF₃)₂ | |
| Q27 | 27-267 | 3-I | H | C(Me)₂CH₂SO₂Me | H | 6-Cl-2-OCH(CF₃)₂ | 121 |
| Q27 | 27-268 | 3-I | H | C(Me)₂CH₂SMe | H | 6-OMe-2-OCH(CF₃)₂ | 159 |
| Q27 | 27-269 | 3-I | H | C(Me)₂CH₂SMe | H | 6-F-2-OCH(CF₂)₂ | |
| Q27 | 27-270 | 3-I | H | i-Pr | H | OCH(CF₃)₂ | 240 |
| Q27 | 27-271 | 3-I | H | t-Bu | H | OCH(CF₃)₂ | |
| Q27 | 27-272 | 3-I | H | CH(Me)CH₂SMe | H | OCH(CF₃)₂ | |
| Q27 | 27-273 | 3-I | H | C(Me)₂CH₂SMe | H | OCH(CF₃)₂ | 237 |
| Q27 | 27-274 | 3-I | H | i-Pr | H | 2-Me-6-OCH(CF₃)₂ | 232 |
| Q27 | 27-275 | 3-I | H | C(Me)₂CH₂SMe | H | 2-Me-6-OCH(CF₃)₂ | 171 |
| Q27 | 27-276 | 3-Cl | H | i-Pr | H | 4-Me-2-OCH(CF₃)₂ | 226 |
| Q27 | 27-277 | 3-I | H | i-Pr | H | 4-Me-2-OCH(CF₃)₂ | 248 |
| Q27 | 27-278 | 3-I | H | C(Me)₂CH₂SMe | H | 4-Me-2-OCH(CF₃)₂ | 200 |
| Q27 | 27-279 | 3-I | H | C(Me)₂CH₂SOMe | H | 4-Me-2-OCH(CF₃)₂ | 118 |
| Q27 | 27-280 | 3-I | H | C(Me)₂CH₂SO₂Me | H | 4-Me-2-OCH(CF₃)₂ | 112 |
| Q27 | 27-281 | 3-I | H | CH(Me)CH₂SMe | H | 6-Me-2-OCH(CF₃)₂ | |
| Q27 | 27-282 | 3-I | H | CH(Me)CH₂SEt | H | 6-Me-2-OCH(CF₃)₂ | 256 |
| Q27 | 27-283 | H | H | i-Pr | H | 6-Me-2-OCH(CF₃)₂ | 235 |
| Q27 | 27-284 | H | H | t-Bu | H | 6-Me-2-OCH(CF₃)₂ | 255 |
| Q27 | 27-285 | H | H | CH(Me)CH₂SMe | H | 6-Me-2-OCH(CF₃)₂ | |
| Q27 | 27-286 | H | H | CH(Me)CH₂SOMe | H | 6-Me-2-OCH(CF₃)₂ | |
| Q27 | 27-287 | H | H | CH(Me)CH₂SO₂Me | H | 6-Me-2-OCH(CF₃)₂ | |
| Q27 | 27-288 | H | H | C(Me)₂CH₂SMe | H | 6-Me-2-OCH(CF₃)₂ | |
| Q27 | 27-289 | H | H | C(Me)₂CH₂SOMe | H | 6-Me-2-OCH(CF₃)₂ | 108 |
| Q27 | 27-290 | H | H | C(Me)₂CH₂SOMe | H | 6-Me-2-OCH(CF₃)₂ | |
| Q27 | 27-291 | 3-F | H | i-Pr | H | 6-Me-2-OCH(CF₃)₂ | |
| Q27 | 27-292 | 3-F | H | t-Bu | H | 6-Me-2-OCH(CF₃)₂ | |
| Q27 | 27-293 | 3-F | H | CH(Me)CH₂SMe | H | 6-Me-2-OCH(CF₃)₂ | |
| Q27 | 27-294 | 3-F | H | C(Me)₂CH₂SMe | H | 6-Me-2-OCH(CF₃)₂ | |
| Q27 | 27-295 | 3-F | H | C(Me)₃CH₂SOMe | H | 6-Me-2-OCH(CF₃)₂ | |
| Q27 | 27-296 | 3-F | H | C(Me)₂CH₂SO₂Me | H | 6-Me-2-OCH(CF₃)₂ | |
| Q27 | 27-297 | 3-Cl | H | i-Pr | H | 6-Me-2-OCH(CF₃)₂ | 257 |
| Q27 | 27-298 | 3-Cl | H | t-Bu | H | 6-Me-2-OCH(CF₃)₂ | 255 |
| Q27 | 27-299 | 3-Cl | Et | Et | H | 6-Me-2-OCH(CF₃)₂ | |
| Q27 | 27-300 | 3-Cl | H | CH(Me)CH₂SMe | H | 6-Me-2-OCH(CF₃)₂ | |
| Q27 | 27-301 | 3-Cl | H | CH(Me)CH₂SOMe | H | 6-Me-2-OCH(CF₃)₂ | |
| Q27 | 27-302 | 3-Cl | H | CH(Me)CH₂SO₂Me | H | 6-Me-2-OCH(CF₃)₂ | |

TABLE 7-continued

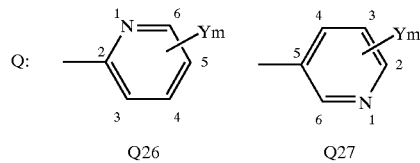

Q26  Q27

($Z^1 = Z^2 = O$)

| Q | No. | Xn | $R^1$ | $R^2$ | $R^3$ | Ym | mp (° C.) |
|---|---|---|---|---|---|---|---|
| Q27 | 27-303 | 3-Cl | H | CH(Me)CH$_2$SEt | H | 6-Me-2-OCH(CF$_3$)$_2$ | |
| Q27 | 27-304 | 3-Cl | H | CH(Me)CH$_2$SO$_2$Et | H | 6-Me-2-OCH(CF$_3$)$_2$ | |
| Q27 | 27-305 | 3-Cl | H | C(Me)$_2$CH$_2$SMe | H | 6-Me-2-OCH(CF$_3$)$_2$ | 236 |
| Q27 | 27-306 | 3-Cl | H | C(Me)$_2$CH$_2$SOMe | H | 6-Me-2-OCH(CF$_3$)$_2$ | 115 |
| Q27 | 27-307 | 3-Cl | H | C(Me)$_2$CH$_2$SO$_2$Me | H | 6-Me-2-OCH(CF$_3$)$_2$ | 221 |
| Q27 | 27-308 | 3-Br | H | i-Pr | H | 6-Me-2-OCH(CF$_3$)$_2$ | 252 |
| Q27 | 27-309 | 3-Br | H | t-Bu | H | 6-Me-2-OCH(CF$_3$)$_2$ | 255 |
| Q27 | 27-310 | 3-Br | Et | Et | H | 6-Me-2-OCH(CF$_3$)$_2$ | |
| Q27 | 27-311 | 3-Br | H | CH(Me)CH$_2$SMe | H | 6-Me-2-OCH(CF$_3$)$_2$ | |
| Q27 | 27-312 | 3-Br | H | CH(Me)CH$_2$SOMe | H | 6-Me-2-OCH(CF$_3$)$_2$ | |
| Q27 | 27-313 | 3-Br | H | CH(Me)CH$_2$SO$_2$Me | H | 6-Me-2-OCH(CF$_3$)$_2$ | |
| Q27 | 27-314 | 3-Br | H | CH(Me)CH$_2$SEt | H | 6-Me-2-OCH(CF$_3$)$_2$ | |
| Q27 | 27-315 | 3-Br | H | CH(Me)CH$_2$SO$_2$Et | H | 6-Me-2-OCH(CF$_3$)$_2$ | |
| Q27 | 27-316 | 3-Br | H | C(Me)$_2$CH$_2$SMe | H | 6-Me-2-OCH(CF$_3$)$_2$ | 228 |
| Q27 | 27-317 | 3-Br | H | C(Me)$_2$CH$_2$SOMe | H | 6-Me-2-OCH(CF$_3$)$_2$ | 115 |
| Q27 | 27-318 | 3-Br | H | C(Me)$_2$CH$_2$SO$_2$Me | H | 6-Me-2-OCH(CF$_3$)$_2$ | 225 |
| Q27 | 27-319 | 3-I | H | Me | H | 6-Me-2-OCH(CF$_3$)$_2$ | |
| Q27 | 27-320 | 3-I | H | Et | H | 6-Me-2-OCH(CF$_3$)$_2$ | |
| Q27 | 27-321 | 3-I | H | n-Pr | H | 6-Me-2-OCH(CF$_3$)$_2$ | |
| Q27 | 27-322 | 3-I | H | c-C$_3$H$_5$ | H | 6-Me-2-OCH(CF$_3$)$_2$ | |
| Q27 | 27-323 | 3-I | H | n-Bu | H | 6-Me-2-OCH(CF$_3$)$_2$ | 261 |
| Q27 | 27-324 | 3-I | H | s-Bu | H | 6-Me-2-OCH(CF$_3$)$_2$ | 274 |
| Q27 | 27-325 | 3-I | H | t-Bu | H | 6-Me-2-OCH(CF$_3$)$_2$ | 241 |
| Q27 | 27-326 | 3-I | H | i-Bu | H | 6-Me-2-OCH(CF$_3$)$_2$ | 264 |
| Q27 | 27-327 | 3-I | Et | Et | H | 6-Me-2-OCH(CF$_3$)$_2$ | 165 |
| Q27 | 27-328 | 3-I | Me | i-Pr | H | 6-Me-2-OCH(CF$_3$)$_2$ | |
| Q27 | 27-329 | 3-Cl-4-F | H | i-Pr | H | 6-Me-2-OCH(CF$_3$)$_2$ | |
| Q27 | 27-330 | 3-Cl-4-F | H | CH(Me)CH$_2$SMe | H | 6-Me-2-OCH(CF$_3$)$_2$ | |
| Q27 | 27-331 | 3-Cl-4-F | H | C(Me)$_2$CH$_2$SMe | H | 6-Me-2-OCH(CF$_3$)$_2$ | |
| Q27 | 27-332 | 3,4-Cl$_2$ | H | i-Pr | H | 6-Me-2-OCH(CF$_3$)$_2$ | 267 |
| Q27 | 27-333 | 3,4-Cl$_2$ | H | t-Bu | H | 6-Me-2-OCH(CF$_3$)$_2$ | |
| Q27 | 27-334 | 3,4-Cl$_2$ | H | CH(Me)CH$_2$SMe | H | 6-Me-2-OCH(CF$_3$)$_2$ | 210 |
| Q27 | 27-335 | 3,4-Cl$_2$ | H | CH(Me)CH$_2$SOMe | H | 6-Me-2-OCH(CF$_3$)$_2$ | |
| Q27 | 27-336 | 3,4-Cl$_2$ | H | CH(Me)CH$_2$SO$_2$Me | H | 6-Me-2-OCH(CF$_3$)$_2$ | 126 |
| Q27 | 27-337 | 3,4-Cl$_2$ | H | CH(Me)CH$_2$SEt | H | 6-Me-2-OCH(CF$_3$)$_2$ | 205 |
| Q27 | 27-338 | 3,4-Cl$_2$ | H | CH(Me)CH$_2$SOEt | H | 6-Me-2-OCH(CF$_3$)$_2$ | 119 |
| Q27 | 27-339 | 3,4-Cl$_2$ | H | CH(Me)CH$_2$SO$_2$Et | H | 6-Me-2-OCH(CF$_3$)$_2$ | 111 |
| Q27 | 27-340 | 3,4-Cl$_2$ | H | C(Me)$_2$CH$_2$SMe | H | 6-Me-2-OCH(CF$_3$)$_2$ | |
| Q27 | 27-341 | 3-Br-4-Cl | H | C(Me)$_2$CH$_2$SMe | H | 6-Me-2-OCH(CF$_3$)$_2$ | |
| Q27 | 27-342 | 3,4-Br$_2$ | H | C(Me)$_2$CH$_2$SMe | H | 6-Me-2-OCH(CF$_3$)$_2$ | |
| Q27 | 27-343 | 3-I-4-F | H | C(Me)$_2$CH$_2$SMe | H | 6-Me-2-OCH(CF$_3$)$_2$ | |
| Q27 | 27-344 | 3-I-4-Cl | H | C(Me)$_2$CH$_2$SMe | H | 6-Me-2-OCH(CF$_3$)$_2$ | |
| Q27 | 27-345 | 3-I-4-Br | H | C(Me)$_2$CH$_2$SMe | H | 6-Me-2-OCH(CF$_3$)$_2$ | |
| Q27 | 27-346 | 3,4-I$_2$ | H | C(Me)$_2$CH$_2$SMe | H | 6-Me-2-OCH(CF$_3$)$_2$ | |
| Q27 | 27-347 | 3-NO$_2$ | H | i-Pr | H | 6-Me-2-OCH(CF$_3$)$_2$ | 207 |
| Q27 | 27-348 | 3-NO$_2$ | H | t-Bu | H | 6-Me-2-OCH(CF$_3$)$_2$ | |
| Q27 | 27-349 | 3-NO$_2$ | Et | Et | H | 6-Me-2-OCH(CF$_3$)$_2$ | |
| Q27 | 27-350 | 3-NO$_2$ | H | CH(Me)CH$_2$SMe | H | 6-Me-2-OCH(CF$_3$)$_2$ | |
| Q27 | 27-351 | 3-NO$_2$ | H | CH(Me)CH$_2$SO$_2$Me | H | 6-Me-2-OCH(CF$_3$)$_2$ | |
| Q27 | 27-352 | 3-NO$_2$ | H | C(Me)$_2$CH$_2$SMe | H | 6-Me-2-OCH(CF$_3$)$_2$ | 244 |
| Q27 | 27-353 | 3-NO$_2$ | H | C(Me)$_2$CH$_2$SO$_2$Me | H | 6-Me-2-OCH(CF$_3$)$_2$ | 230 |
| Q27 | 27-354 | 3-CF$_3$ | H | i-Pr | H | 6-Me-2-OCH(CF$_3$)$_2$ | 211 |
| Q27 | 27-355 | 3-CF$_3$ | H | t-Bu | H | 6-Me-2-OCH(CF$_3$)$_2$ | 246 |
| Q27 | 27-356 | 3-CF$_3$ | Et | Et | H | 6-Me-2-OCH(CF$_3$)$_2$ | |
| Q27 | 27-357 | 3-CF$_3$ | H | CH(Me)CH$_2$SMe | H | 6-Me-2-OCH(CF$_3$)$_2$ | |
| Q27 | 27-358 | 3-CF$_3$ | H | CH(Me)CH$_2$SO$_2$Me | H | 6-Me-2-OCH(CF$_3$)$_2$ | |
| Q27 | 27-359 | 3-CF$_3$ | H | C(Me)$_2$CH$_2$SMe | H | 6-Me-2-OCH(CF$_3$)$_2$ | 226 |
| Q27 | 27-360 | 3-CF$_3$ | H | C(Me)$_2$CH$_2$SOMe | H | 6-Me-2-OCH(CF$_3$)$_2$ | 112 |
| Q27 | 27-361 | 3-CF$_3$ | H | C(Me)$_2$CH$_2$SO$_2$Me | H | 6-Me-2-OCH(CF$_3$)$_2$ | |
| Q27 | 27-362 | 3-OCF$_3$ | H | i-Pr | H | 6-Me-2-OCH(CF$_3$)$_2$ | |
| Q27 | 27-363 | 3-OCF$_3$ | H | CH(Me)CH$_2$SMe | H | 6-Me-2-OCH(CF$_3$)$_2$ | |
| Q27 | 27-364 | 3-OCF$_3$ | H | C(Me)$_2$CH$_2$SMe | H | 6-Me-2-OCH(CF$_3$)$_2$ | |
| Q27 | 27-365 | 3-SCF$_3$ | H | i-Pr | H | 6-Me-2-OCH(CF$_3$)$_2$ | |
| Q27 | 27-366 | 3-SCF$_3$ | H | CH(Me)CH$_2$SMe | H | 6-Me-2-OCH(CF$_3$)$_2$ | |
| Q27 | 27-367 | 3-SCF$_3$ | H | C(Me)$_2$CH$_2$SMe | H | 6-Me-2-OCH(CF$_3$)$_2$ | |
| Q27 | 27-368 | 3-SOCF$_3$ | H | i-Pr | H | 6-Me-2-OCH(CF$_3$)$_2$ | |

TABLE 7-continued

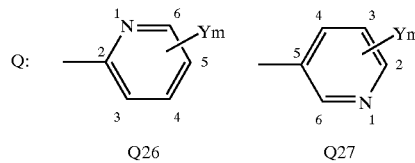

$(Z^1 = Z^2 = O)$

| Q | No. | Xn | $R^1$ | $R^2$ | $R^3$ | Ym | mp (° C.) |
|---|---|---|---|---|---|---|---|
| Q27 | 27-369 | 3-SO2CF$_3$ | H | i-Pr | H | 6-Me-2-OCH(CF$_3$)$_2$ | |
| Q27 | 27-370 | 3-Me | H | i-Pr | H | 6-Me-2-OCH(CF$_3$)$_2$ | |
| Q27 | 27-371 | 3-Et | H | i-Pr | H | 6-Me-2-OCH(CF$_3$)$_2$ | |
| Q27 | 27-372 | 5-t-Bu | H | i-Pr | H | 6-Me-2-OCH(CF$_3$)$_2$ | 280 |
| Q27 | 27-373 | 3-C≡CH | H | i-Pr | H | 6-Me-2-OCH(CF$_3$)$_2$ | |
| Q27 | 27-374 | 3-C≡CCF$_3$ | H | i-Pr | H | 6-Me-2-OCH(CF$_3$)$_2$ | |
| Q27 | 27-375 | 3-C≡C-t-Bu | H | i-Pr | H | 6-Me-2-OCH(CF$_3$)$_2$ | |
| Q27 | 27-376 | 3-C≡C-SiMe$_3$ | H | i-Pr | H | 6-Me-2-OCH(CF$_3$)$_2$ | |
| Q27 | 27-377 | 3-C≡C-Ph | H | i-Pr | H | 6-Me-2-OCH(CF$_3$)$_2$ | |
| Q27 | 27-378 | 3-I | H | i-Pr | H | 6-Me-2-OCF$_2$CHF$_2$ | 217 |
| Q27 | 27-379 | 3-I | H | t-Bu | H | 6-Me-2-OCF$_2$CHF$_2$ | |
| Q27 | 27-380 | 3-I | Et | Et | H | 6-Me-2-OCF$_2$CHF$_2$ | |
| Q27 | 27-381 | 3-I | H | CH(Me)CH$_2$SMe | H | 6-Me-2-OCF$_2$CHF$_2$ | |
| Q27 | 27-382 | 3-I | H | CH(Me)CH$_2$SOMe | H | 6-Me-2-OCF$_2$CHF$_2$ | |
| Q27 | 27-383 | 3-I | H | CH(Me)CH$_2$SO$_2$Me | H | 6-Me-2-OCF$_2$CHF$_2$ | |
| Q27 | 27-384 | 3-I | H | C(Me)$_2$CH$_2$SMe | H | 6-Me-2-OCF$_2$CHF$_2$ | 99 |
| Q27 | 27-385 | 3-I | H | C(Me)$_2$CH$_2$SOMe | H | 6-Me-2-OCF$_2$CHF$_2$ | |
| Q27 | 27-386 | 3-I | H | C(Me)$_2$CH$_2$SO$_2$Me | H | 6-Me-2-OCF$_2$CHF$_2$ | |
| Q27 | 27-387 | 3-I | H | i-Pr | H | 6-Cl-2-OCF$_2$CHF$_2$ | 200 |
| Q27 | 27-388 | 3-I | H | C(Me)$_2$CH$_2$SMe | H | 6-Cl-2-OCF$_2$CHF$_2$ | 142 |
| Q27 | 27-389 | 3-I | H | C(Me)$_2$CH$_2$SOMe | H | 6-Cl-2-OCF$_2$CHF$_2$ | |
| Q27 | 27-390 | 3-I | H | C(Me)$_2$CH$_2$SO$_2$Me | H | 6-Cl-2-OCF$_2$CHF$_2$ | |
| Q27 | 27-391 | 3-I | H | i-Pr | H | 6-Me-2-OCF$_2$CHFCF$_3$ | 205 |
| Q27 | 27-392 | 3-I | H | CH(Me)CH$_2$SMe | H | 6-Me-2-OCF$_2$CHFCF$_3$ | |
| Q27 | 27-393 | 3-I | H | C(Me)$_2$CH$_2$SMe | H | 6-Me-2-OCF$_2$CHFCF$_3$ | 158 |
| Q27 | 27-394 | 3-I | H | i-Pr | H | 6-Me-2-OCF$_2$CHFCF$_3$ | |
| Q27 | 27-395 | 3-I | H | CH(Me)CH$_2$SMe | H | 6-Me-2-OCF$_2$CHFCF$_3$ | |
| Q27 | 27-396 | 3-I | H | C(Me)$_2$CH$_2$SMe | H | 6-Me-2-OCF$_2$CHFCF$_3$ | 126 |
| Q27 | 27-397 | 3-I | H | i-Pr | H | 6-Me-2-OCF$_2$CHFOC$_3$F$_7$-n | 194 |
| Q27 | 27-398 | 3-I | H | t-Bu | H | 6-Me-2-OCF$_2$CHFOC$_3$F$_7$-n | |
| Q27 | 27-399 | 3-I | H | CH(Me)CH$_2$SMe | H | 6-Me-2-OCF$_2$CHFOC$_3$F$_7$-n | |
| Q27 | 27-400 | 3-I | H | CH(Me)CH$_2$SOMe | H | 6-Me-2-OCF$_2$CHFOC$_3$F$_7$-n | |
| Q27 | 27-401 | 3-I | H | CH(Me)CH$_2$SO$_2$Me | H | 6-Me-2-OCF$_2$CHFOC$_3$F$_7$-n | |
| Q27 | 27-402 | 3-I | H | C(Me)$_2$CH$_2$SMe | H | 6-Me-2-OCF$_2$CHFOC$_3$F$_7$-n | 91 |
| Q27 | 27-403 | 3-I | H | C(Me)$_2$CH$_2$SOMe | H | 6-Me-2-OCF$_2$CHFOC$_3$F$_7$-n | 81 |
| Q27 | 27-404 | 3-I | H | C(Me)$_2$CH$_2$SO$_2$Me | H | 6-Me-2-OCF$_2$CHFOC$_3$F$_7$-n | 157 |
| Q27 | 27-405 | 3-I | H | i-Pr | H | 6-Cl-2-OCF$_2$CHFOC$_3$F$_7$-n | 205 |
| Q27 | 27-406 | 3-I | H | t-Bu | H | 6-Cl-2-OCF$_2$CHFOC$_3$F$_7$-n | |
| Q27 | 27-407 | 3-I | H | CH(Me)CH$_2$SMe | H | 6-Cl-2-OCF$_2$CHFOC$_3$F$_7$-n | 106 |
| Q27 | 27-408 | 3-I | H | CH(Me)CH$_2$SOMe | H | 6-Cl-2-OCF$_2$CHFOC$_3$F$_7$-n | |
| Q27 | 27-409 | 3-I | H | CH(Me)CH$_2$SO$_2$Me | H | 6-Cl-2-OCF$_2$CHFOC$_3$F$_7$-n | |
| Q27 | 27-410 | 3-I | H | C(Me)$_2$CH$_2$SMe | H | 6-Cl-2-OCF$_2$CHFOC$_3$F$_7$-n | |
| Q27 | 27-411 | 3-I | H | C(Me)$_2$CH$_2$SOMe | H | 6-Cl-2-OCF$_2$CHFOC$_3$F$_7$-n | |
| Q27 | 27-412 | 3-I | H | C(Me)$_2$CH$_2$SO$_2$Me | H | 6-Cl-2-OCF$_2$CHFOC$_3$F$_7$-n | |
| Q27 | 27-413 | 3-I | H | i-Pr | H | 6-Me-2-OCH$_2$C$_2$F$_5$ | 259 |
| Q27 | 27-414 | 3-I | H | CH(Me)CH$_2$SMe | H | 6-Me-2-OCH$_2$C$_2$F$_5$ | 208 |
| Q27 | 27-415 | 3-I | H | C(Me)$_2$CH$_2$SMe | H | 6-Me-2-OCH$_2$C$_2$F$_5$ | |
| Q27 | 27-416 | 3-I | H | i-Pr | H | 6-Me-2-OCH$_2$-n-C$_3$F$_7$ | |
| Q27 | 27-417 | 3-I | H | CH(Me)CH$_2$SMe | H | 6-Me-2-OCH$_2$-n-C$_3$F$_7$ | |
| Q27 | 27-418 | 3-I | H | C(Me)$_2$CH$_2$SMe | H | 6-Me-2-OCH$_2$-n-C$_3$F$_7$ | |
| Q27 | 27-419 | 3-I | H | i-Pr | H | 6-Me-2-O-(2,4-Cl$_2$-Ph) | |
| Q27 | 27-420 | 3-I | H | C(Me)$_2$CH$_2$SMe | H | 6-Me-2-O-(2,4-Cl$_2$-Ph) | |
| Q27 | 27-421 | 3-I | H | i-Pr | H | 6-Me-2-O-(2-Cl-4-CF$_3$-Ph) | |
| Q27 | 27-422 | 3-I | H | C(Me)$_2$CH$_2$SMe | H | 6-Me-2-O-(2-Cl-4-CF$_3$-Ph) | |
| Q27 | 27-423 | 3-I | H | i-Pr | H | 6-Me-2-SCF$_3$ | |
| Q27 | 27-424 | 3-I | H | CH(Me)CH$_2$SMe | H | 6-Me-2-SCF$_3$ | |
| Q27 | 27-425 | 3-I | H | C(Me)$_2$CH$_2$SMe | H | 6-Me-2-SCF$_3$ | |
| Q27 | 27-426 | 3-I | H | C(Me)$_2$CH$_2$SOMe | H | 6-Me-2-SCF$_3$ | |
| Q27 | 27-427 | 3-I | H | C(Me)$_3$CH$_2$SO$_2$Me | H | 6-Me-2-SCF$_3$ | |
| Q27 | 27-428 | 3-I | H | C(Me)$_2$CH$_2$SO$_2$Me | H | 6-Me-2-SOCF$_3$ | |
| Q27 | 27-429 | 3-I | H | C(Me)$_2$CH$_2$SO$_2$Me | H | 6-Me-2-SO$_2$CF$_3$ | |
| Q27 | 27-430 | 3-I | H | i-Pr | H | 6-Me-2-SC$_2$F$_5$ | |
| Q27 | 27-431 | 3-I | H | C(Me)$_2$CH$_2$SMe | H | 6-Me-2-SC$_2$F$_5$ | |
| Q27 | 27-432 | 3-I | H | i-Pr | H | 6-Me-2-S-n-C$_3$F$_7$ | |
| Q27 | 27-433 | 3-I | H | C(Me)$_2$CH$_2$SMe | H | 6-Me-2-S-n-C$_3$F$_7$ | |
| Q27 | 27-436 | 3-I | H | C(Me)$_2$CH$_2$SMe | H | 6-Me-2-S-CH(CF$_3$)$_2$ | |

TABLE 7-continued

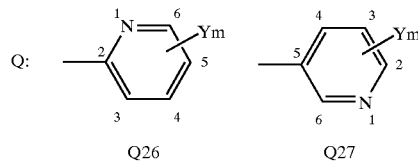

Q26  Q27

$(Z^1 = Z^2 = O)$

| Q | No. | Xn | R¹ | R² | R³ | Ym | mp (° C.) |
|---|---|---|---|---|---|---|---|
| Q27 | 27-434 | 3-I | H | i-Pr | H | 6-Me-2-SCF$_2$CHF$_2$ | |
| Q27 | 27-435 | 3-I | H | CH(Me)CH$_2$SMe | H | 6-Me-2-SCF$_2$CHFCF$_3$ | |
| Q27 | 27-437 | 3-I | H | i-Pr | H | 6-Me-2-NHCOCF$_3$ | |
| Q27 | 27-438 | 3-I | H | i-Pr | H | 6-Me-2-NHCOC$_2$F$_5$ | 192 |
| Q27 | 27-439 | 3-I | H | C(Me)$_2$CH$_2$SMe | H | 6-Me-2-NHCOC$_2$F$_5$ | 205 |
| Q27 | 27-440 | 3-I | H | i-Pr | H | 6-Me-2-NHCOC$_3$F$_7$-n | |
| Q27 | 27-441 | 3-I | H | C(Me)$_2$CH$_2$SMe | H | 6-Me-2-NHCOC$_3$F$_7$-n | |
| Q27 | 27-442 | 3-I | H | C(Me)$_2$CH$_2$SMe | H | 6-Me-2-NHCO-(2,4-Cl$_2$-Ph) | |
| Q27 | 27-443 | 3-I | H | i-Pr | H | 6-Me-2-NHCO-(4-CF$_3$-Ph) | |
| Q27 | 27-444 | 3-I | H | C(Me)$_2$CH$_2$SMe | H | 6-Me-2-N(COC$_2$F$_5$)$_2$ | |
| Q27 | 27-445 | 3-I | H | C(Me)$_2$CH$_2$SMe | H | 6-Me-2-NHCH$_2$CF$_3$ | |
| Q27 | 27-446 | 3-I | H | C(Me)$_2$CH$_2$SMe | H | 6-Me-2-NHCH$_2$CF$_3$ | |
| Q27 | 27-447 | 3-I | H | C(Me)$_2$CH$_2$SMe | H | 6-Me-2-NHCH$_2$C$_2$F$_5$ | |
| Q27 | 27-448 | 3-I | H | C(Me)$_2$CH$_2$SMe | H | 6-Me-2-Cl | 173 |
| Q27 | 27-449 | 3-CF$_3$ | H | C(Me)$_2$CH$_2$SMe | H | 6-Me-2-i-C$_3$F$_7$ | 214 |
| Q27 | 27-450 | H | H | C(Me)$_2$CH$_2$SMe | H | 6-Me-2-i-C$_3$F$_7$ | 155 |
| Q27 | 27-451 | 3-F | H | C(Me)$_2$CH$_2$SMe | H | 6-Me-2-i-C$_3$F$_7$ | 202 |
| Q27 | 27-452 | 3-F | H | C(Me)$_2$CH$_2$SO$_2$Me | H | 6-Me-2-i-C$_3$F$_7$ | 197 |
| Q27 | 27-453 | 3-Br | H | C(Me)$_2$CH$_2$SMe | H | 6-Me-2-i-C$_3$F$_7$ | 206 |
| Q27 | 27-454 | 3-Br | H | C(Me)$_2$CH$_2$SO$_2$Me | H | 6-Me-2-i-C$_3$F$_7$ | 225 |
| Q27 | 27-455 | 3,4-Cl$_2$ | H | C(Me)$_2$CH$_2$SMe | H | 6-Me-2-i-C$_3$F$_7$ | 259 |
| Q27 | 27-456 | 3-CF$_3$ | H | i-Pr | H | 6-Me-2-i-C$_3$F$_7$ | 221 |
| Q27 | 27-457 | H | H | i-Pr | H | 6-Cl-2-i-C$_3$F$_7$ | 200 |
| Q27 | 27-458 | H | H | C(Me)$_2$CH$_2$SMe | H | 6-Cl-2-i-C$_3$F$_7$ | 110 |
| Q27 | 27-459 | 3-Cl | H | i-Pr | H | 6-Cl-2-i-C$_3$F$_7$ | 181 |
| Q27 | 27-460 | 3-I | H | t-Bu | H | 6-Cl-2-i-C$_3$F$_7$ | 191 |
| Q27 | 27-461 | 3-F | H | C(Me)$_2$CH$_2$SMe | H | 6-Cl-2-i-C$_3$F$_7$ | 182 |
| Q27 | 27-462 | 3-Cl | H | C(Me)$_2$CH$_2$SMe | H | 6-Cl-2-i-C$_3$F$_7$ | 161 |
| Q27 | 27-463 | 3,4-Cl$_2$ | H | C(Me)$_2$CH$_2$SMe | H | 6-Cl-2-i-C$_3$F$_7$ | 153 |
| Q27 | 27-464 | 3-CF$_3$ | H | C(Me)$_2$CH$_2$SMe | H | 6-Cl-2-i-C$_3$F$_7$ | 165 |
| Q27 | 27-465 | 3-NO$_2$ | H | C(Me)$_2$CH$_2$SMe | H | 6-Cl-2-i-C$_3$F$_7$ | 235 |
| Q27 | 27-466 | 3-I | H | i-Pr | H | 6-Me-2-O(4-CF$_3$-Ph) | 238 |
| Q27 | 27-467 | 3-I | H | C(Me)$_2$CH$_2$SMe | H | 6-Me-2-O(4-CF$_3$-Ph) | 111 |
| Q27 | 27-468 | 3-I | H | C(Me)$_2$CH$_2$SOMe | H | 6-Me-2-O(4-CF$_3$-Ph) | 106 |
| Q27 | 27-469 | 3-I | H | C(Me)$_2$CH$_2$SO$_2$Me | H | 6-Me-2-O(4-CF$_3$-Ph) | 97 |
| Q27 | 27-470 | 3-CF$_3$ | H | C(Me)$_2$CH$_2$SMe | H | 6-Me-2-OCF$_2$CHFOCF$_3$ | Amorphous |
| Q27 | 27-471 | 3-I | H | i-Pr | H | 6-Me-2-OCF=CFCF$_3$ | 165 |
| Q27 | 27-472 | 3-I | H | i-Pr | H | 6-Me-2-OCF$_2$CHFOCF$_3$ | 185 |

In Table 7, some compounds are amorphous or pastry. ¹H-NMR data of such compounds are shown below.

| No | ¹H-NMR [δ (ppm/CDCl$_3$)] |
|---|---|
| 27-153 | 1.59(s. 3H), 1.64(s. 3H), 2.26(s. 3H), 2.62(s. 3H), 2.88(d. 1H), 3.02(d. 1H), 6.83(br. 1H), 7.23(t. 1H), 7.58(dd. 1H), 7.78(d. 1H), 8.00(dd. 1H), 8.58(br. 1H), 8.81(d. 1H). |
| 27-235 | 1.64(s. 3H), 1.66(s. 3H), 2.40(s. 3H), 2.88(d. 1H), 3.24(d. 1H), 6.72(br. 1H), 7.24(t. 1H), 7.70(dd. 1H), 7.74(d. 1H), 8.03(dd. 1H), 8.85(br. 1H), 9.12(d. 1H). |
| 27-236 | 1.71(s. 6H), 2.71(s. 3H), 3.63(s. 2H), 6.25(br. 1H), 7.25(t. 1H), 7.70(dd. 1H), 7.75(dd. 1H), 8.05(dd. 1H), 8.81(br. 1H), 9.11(d. 1H). |
| 27-238 | 1.68(s. 3H), 1.72(s. 3H), 2.49(s. 3H), 2.99(d. 1H), 3.21(d. 1H), 6.76(br. 1H), 7.21(t. 1H), 7.50(dd. 1H), 7.66(dd. 1H), 7.84(dd. 1H), 8.37(dd. 1H), 8.68(d. 1H), 9.75(br. 1H). |
| 27-239 | 1.80(s. 6H), 2.87(s. 3H), 3.73(s. 2H), 6.23(br. 1H), 7.23(t. 1H), 7.43(dd. 1H), 7.65(dd. 1H), 7.82(dd. 1H), 8.35(dd. 1H), 8.64(d. 1H), 9.88(br. 1H). |
| 27-244 | 1.60(s. 3H), 1.63(s. 3H), 2.41(s. 3H), 2.84(d. 1H), 3.31(d. 1H), 4.02(s. 1H), 6.59(br. 1H), 7.21(t. 1H), 7.34(dd. 1H), 7.69(dd. 1H), 7.99(dd. 1H), 8.65(br. 1H), 8.88(d. 1H). |
| 27-247 | 1.31(dd. 6H), 3.50(s. 3H), 4.33(m. 1H), 5.60(d. 1H), 7.19(t. 1H), 7.68(d. 1H), 7.74(dd. 1H), 8.00(d. 1H), 9.26(d. 1H), 11.8(br. 1H). |
| 27-470 | 1.42(s. 6H), 1.96(s. 3H), 2.53(s. 3H), 2.81(s. 2H), 6.17(s. 1H), 6.62(dt. 1H), 6.90(d. 1H), 7.66(t. 1H), 7.85(d. 1H), 8.03(d. 1H), 8.63(d. 1H), 8.71(s. 1H). |

TABLE 8

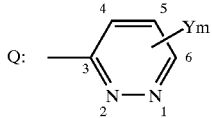

Q29

($Z^1 = Z^2 = O$)

| Q | No. | Xn | $R^1$ | $R^2$ | $R^3$ | Ym | mp (° C.) |
|---|---|---|---|---|---|---|---|
| Q29 | 29-1 | 3-Cl | H | i-Pr | H | H | |
| Q29 | 29-2 | 3-Cl | H | i-Pr | H | 4-Me-6-$C_2F_5$ | |
| Q29 | 29-3 | 3-Br | H | i-Pr | H | 4-Me-6-n-$C_3F_7$ | |
| Q29 | 29-4 | 3-$NO_2$ | H | i-Pr | H | 4-Me-6-i-$C_3F_7$ | |
| Q29 | 29-5 | 3-I | H | i-Pr | H | H | |
| Q29 | 29-6 | 3-I | H | i-Pr | H | 6-Cl | 136 |
| Q29 | 29-7 | 3-I | H | i-Pr | H | 6-$C_2F_5$ | |
| Q29 | 29-8 | 3-I | H | i-Pr | H | 6-n-$C_3F_7$ | |
| Q29 | 29-9 | 3-I | H | i-Pr | H | 6-i-$C_3F_7$ | |
| Q29 | 29-10 | 3-I | H | i-Pr | H | 4-Me-6-$C_2F_5$ | |
| Q29 | 29-11 | 3-I | H | i-Pr | H | 4-Me-6-n-$C_3F_7$ | |
| Q29 | 29-12 | 3-I | H | i-Pr | H | 4-Me-6-i-$C_3F_7$ | |
| Q29 | 29-13 | 3-I | H | i-Pr | H | 4-Me-5-$C_2F_5$ | |
| Q29 | 29-14 | 3-I | H | i-Pr | H | 4-Me-5-n-$C_3F_7$ | |
| Q29 | 29-15 | 3-I | H | i-Pr | H | 4-Me-5-i-$C_3F_7$ | |
| Q29 | 29-16 | 3-I | H | t-Bu | H | 6-i-$C_3F_7$ | |
| Q29 | 29-17 | 3-I | H | t-Bu | H | 6-$C_2F_5$ | |
| Q29 | 29-18 | 3-I | H | t-Bu | H | 6-n-$C_3F_7$ | |
| Q29 | 29-19 | 3-I | H | t-Bu | H | 4-Me-6-i-$C_3F_7$ | |
| Q29 | 29-20 | 3-I | H | $CH(CH_3)CH_2SCH_3$ | H | 4-Me-6-i-$C_3F_7$ | |
| Q29 | 29-21 | 3-I | H | $CH(CH_3)CH_2SOCH_3$ | H | 4-Me-6-i-$C_3F_7$ | |
| Q29 | 29-22 | 3-I | H | $CH(CH_3)CH_2SO_2CH_3$ | H | 4-Me-6-i-$C_3F_7$ | |
| Q29 | 29-23 | 3-I | H | $C(CH_3)_2CH_2SCH_3$ | H | 4-Me-6-i-$C_3F_7$ | |
| Q29 | 29-24 | 3-I | H | $C(CH_3)_2CH_2SOCH_3$ | H | 4-Me-6-i-$C_3F_7$ | |
| Q29 | 29-25 | 3-I | H | $C(CH_3)_2CH_2SO_2CH_3$ | H | 4-Me-6-i-$C_3F_7$ | |
| Q29 | 29-26 | 3-I | H | $CH(CH_3)CH_2NHAc$ | H | 4-Me-6-i-$C_3F_7$ | |
| Q29 | 29-27 | 3-I | H | $C(CH_3)_2CH_2NHAc$ | H | 4-Me-6-i-$C_3F_7$ | |
| Q29 | 29-28 | 3-I | H | $CH(CH_3)CH_2CH_2OCH_3$ | H | 4-Me-6-i-$C_3F_7$ | |
| Q29 | 29-29 | 3-I | H | $C(CH_3)_2CH_2CH_2OCH_3$ | H | 4-Me-6-i-$C_3F_7$ | |
| Q29 | 29-30 | 3-I | Et | Et | H | H | |
| Q29 | 29-31 | 3-I | Et | Et | H | 4-Me-6-$C_2F_5$ | |
| Q29 | 29-32 | 3-I | Et | Et | H | 4-Me-6-n-$C_3F_7$ | |
| Q29 | 29-33 | 3-I | Et | Et | H | 4-Me-6-i-$C_3F_7$ | |
| Q29 | 29-34 | 3-I | Et | Et | H | 6-Cl | |
| Q29 | 29-35 | 3-I | Et | Et | H | 6-Br | |
| Q29 | 29-36 | 3-I | Et | Et | H | 6-n-$C_3F_7$ | |
| Q29 | 29-37 | 3-$CF_3$ | H | i-Pr | H | 4-Me-6-$C_2F_5$ | |
| Q29 | 29-38 | 3-Ph | H | i-Pr | H | 4-Me-6-n-$C_3F_7$ | |
| Q29 | 29-39 | 3-$SOCF_3$ | H | i-Pr | H | 4-Me-6-i-$C_3F_7$ | |
| Q29 | 29-40 | 3-$C_2F_5$ | H | i-Pr | H | 4-Me-6-$C_2F_5$ | |
| Q29 | 29-41 | 3-I-4-Cl | H | i-Pr | H | 4-Me-6-n-$C_3F_7$ | |
| Q29 | 29-42 | 3-I-4-$CF_3$ | H | i-Pr | H | 4-Me-6-i-$C_3F_7$ | |
| Q29 | 29-43 | 3-$CF_3$-4-Cl | H | i-Pr | H | 4-Me-6-$C_2F_5$ | |
| Q29 | 29-44 | 3-$OCF_2$O-4 | H | i-Pr | H | 4-Me-6-n-$C_3F_7$ | |
| Q29 | 29-45 | 3-$OCF_2CF_2$O-4 | H | i-Pr | H | 4-Me-6-i-$C_3F_7$ | |

TABLE 9

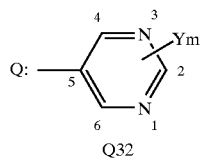

Q32

($Z^1 = Z^2 = O$)

| Q | No. | Xn | $R^1$ | $R^2$ | $R^3$ | Ym | mp (° C.) |
|---|---|---|---|---|---|---|---|
| Q32 | 32-1 | 3-Cl | H | i-Pr | H | H | |
| Q32 | 32-2 | 3-Cl | H | i-Pr | H | 4-Me-2-$C_2F_5$ | |
| Q32 | 32-3 | 3-Br | H | i-Pr | H | 4-Me-2-n-$C_3F_7$ | |
| Q32 | 32-4 | 3-$NO_2$ | H | i-Pr | H | 4-Me-2-i-$C_3F_7$ | |
| Q32 | 32-5 | 3-I | H | i-Pr | H | 2-$C_2F_5$ | |
| Q32 | 32-6 | 3-I | H | i-Pr | H | 2-n-$C_3F_7$ | |
| Q32 | 32-7 | 3-I | H | i-Pr | H | 2-i-$C_3F_7$ | |
| Q32 | 32-8 | 3-I | H | i-Pr | H | 4-Me-2-$C_2F_5$ | |
| Q32 | 32-9 | 3-I | H | i-Pr | H | 4-Me-2-n-$C_3F_7$ | |
| Q32 | 32-10 | 3-I | H | i-Pr | H | 4-Me-2-i-$C_3F_7$ | |
| Q32 | 32-11 | 3-I | H | i-Pr | H | 4,6-$Cl_2$ | 257 |
| Q32 | 32-12 | 3-I | H | t-Bu | H | 2-i-$C_3F_7$ | |
| Q32 | 32-13 | 3-I | H | t-Bu | H | 2-$C_2F_5$ | |
| Q32 | 32-14 | 3-I | H | t-Bu | H | 2-n-$C_3F_7$ | |
| Q32 | 32-15 | 3-I | H | t-Bu | H | 4-Me-2-i-$C_3F_7$ | |
| Q32 | 32-16 | 3-I | H | $CH(CH_3)CH_2SCH_3$ | H | 4-Me-2-i-$C_3F_7$ | |
| Q32 | 32-17 | 3-I | H | $CH(CH_3)CH_2OCH_3$ | H | 4-Me-2-i-$C_3F_7$ | |
| Q32 | 32-18 | 3-I | H | $CH(CH_3)CH_2SO_2CH_3$ | H | 4-Me-2-i-$C_3F_7$ | |
| Q32 | 32-19 | 3-I | H | $C(CH_3)_2CH_2SCH_3$ | H | 4-Me-2-i-$C_3F_7$ | 202 |
| Q32 | 32-20 | 3-I | H | $C(CH_3)_2CH_2SOCH_3$ | H | 4-Me-2-i-$C_3F_7$ | |
| Q32 | 32-21 | 3-I | H | $C(CH_3)_2CH_2SO_2CH_3$ | H | 4-Me-2-i-$C_3F_7$ | |
| Q32 | 32-22 | 3-I | H | $CH(CH_3)CH_2SEt$ | H | 4-Me-2-i-$C_3F_7$ | |
| Q32 | 32-23 | 3-I | H | $C(CH_3)_2CH_2SEt$ | H | 4-Me-2-i-$C_3F_7$ | |
| Q32 | 32-24 | 3-I | H | $CH(CH_3)CH_2SCH_3$ | H | 4-Me-2-i-$C_3F_7$ | |
| Q32 | 32-25 | 3-I | H | $C(CH_3)_2CH_2SCH_3$ | H | 4-Me-2-i-$C_3F_7$ | |
| Q32 | 32-26 | 3-I | Et | Et | H | 4-Me-2-$C_2F_5$ | |
| Q32 | 32-27 | 3-I | Et | Et | H | 4-Me-2-n-$C_3F_7$ | |
| Q32 | 32-28 | 3-I | Et | Et | H | 4-Me-2-i-$C_3F_7$ | |
| Q32 | 32-29 | 3-I | Et | Et | H | 2-Cl | |
| Q32 | 32-30 | 3-I | Et | Et | H | 2-Br | |
| Q32 | 32-31 | 3-I | Et | Et | H | 2-n-$C_3F_7$ | |
| Q32 | 32-32 | 3-$CF_3$ | H | i-Pr | H | 4-Me-2-$C_2F_5$ | |
| Q32 | 32-33 | 3-Ph | H | i-Pr | H | 4-Me-2-n-$C_3F_7$ | |
| Q32 | 32-34 | 3-$SOCF_3$ | H | i-Pr | H | 4-Me-2-i-$C_3F_7$ | |
| Q32 | 32-35 | 3-$C_2F_5$ | H | i-Pr | H | 4-Me-2-$C_2F_5$ | |
| Q32 | 32-36 | 3-I-4-Cl | H | i-Pr | H | 4-Me-2-n-$C_3F_7$ | |
| Q32 | 32-37 | 3-I-4-$CF_3$ | H | i-Pr | H | 4-Me-2-i-$C_3F_7$ | |
| Q32 | 32-38 | 3-$CF_3$-4-Cl | H | i-Pr | H | 4-Me-2-$C_2F_5$ | |
| Q32 | 32-39 | 3-$OCF_2$O-4 | H | i-Pr | H | 4-Me-2-n-$C_3F_7$ | |
| Q32 | 32-40 | 3-$OCF_2CF_2$O-4 | H | i-Pr | H | 4-Me-2-i-$C_3F_7$ | |
| Q32 | 32-41 | 3-I | H | $CH(Me)CH_2SMe$ | H | 4-Me-2-Cl | 210 |
| Q32 | 32-42 | 3-I | Et | Et | H | 4,6-$(OCH_2F_3)_2$ | Amorphous |

In Table 9, $^1$H-NMR data of the compound being amorphous is shown below.

| No | $^1$H-NMR [δ (ppm/$CDCl_3$)] |
|---|---|
| 32-42 | 1.04(s. 3H), 1.31(t. 3H), 3.10(m. 3H), 3.42(m. 1H), 3.80(m. 1H), 4.96–4.74(m. 4H), 7.22(t. 1H), 7.87(d. 1H), 8.04(dd. 1H), 8.39(s. 1H). |

TABLE 10

Q33: pyrimidin-2-yl (positions 1-N, 2-Q, 3-N, 4, 5, 6-Ym)

($Z^1 = Z^2 = O$)

| Q | No. | Xn | $R^1$ | $R^2$ | $R^3$ | Ym | mp (° C.), nD (° C.) |
|---|---|---|---|---|---|---|---|
| Q33 | 33-1 | H | H | i-Pr | H | 4,6-(OMe)$_2$ | 61 |
| Q33 | 33-2 | 3-Cl | H | i-Pr | H | H | |
| Q33 | 33-3 | 3-Cl | H | i-Pr | H | 5-C$_2$F$_5$ | |
| Q33 | 33-4 | 3-Br | H | i-Pr | H | 5-n-C$_3$F$_7$ | |
| Q33 | 33-5 | 3-NO$_2$ | H | i-Pr | H | 5-i-C$_3$F$_7$ | |
| Q33 | 33-6 | 3-I | H | i-Pr | H | 5-C$_2$F$_5$ | |
| Q33 | 33-7 | 3-I | H | i-Pr | H | 5-n-C$_3$F$_7$ | |
| Q33 | 33-8 | 3-I | H | i-Pr | H | 5-i-C$_3$F$_7$ | |
| Q33 | 33-9 | 3-I | H | i-Pr | H | 4,6-OMe$_2$ | nD 1.5672 (20.9) |
| Q33 | 33-10 | 3-I | H | i-Pr | H | 4,6-OMe$_2$-5-i-C$_3$F$_7$ | nD 1.5045 (21.9) |
| Q33 | 33-11 | 3-I | H | t-Bu | H | 5-i-C$_3$F$_7$ | |
| Q33 | 33-12 | 3-I | H | t-Bu | H | 5-C$_2$F$_5$ | |
| Q33 | 33-13 | 3-I | H | t-Bu | H | 5-n-C$_3$F$_7$ | |
| Q33 | 33-14 | 3-I | H | CH(CH$_3$)CH$_2$SCH$_3$ | H | 5-i-C$_3$F$_7$ | |
| Q33 | 33-15 | 3-I | H | CH(CH$_3$)CH$_2$SOCH$_3$ | H | 5-i-C$_3$F$_7$ | |
| Q33 | 33-16 | 3-I | H | CH(CH$_3$)CH$_2$SO$_2$CH$_3$ | H | 5-i-C$_3$F$_7$ | |
| Q33 | 33-17 | 3-I | H | C(CH$_3$)$_2$CH$_2$SCH$_3$ | H | 5-i-C$_3$F$_7$ | |
| Q33 | 33-18 | 3-I | H | C(CH$_3$)$_2$CH$_2$SOCH$_3$ | H | 5-i-C$_3$F$_7$ | |
| Q33 | 33-19 | 3-I | H | C(CH$_3$)$_2$CH$_2$SO$_2$CH$_3$ | H | 5-i-C$_3$F$_7$ | |
| Q33 | 33-20 | 3-I | H | CH(CH$_3$)CH$_2$SEt | H | 5-i-C$_3$F$_7$ | |
| Q33 | 33-21 | 3-I | H | C(CH$_3$)$_2$CH$_2$SEt | H | 5-i-C$_3$F$_7$ | |
| Q33 | 33-22 | 3-I | H | CH(CH$_3$)CH$_2$CH$_2$SCH$_3$ | H | 5-i-C$_3$F$_7$ | |
| Q33 | 33-23 | 3-I | H | C(CH$_3$)$_2$CH$_2$CH$_2$SCH$_3$ | H | 5-i-C$_3$F$_7$ | |
| Q33 | 33-24 | 3-I | Et | Et | H | 5-C$_2$F$_5$ | |
| Q33 | 33-25 | 3-I | Et | Et | H | 5-n-C$_3$F$_7$ | |
| Q33 | 33-26 | 3-I | Et | Et | H | 5-i-C$_3$F$_7$ | |
| Q33 | 33-27 | 3-I | Et | Et | H | 5-Cl | |
| Q33 | 33-28 | 3-I | Et | Et | H | 5-Br | |
| Q33 | 33-29 | 3-I | Et | Et | H | 5-n-C$_3$F$_7$ | |

TABLE 11

Q34: pyrazin-2-yl ($Z^1 = Z^2 = O$)

| Q | No. | Xn | $R^1$ | $R^2$ | $R^3$ | Ym | mp (° C.) |
|---|---|---|---|---|---|---|---|
| Q34 | 34-1 | 3-Cl | H | i-Pr | H | H | |
| Q34 | 34-2 | 3-Cl | H | i-Pr | H | 3-Me-5-C$_2$F$_5$ | |
| Q34 | 34-3 | 3-Br | H | i-Pr | H | 3-Me-5-n-C$_3$F$_7$ | |
| Q34 | 34-4 | 3-NO$_2$ | H | i-Pr | H | 3-Me-5-i-C$_3$F$_7$ | |
| Q34 | 34-5 | 3-I | H | i-Pr | H | H | 165 |
| Q34 | 34-6 | 3-I | H | i-Pr | H | 5-I | 198 |
| Q34 | 34-7 | 3-I | H | i-Pr | H | 5-C$_2$F$_5$ | |
| Q34 | 34-8 | 3-I | H | i-Pr | H | 5-n-C$_3$F$_7$ | |
| Q34 | 34-9 | 3-I | H | i-Pr | H | 5-i-C$_3$F$_7$ | |
| Q34 | 34-10 | 3-I | H | i-Pr | H | 3-Me-5-C$_2$F$_5$ | |
| Q34 | 34-11 | 3-I | H | i-Pr | H | 3-Me-5-n-C$_3$F$_7$ | |
| Q34 | 34-12 | 3-I | H | i-Pr | H | 3-Me-5-i-C$_3$F$_7$ | |
| Q34 | 34-13 | 3-I | H | i-Pr | H | 6-Me-5-C$_2$F$_5$ | |
| Q34 | 34-14 | 3-I | H | i-Pr | H | 6-Me-5-n-C$_3$F$_7$ | |
| Q34 | 34-15 | 3-I | H | i-Pr | H | 6-Me-5-i-C$_3$F$_7$ | |
| Q34 | 34-16 | 3-I | H | t-Bu | H | 5-i-C$_3$F$_7$ | |
| Q34 | 34-17 | 3-I | H | t-Bu | H | 5-C$_2$F$_5$ | |
| Q34 | 34-18 | 3-I | H | t-Bu | H | 5-n-C$_3$F$_7$ | |
| Q34 | 34-19 | 3-I | H | t-Bu | H | 3-Me-5-i-C$_3$F$_7$ | |

TABLE 11-continued

Q: Q34 (pyrazine structure with positions 1-N, 2, 3, 4-N, 5, 6-Ym)

($Z^1 = Z^2 = O$)

| Q | No. | Xn | $R^1$ | $R^2$ | $R^3$ | Ym | mp (° C.) |
|---|---|---|---|---|---|---|---|
| Q34 | 34-20 | 3-I | H | $CH(CH_3)CH_2SCH_3$ | H | 3-Me-5-i-$C_3F_7$ | |
| Q34 | 34-21 | 3-I | H | $CH(CH_3)CH_2SOCH_3$ | H | 3-Me-5-i-$C_3F_7$ | |
| Q34 | 34-22 | 3-I | H | $CH(CH_3)CH_2SO_2CH_3$ | H | 3-Me-5-i-$C_3F_7$ | |
| Q34 | 34-23 | 3-I | H | $C(CH_3)_2CH_2SCH_3$ | H | 3-Me-5-i-$C_3F_7$ | |
| Q34 | 34-24 | 3-I | H | $C(CH_3)_2CH_2SOCH_3$ | H | 3-Me-5-i-$C_3F_7$ | |
| Q34 | 34-25 | 3-I | H | $C(CH_3)_2CH_2SO_2CH_3$ | H | 3-Me-5-i-$C_3F_7$ | |
| Q34 | 34-26 | 3-I | H | $CH(CH_3)CH_2NHAc$ | H | 3-Me-5-i-$C_3F_7$ | |
| Q34 | 34-27 | 3-I | H | $C(CH_3)_2CH_2NHAc$ | H | 3-Me-5-i-$C_3F_7$ | |
| Q34 | 34-28 | 3-I | H | $CH(CH_3)CH_2CH_2OCH_3$ | H | 3-Me-5-i-$C_3F_7$ | |
| Q34 | 34-29 | 3-I | H | $C(CH_3)_2CH_2CH_2OCH_3$ | H | 3-Me-5-i-$C_3F_7$ | |
| Q34 | 34-30 | 3-I | Et | Et | H | H | 144 |
| Q34 | 34-31 | 3-I | Et | Et | H | 3-Me-5-$C_2F_5$ | |
| Q34 | 34-32 | 3-I | Et | Et | H | 3-Me-5-n-$C_3F_7$ | |
| Q34 | 34-33 | 3-I | Et | Et | H | 3-Me-5-i-$C_3F_7$ | |
| Q34 | 34-34 | 3-I | Et | Et | H | 5-Cl | |
| Q34 | 34-35 | 3-I | Et | Et | H | 5-Br | |
| Q34 | 34-36 | 3-I | Et | Et | H | 5-n-$C_3F_7$ | |
| Q34 | 34-37 | 3-$CF_3$ | H | i-Pr | H | 3-Me-5-$C_2F_5$ | |
| Q34 | 34-38 | 3-Ph | H | i-Pr | H | 3-Me-5-n-$C_3F_7$ | |
| Q34 | 34-39 | 3-$SOCF_3$ | H | i-Pr | H | 3-Me-5-i-$C_3F_7$ | |
| Q34 | 34-40 | 3-$C_2F_5$ | H | i-Pr | H | 3-Me-5-$C_2F_5$ | |
| Q34 | 34-41 | 3-I-4-Cl | H | i-Pr | H | 3-Me-5-n-$C_3F_7$ | |
| Q34 | 34-42 | 3-I-4-$CF_3$ | H | i-Pr | H | 3-Me-5-i-$C_3F_7$ | |
| Q34 | 34-43 | 3-$CF_3$-4-Cl | H | i-Pr | H | 3-Me-5-$C_2F_5$ | |
| Q34 | 34-44 | 3-$OCF_2O$-4 | H | i-Pr | H | 3-Me-5-n-$C_3F_7$ | |
| Q34 | 34-45 | 3-$OCF_2CF_2O$-4 | H | i-Pr | H | 3-Me-5-i-$C_3F_7$ | |
| Q34 | 34-46 | 3-I | H | Et | H | 5-i-$C_3F_7$ | 175 |
| Q3 | 3-1 | 3-I | H | i-Pr | H | H | |
| Q7 | 7-1 | 3-I | H | i-Pr | H | H | |
| Q11 | 11-1 | 3-I | H | i-Pr | H | H | |
| Q14 | 14-1 | 3-I | H | i-Pr | H | H | |
| Q15 | 15-1 | 3-I | H | i-Pr | H | H | 185 |
| Q18 | 18-1 | 3-I | H | i-Pr | H | H | |
| Q20 | 20-1 | 3-I | H | i-Pr | H | H | |

TABLE 12

Q: Q16 (imidazole-like ring with positions N, W, Ym, 4-methyl)
Q43 (benzazole structure with positions 3-N, 2, W, 1, 7, 6, 5, 4, Ym)

($Z^1 = Z^2 = O$)

| Q | No. | Xn | $R^1$ | $R^2$ | $R^3$ | W | Ym | Property, Mp (° C.) |
|---|---|---|---|---|---|---|---|---|
| Q16 | 16-1 | 3-Cl | H | i-Pr | H | N-i-Pr | SMe | Paste |
| Q16 | 16-2 | 3-Cl | H | i-Pr | H | N-n-Pr | SMe | Paste |
| Q44 | 43-1 | H | H | i-Pr | H | S | 6-Cl | 47 |

EXAMPLES

Next, typical examples of the present invention are shown below. The invention is by no means limited by these examples.

Production Example 1

(1-1) Production of N-(4-methyl-3-trifluoromethyl-isoxazol-5-yl)-3-iodophthalimide In 20 ml of acetic acid, 0.6 g of 3-iodophthalic anhydride and 0.44 g of 5-amino-4-methyl-3-trifluoromethyl-isoxazole were dissolved and reacted for 9 hours with heating under reflux. After completion of the reaction, the solvent was distilled off under reduced pressure, and the residue was dissolved in ethyl acetate, washed with dilute hydrochloric acid, saturated aqueous solution of sodium bicarbonate and saturated aqueous solution of sodium chloride, and then dried on sodium sulfate. After distilling off the solvent under reduced pressure, the residue was purified by silica gel column chromatography using a 3/1 mixture of hexane and ethyl acetate as an eluent to obtain 0.71 g of the objective product.

Property: m.p. 105° C.; Yield: 69%

(1-2) Production of $N^1$-(4-methyl-3-trifluoromethyl-isoxazol-5-yl)-$N^2$-isopropyl-3-iodophthalamide (Compound No. Q6-8)

In 50 ml of dioxane was dissolved 1.06 g of N-(4-methyl-3-trifluoromethylisoxazol-5-yl)-3-iodophthaimide. Then, 0.4 g of isopropylamine was added to the solution obtained above and stirred at room temperature for 3 hours. After completion of the reaction, the solvent was distilled off under reduced pressure, and the residue was purified by silica gel column chromatography using a 2/1 mixture of hexane and ethyl acetate as an eluent to obtain 0.32 g of the objective product.

Property: m.p. 103° C.; Yield: 26%

Production Example 2

(2-1) Production of $N^1$-[2-(1,1-dimethylethyl)-1,3,4-thiadiazol-4-yl]-$N^2$, $N^2$-diethyl-3-iodophthalamide (Compound No. Q19-34)

In 20 ml of tetrahydrofuran were dissolved 0.5 g of N,N-diethyl-3-iodophthalic acid 2-amide and 0.27 g of 5-amino-2-(1,1-dimethylethyl)-1,3,4-thiadiazole. After adding 0.28 g of diethylphosphoryl cyanide and 0.18 g of triethylamine, a reaction was carried out for 7 hours with heating under reflux. After completion of the reaction, ethyl acetate was added to the reaction mixture, and the resulting ethyl acetate solution was washed with dilute hydrochloric acid, saturated aqueous solution of sodium bicarbonate and saturated aqueous solution of sodium chloride, and dried on sodium sulfate. After distilling off the solvent, the residue was purified by silica gel column chromatography using 3/1 mixture of hexane and ethyl acetate to obtain 0.11 g of the objective product.

Property: m.p. 59° C.; Yield: 16%

Production Example 3

(3-1) Production of $N^1$-(4-methyl-2-heptafluoroisopropyl-pyridin-5-yl)-$N^2$-(1-methyl-2-methylthioethyl),-3-iodophthalamide (Compound No. Q27-144)

In 4 ml of acetonitrile were dissolved 0.37 of N-(1-methyl-2-methylthioethyl)-3-iodophthalic acid isoimide and 0.28 g of 5-amino-4-methyl-2-heptafluoro-isopropyl-pyridine. After adding a catalytic quantity of trifluoroacetic acid, the resulting mixture was stirred at room temperature for 30 minutes. The resulting crystal was collected by filtration, and there was obtained 0.28 g of the objective product.

Property: m.p. 225° C.; Yield: 44%

Production Example 4

Production of 2-amino-3-methyl-6-pentafluoroethylpyridine (Compound No. IV-1)

To 20 ml of dimethyl sulfoxide were added 2.34 g (0.01 mol) of 2-amino-5-iodo-3-methylpyridine, 2.5 g of powdered metallic copper and 3.7 g (0.015 mol) of iodopentafluoroethane. The mixture was kept at 110° C. and vigorously stirred for 6 hours. After cooling the reaction mixture to room temperature, the mixture was poured into 500 ml of ice water and thoroughly stirred. The insoluble matter was filtered off, and the objective product was extracted from the filtrate with 300 ml of ethyl acetate. The extract solution was washed with water, dried on anhydrous sodium sulfate, and concentrated under reduced pressure. Purification of the residue by column chromatography using 3/7 mixture of ethyl acetate and hexane as an eluent gave 1.1 g of the objective product (yield 20%).

$^1$H-NMR [δ(CDCl$_3$)]: 2.17 (s,3H), 4.82 (br,2H), 7.42 (d,1H), 8.16 (s,1H),

Production Example 5

Production of 3-amino-2-methoxy-6-(heptafluoropropan-2-yl)-pyridine (Compound No. IV-15)

To 20 ml of methyl t-butyl ether were added: 3.2 g (0.026 mol) of 3-amino-2-methoxypyridine, 0.6 g of triethylbenzylammonium chloride, 2.0 g of sodium carbonate and 10.0 g (0.031 mol) of 2-iodoheptafluoropropane. While stirring the mixture at 30° C., a solution of 2.8 of sodium hydrosulfite in 10 ml water was dropwise added thereto. After the dropping, the resulting mixture was reacted at room temperature for 20 hours, after which the organic layer was separated, washed with water and dried on anhydrous sodium sulfate, and the solvent was distilled off under reduced pressure. Purification of the residue by column chromatography using 3/7 mixture of ethyl acetate and hexane as an eluent gave 2.0 g of the objective product (yield 26%).

$^1$H-NMR [δ(CDCl$_3$)]: 3.96 (s,3H), 4.03 (br,2H), 6.91 (d,1H), 7.10 (dd,1H)

Production Example 6

Production of 3-amino-6-(1,1,1,3,3,3-hexafluoroisopropoxy)pyridine (Compound No. IV-27)

Sodium hydride (2.6 g) was portionwise added to a solution of 11.3 g of 1,1,1,3,3,3-hexafluoro-2-propanol in 50 ml tetrahydrofuran at a temperature not exceeding 5° C., and stirred at the same temperature as above for 30 minutes. Then, 4.7 g of 2-chloro-5-nitropyridine was added and stirred at room temperature for 12 hours. The reaction mixture was poured into 200 ml of ice water and extracted with 300 ml of ethyl acetate. The extract solution was washed with water, dried on anhydrous sodium sulfate and concentrated. Purification of the residue by column chromatography using 1/10 mixture of ethyl acetate and hexane as an eluent gave 6.2 g of 2-(1,1,1,3,3,3-hexafluoro-isopropoxy)-5-nitrobenzene (yield 64%).

To 20 ml of acetic acid were added 4.4 g of the 2-(1,1,1,3,3,3-hexafluoroisopropoxy)-5-nitrobenzene obtained above and 4.2 g of electrolytic iron. The resulting mixture was stirred at 60–65° C. for 30 minutes. The reaction mixture was cooled and neutralized with 6N aqueous solution of sodium hydroxide, the insoluble matter was filtered off, and the filtrate was extracted with 300 ml of t-butyl methyl ether. The extract solution was washed with aqueous solution of sodium chloride, dried on anhydrous sodium sulfate and concentrated. Purification of the residue by column chromatography using 2/3 mixture of ethyl acetate and hexane as an eluent gave 3.6 g of 3-amino-6-(1,1,1,3,3-hexafluoroisopropoxy)pyridine (yield 92%).

The agrohorticultural insecticides containing the phthalamide derivative of formula (I) of the present invention as an active ingredient are suitable for controlling various insect pests such as agrohorticultural insect pests, stored grain insect pests, sanitary insect pests, nematodes, etc., which are injurious to paddy rice, fruit trees, vegetables, other crops, flowers, ornamental plants, etc. They have a marked insecticidal effect, for example, on LEPIDOPTERA including summer fruit tortrix (*Adoxophyes orana fasciata*), smaller tea tortrix (*Adoxophyes* sp.), Manchurian fruit moth (*Grapholita inopinata*), oriental fruit moth (*Grapholita molesta*), soybean pod borer (*Leguminovora glycinivorella*), mulberry leafroller (*Olethreutes mori*), tea leafroller (*Caloptilia thevivora*), Caloptilia sp. (*Caloptilia zachrysa*), apple leafminer (*Phyllonorycter ringoniella*), pear barkminer (*Splerrina astaurota*), common white (*Piers rapae crucivora*), tobacco budworm (*Heliothis* sp.), codling moth (*Laspey resia pomonella*), diamondback moth (*Plutella xylostella*), apple fruit moth (*Argyresthia conjugella*) peach fruit moth (*Carposina niponensis*), rice stem borer (*Chilo suppressalis*) rice leafroller (*Cnaphalocrocis medinalis*), tobacco moth (*Ephestia elutella*), mulberry pyralid (*Glyphodes pyloalis*), yellow rice borer (*Scirpophaga incertulas*), rice skipper (*Parnara guttata*), rice armyworm (*Pseudaletia separata*), pink borer (*Sesamia inferens*), common cutworm (*Spodoptera litura*), beet armyworm (*Spodoptera exigua*), etc.; HEMIPTERA including aster leafhopper (*Macrosteles fascifrons*), green rice leafhopper (*Nephotettix cincticepts*), brown rice planthopper (*Nilaparvata lugens*), whitebacked rice planthopper (*Sogatella furcifera*), citrus psylla (*Diaphorina citri*), grape whitefly (*Aleurolibus taonabae*), sweetpotato whitefly (*Bemisia tabaci*), greenhouse whitefly (*Trialeurodes vaporariorm*), turnup aphid (*Lipaphis erysimi*), green peach aphid (*Myzus persicae*), Indian wax scale (*Ceroplastes ceriferus*), cottony citrus scale (*Pulvinaria aurantii*), camphor scale (*Pseudaonidia duplex*), san Jose scale (*Comstockaspis perniciosa*), arrowhead scale (*Unapsis yanonensis*), etc.; TYLENCHIDA including soybean beetle (*Anomala rufocuprea*), Japanese beetle (*Popillia japonica*), tobacco beetle (*Lasionderma serricorne*), powderpost beetle (*Lyctus brunneus*), twenty-eight-spotted ladybird (*Epilachna vigintiotopunctata*), azuki bean weevil (*Callosobruchus chinensis*), vegetable weevil (*Listroderes costirostris*), maize weevil (*Sitophilus zeamais*), boll weevil (*Anthonomus gradis gradis*), rice water weevil (*Lissorhoptrus oryzophilus*), cucurbit leaf beetle (*Aulacophora femoralis*), rice leaf beetle (*Oulema oryzae*), striped flea beetle (*Phyllotreta striolata*), pine shoot beetle (*Tomicus piniperda*), Colorado potato beetle (*Leptinotarsa decemlineata*), Mexican bean beetle (*Epilachna varivestis*), corn rootworm (*Diabrotica* sp.), etc.; DIPTERA including (*Dacus(Zeugodacus) cucurbitae*), oriental fruit fly (*Dacus (Bactropera) doralis*), rice leafminer (*Agnomyza oryzae*), onion maggot (*Delia antiqua*), seedcorn maggot (*Delia platura*), soybean pod gall midge (*Asphondylia* sp.), muscid fly (*Musca domestics*), house mosquito (*Culex pipiens pipiens*), etc.; and TYLENCHIDA including root-lesion nematode (*Pratylenchus* sp.), coffee root-lesion nematode (*Pratylenchus coffeae*), potato cyst nematode (*Globodera rostochiensis*), root-knot nematode (*Meloidogyne* sp.), citrus nematode (*Tylenchulus semipenetrans*), *Aphelenchus* sp. (*Aphelenchus avenae*), chrysanthemum foliar (*Aphelenchoides ritzemabosi*), etc.

The agrohorticultural agent and particularly the agrohorticultural insecticide containing the phthalamide derivative represented by formula (I) of the present invention has a marked controlling effect on the above-exemplified insect pests, sanitary pests and/or nematodes, which are injurious to paddy field crops, upland crops, fruit trees, vegetables and other crops, flowers and ornament plants, and the like. Therefore, the desired effect of the agrohorticultural insecticide of the present invention can be exhibited by applying the insecticide to the paddy field water, stalks and leaves or soil of paddy field, upland field, fruit trees, vegetables, other crops or flowers and ornament plants at a season at which the insect pests, sanitary pests or nematodes are expected to appear, before their appearance or at the time when their appearance is confirmed.

In general, the agrohorticultural agent of the present invention is used after being prepared into conveniently usable forms according to ordinary manner for preparation of agrochemicals.

That is, the phthalamide derivative of in formula (I) and an appropriate carrier are blended optionally together with an adjuvant in a proper proportion and prepared into a suitable preparation form such as suspension, emulsifiable concentrate, soluble concentrate, wettable powder, granules, dust or tablets through dissolution, separation, suspension, mixing, impregnation, adsorption or sticking.

The inert carrier used in the present invention may be either solid or liquid. As the solid carrier, soybean flour, cereal flour, wood flour, bark flour, saw dust, powdered tobacco stalks, powdered walnut shells, bran, powdered cellulose, extraction residues of vegetables, powdered synthetic polymers or resins, clay (e.g. kaolin, bentonite and acid clay), talc (e.g. talc and pyrophyllite), silica materials (e.g. diatomaceous earth, siliceous sand, mica, white carbon, i.e. synthetic high-dispersion silicic acid, also called finely divided hydrated silica or hydrated silicic acid, some of the commercially available products contain calcium silicate as the major component), activated carbon, powdered sulfur, pumice, calcined diatomaceous earth, ground brick, fly ash, sand, calcium carbonate, calcium phosphate and other inorganic or mineral powders, chemical fertilizers such as ammonium sulfate, ammonium phosphate, ammonium nitrate, urea, ammonium chloride and the like, and compost. These carriers may be used either alone or as a mixture of two or more carriers.

The liquid carrier is that which itself has a solubility or which is without such solubility but is capable of dispersing an active ingredient with the aid of an adjuvant. The following are typical examples of the liquid carrier and can be used alone or as a mixture thereof. Water; alcohols such as methanol, ethanol, isopropanol, butanol and ethylene glycol; ketones such as acetone, methyl ethyl ketone, methyl isobutyl ketone, diisobutyl ketone and cyclohexanone; ethers such as ethyl ether, dioxane, cellosolve, dipropyl ether and tetrahydrofuran; aliphatic hydrocarbons such as kerosene and mineral oil; aromatic hydrocarbons such as benzene, toluene, xylene, solvent naphtha and alkylnaphthalene; halogenated hydrocarbons such as dichlorethane, chloroform, carbon tetrachloride and chlorobenzene; esters such as ethyl acetate, diisopropyl phthalate, dibutyl phthalate and dioctyl phthalate; amides such as dimethylformamide, diethylformamide and dimethylacetamide; nitriles such as acetonitrile; and dimethyl sulfoxide.

The following are typical examples of the adjuvant, which are used depending upon purposes and used alone or in combination of two or more adjuvants in some cases, or need not to be used at all.

To emulsify, disperse, dissolve and/or wet an active ingredient, a surfactant is used. As the surfactant, there can be exemplified polyoxyethylene alkyl ethers, polyoxyethylene alkylaryl ethers, polyoxyethylene higher fatty acid esters, polyoxyethylene resinates, polyoxyethylene sorbitan monolaurate, polyoxyethylene sorbitan monooleate, alkylarylsulfonates, naphthalene-sulfonic acid condensation products, ligninsulfonates and higher alcohol sulfate esters.

Further, to stabilize the dispersion of an active ingredient, tackify it and/or bind it, there may be used adjuvants such as casein, gelatin, starch, methyl cellulose, carboxymethyl cellulose, gum arabic, polyvinyl alcohols, turpentine, bran oil, bentonite and ligninsulfonates.

To improve the flowability of a solid product, there may be used adjuvants such as waxes, stearates and alkyl phosphates.

Adjuvants such as naphthalenesulfonic acid condensation products and polycondensates of phosphates may be used as a peptizer for dispersible products.

Adjuvants such as silicone oil may also be used as a defoaming agent.

The content of the active ingredient may be varied according to the need, in a range of 0.01 to 80 parts by weight per 100 parts by weight of the preparation. In dusts or granules, the suitable content thereof is from 0.01 to 50% by weight. In emulsifiable concentrate and flowable wettable powder, too, the suitable content is from 0.01 to 50% by weight.

The agrohorticultural insecticide of the present invention is used to control a variety of insect pests in the following manner. That is, it is applied to a crop on which the insect pests are expected to appear or a site where appearance of the insect pests is undesirable, as it is or after being properly diluted with or suspended in water or the like, in an amount effective for control of the insect pests.

The applying dosage of the agrihorticultural insecticide of the present invention is varied depending upon various factors such as a purpose, insect pests to be controlled, a growth state of a plant, tendency of insect pests appearance, weather, environmental conditions, a preparation form, an application method, an application site and an application time. It may be properly chosen in a range of 0.1 g to 10 kg (in terms of active ingredient compound) per 10 ares depending upon purposes.

The agrihorticultural insecticide of the present invention may be used in admixture with other agricultural and horticultural disease or pest controllers in order to expand both spectrum of controllable diseases and insect pest species and the period of time when effective applications are possible or to reduce the dosage.

Next, typical formulation examples and test examples of the invention are presented below. The present invention is by no means limited by these examples.

In the formulation examples, the term "parts" means "parts by weight".

Formulation Example 1

| | |
|---|---|
| Each compound listed in Tables 2 to 12 | 50 parts |
| Xylene | 40 parts |
| Mixture of polyoxyethylene nonylphenyl ether and calcium alkylbenzenesulfonate | 10 parts |

An emulsifiable concentrate was prepared by mixing uniformly the above ingredients to effect dissolution.

Formulation Example 2

| | |
|---|---|
| Each compound listed in Tables 2 to 12 | 3 parts |
| Clay powder | 82 parts |
| Diatomaceous earth powder | 15 parts |

A dust was prepared by mixing uniformly and grinding the above ingredients.

Formulation Example 3

| | |
|---|---|
| Each compound listed in Tables 2 to 12 | 5 parts |
| Mixed powder of bentonite and clay | 90 parts |
| Calcium ligninsulfonate | 5 parts |

Granules were prepared by mixing the above ingredients uniformly, and kneading the resulting mixture together with a suitable amount of water, followed by granulation and drying.

Formulation Example 4

| | |
|---|---|
| Each compound listed in Tables 2 to 12 | 20 parts |
| Mixture of kaolin and synthetic high-dispersion silicic acid | 75 parts |
| Mixture of polyoxyethylene nonylphenyl ether and calcium alkylbenzenesulfonate | 5 parts |

A wettable powder was prepared by mixing uniformly and grinding the above ingredients.

Test Example 1

Insecticidal effect on diamond back moth (*Plutella xylostella*)

Adult diamond back moths were released and allowed to oviposit on a Chinese cabbage seedling. Two days after the release, the seedling having the eggs deposited thereon was immersed for about 30 seconds in a liquid chemical prepared by diluting a preparation containing each compound listed in Tables 2 to 12 as an active ingredient to adjust the concentration to 1,000 ppm. After air-dryness, it was allowed to stand in a room thermostatted at 25° C. Six days after the immersion, the hatched insects were counted. The mortality was calculated according to the following equation and the insecticidal effect was judged according to the criterion shown below. The test was carried out with triplicate groups of 10 insects.

$$\text{Corrected mortality}(\%) = \frac{\begin{array}{c}\text{Number of} \\ \text{hatched insects} \\ \text{in untreated group}\end{array} - \begin{array}{c}\text{Number of} \\ \text{hatched insects} \\ \text{in treated group}\end{array}}{\begin{array}{c}\text{Number of} \\ \text{hatched insects} \\ \text{in untreated group}\end{array}} \times 100$$

Criterion

A - - - Mortality 100%
B - - - Mortality 99–90%
C - - - Mortality 89–80%
D - - - Mortality 79–50%

In the test mentioned above, the compounds which exhibited an activity ranking B or higher were as follows:

Q1-12, Q1-41, Q1-42, Q4-6, Q4-8, Q4-12, Q4-45, Q6-6, Q6-8, Q8-1, Q8-2, Q8-3, Q8-5, Q8-11, Q8-13, Q8-14, Q8-15, Q8-53, Q9-15, Q10-7, Q15-1, Q26-1, Q26-11, Q26-29, Q26-30, Q26-31, Q26-32, Q26-33, Q26-43, Q27-29, Q27-30, Q27-31, Q27-32, Q27-81, Q27-98, Q27-124, Q27-125, Q27-126, Q27-127, Q27-128, Q27-129, Q27-130, Q27-131, Q27-132, Q27-133, Q27-134, Q27-135, Q27-136, Q27-137, Q27-138, Q27-139, Q27-140, Q27-141, Q27-142, Q27-143, Q27-144, Q27-145, Q27-150, Q27-151, Q27-153, Q27-155, Q27-164, Q27-230, Q27-231, Q27-232, Q27-233, Q27-234, Q27-235, Q27-236, Q27-238, Q27-239, Q27-240, Q27-241, Q27-242, Q27-243, Q27-244, Q27-245, Q27-246, Q27-247, Q27-248 to Q27-265, Q27-267, Q27-268, Q27-270, Q27-273 to Q27-280, Q27-282 to Q27-284, Q27-289, Q27-297, Q27-298, Q27-305 to Q27-309, Q27-316 to Q27-318, Q27-323 to Q27-327, Q27-332, Q27-334, Q27-335, Q27-336 to Q27-339, Q27-347, Q27-352, Q27-353, Q27-354, Q27-355, Q27-359, Q27-360, Q27-378, Q27-384, Q27-387, Q27-388, Q27-391, Q27-393, Q27-396, Q27-397, Q27-402 to Q27-405, Q27-407, Q27-413, Q27-414, Q27-439, Q27-449 to Q27-457, Q27-459 to Q27-469, Q32-11, Q32-19, Q33-1, Q33-10, Q34-30, Q34-46 and Q42-1.

Test Example 2
Insecticidal Effect on Common cutworm (*Spodoptera litura*)

A piece of cabbage leaf (cultivar; Shikidori) was immersed for about 30 seconds in a liquid chemical prepared by diluting a preparation containing each compound listed in Tables 2 to 12 as an active ingredient to adjust the concentration to 500 ppm. After air-dryness, it was placed in a plastic Petri dish with a diameter of 9 cm and inoculated with second-instar larvae of common cutworm, after which the dish was closed and then allowed to stand in a room thermostatted at 25° C. Eight days after the inoculation, the dead and alive were counted. The mortality was calculated according to the following equation and the insecticidal effect was judged according to the criterion shown in Test Example 1. The test was carried out with triplicate groups of 10 insects.

$$\text{Corrected mortality}(\%) = \frac{\text{Number of alive larvae in untreated group} - \text{Number of alive larvae in treated group}}{\text{Number of alive larvae in untreated group}} \times 100$$

In the test mentioned above, the compounds which exhibited an activity ranking B or higher were as follows:

Q26-1, Q26-11, Q26-29, Q26-30, Q26-31, Q26-32, Q26-33, Q26-43, Q27-29, Q27-30, Q27-31, Q27-32, Q27-81, Q27-98, Q27-124, Q27-125, Q27-126, Q27-127, Q27-128, Q27-129, Q27-130, Q27-131, Q27-132, Q27-133, Q27-134, Q27-135, Q27-136, Q27-137, Q27-138, Q27-139, Q27-140, Q27-141, Q27-142, Q27-143, Q27-144, Q27-145, Q27-150, Q27-151, Q27-152, Q27-153, Q27-155, Q27-164, Q27-230, Q27-231, Q27-232, Q27-233, Q27-234, Q27-235, Q27-236, Q27-238, Q27-239, Q27-240, Q27-241, Q27-242, Q27-243, Q27-244, Q27-245, Q27-246, Q27-247, Q27-248 to Q27-265, Q27-267, Q27-268, Q27-270, Q27-273 to Q27-280, Q27-282 to Q27-284, Q27-289, Q27-297, Q27-298, Q27-305 to Q27-309, Q27-316 to Q27-318, Q27-323 to Q27-327, Q27-332, Q27-334, Q27-335, Q27-336 to Q27-339, Q27-347, Q27-352, Q27-353, Q27-354, Q27-355, Q27-359, Q27-360, Q27-378, Q27-384, Q27-387, Q27-388, Q27-397, Q27-402 to Q27-405, Q27-407, Q27-413, Q27-414, Q27-439, Q27-459, Q27-466, Q32-19 and Q34-46.

Test Example 3
Insecticidal effect on rice leafroller (*Cnaphalocrosis medinalis*)

The lamina of a rice plant at the 6 to 8 leaf stage was immersed for about 30 seconds in a liquid chemical prepared by diluting a preparation containing each compound listed in Tables 2 to 12 as an active ingredient to adjust the concentration to 500 ppm. After air-dryness, the lamina was placed in a plastic Petri dish with a diameter of 9 cm whose bottom had been covered with a wetted filter paper. The lamina was inoculated with third-instar larvae of rice leafroller, after which the dish was allowed to stand in a room thermostatted at 25° C. and having a humidity of 70%. Four days after the inoculation, the dead and alive were counted and the insecticidal effect was judged according to the criterion shown in Test Example 1. The test was carried out with triplicate groups of 10 insects.

In the test mentioned above, compounds which exhibited an activity ranking B or higher were as follows:

Q26-1, Q26-29, Q26-30, Q26-31, Q26-32, Q26-33, Q27-29, Q27-30, Q27-31, Q27-32, Q27-81, Q27-98, Q27-124, Q27-125, Q27-126, Q27-127, Q27-128, Q27-129, Q27-130, Q27-131, Q27-132, Q27-133, Q27-134, Q27-135, Q27-136, Q27-137, Q27-138, Q27-139, Q27-140, Q27-141, Q27-142, Q27-143, Q27-144, Q27-145 and Q27-164.

What is claimed is:

1. A phthalamide derivative represented by the following formula (I):

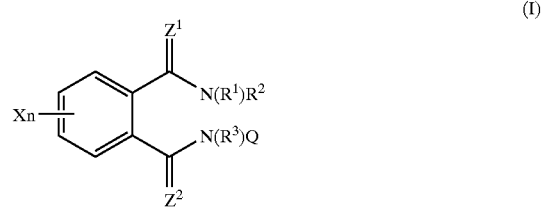

wherein $R^1$, $R^2$ and $R^3$, which may be same or different, represent hydrogen atom, $C_3$–$C_6$ cycloalkyl group, halo $C_3$–$C_6$ cycloalkyl group or —$A^1$—$(G)_r$ (in this formula, $A^1$ represents $C_1$–$C_8$ alkylene group, $C_3$–$C_6$ alkenylene group or $C_3$–$C_6$ alkynylene group; G, which may be same or different, represents hydrogen atom, halogen atom, cyano group, nitro group, halo $C_1$–$C_6$ alkyl group, $C_3$–$C_6$ cycloalkyl group, halo $C_3$–$C_6$ cycloalkyl group, $C_1$–$C_6$ alkoxycarbonyl group, di($C_1$–$C_6$)alkoxyphosphoryl group in which the ($C_1$–$C_6$)alkoxy groups may be same or different, di($C_1$–$C_6$)alkoxythiophosphoryl group in which the ($C_1$–$C_6$) alkoxy groups may be same or different, diphenylphosphino group, diphenylphosphono group, phenyl group, substituted phenyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group (as used herein, the term "heterocyclic group" means pyridyl group, pyridine-N-oxide group, pyrimidinyl group, furyl group, tetrahydrofuryl group, thienyl group, tetrahydrothienyl group, tetrahydropyranyl group, oxazolyl group, isoxazolyl group, oxadiazolyl group, thiazolyl group, isothiazolyl group, thiadiazolyl group, imidazolyl group, triazolyl group or pyrazolyl group), substituted heterocyclic group (the term heterocyclic group is as defined above) having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, or —$Z^3$—$R^4$ (in this formula, $Z^3$ represents —O—, —S—, —SO—, —$SO_2$—, —$N(R^5)$— (in this formula, $R^5$ represents hydrogen atom, $C_1$–$C_6$ alkylcarbonyl group, halo $C_1$–$C_6$ alkylcarbonyl group, $C_1$–$C_6$ alkoxycarbonyl group, phenylcarbonyl group, substituted phenylcarbonyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, phenyl $C_1$–$C_4$ alkoxycarbonyl group, substituted phenyl $C_1$–$C_4$ alkoxycarbonyl group having, on the ring thereof, at least one, same or different substituents selected from the group consisting of halogen atom, C$_1$–C$_6$ alkyl group, halo C$_1$–C$_6$ alkyl group, C$_1$–C$_6$ alkoxy group, halo C$_1$–C$_6$ alkoxy group, C$_1$–C$_6$ alkylthio group, halo C$_1$–C$_6$ alkylthio group, C$_1$–C$_6$ alkylsulfinyl group, halo C$_1$–C$_6$ alkylsulfinyl group, C$_1$–C$_6$ alkylsulfonyl group and halo C$_1$–C$_6$ alkylsulfonyl group), C$_1$–C$_6$ alkylsulfonyl group or halo C$_1$–C$_6$ alkylsulfonyl group), —C(=O)— or —C(=NOR$^6$)— (in this formula, R$^6$ represents hydrogen atom, C$_1$–C$_6$ alkyl group, halo C$_1$–C$_6$ alkyl group, C$_3$–C$_6$ alkenyl group, halo C$_3$–C$_6$ alkenyl group, C$_3$–C$_6$ alkynyl group, C$_3$–C$_6$ cycloalkyl group, phenyl C$_1$–C$_4$ alkyl group, or substituted phenyl C$_1$–C$_4$ alkyl group having, on the ring thereof, at least one, same or different substituents selected from the group consisting of halogen atom, C$_1$–C$_6$ alkyl group, halo C$_1$–C$_6$ alkyl group, C$_1$–C$_6$ alkoxy group, halo C$_1$–C$_6$ alkoxy group, C$_1$–C$_6$ alkylthio group, halo C$_1$–C$_6$ alkylthio group, C$_1$–C$_6$ alkylsulfinyl group, halo C$_1$–C$_6$ alkylsulfinyl group, C$_1$–C$_6$ alkylsulfonyl group and halo C$_1$–C$_6$ alkylsulfonyl group), and R$^4$ represents hydrogen atom, C$_1$–C$_6$ alkyl group, halo C$_1$–C$_6$ alkyl group, C$_3$–C$_6$ alkenyl group, halo C$_3$–C$_6$ alkenyl group, C$_3$–C$_6$ alkynyl group, halo C$_3$–C$_6$ alkynyl group, C$_3$–C$_6$ cycloalkyl group, halo C$_3$–C$_6$ cycloalkyl group, C$_1$–C$_6$ alkoxy C$_1$–C$_6$ alkyl group, C$_1$–C$_6$ alkylthio C$_1$–C$_6$ alkyl group, formyl group, C$_1$–C$_6$ alkylcarbonyl group, halo C$_1$–C$_6$ alkylcarbonyl group, C$_1$–C$_6$ alkoxycarbonyl group, mono (C$_1$–C$_6$)alkylaminocarbonyl group, di(C$_1$–C$_6$) alkylaminocarbonyl group in which the (C$_1$–C$_6$)alkyl groups may be same or different, mono(C$_1$–C$_6$) alkylaminothiocarbonyl group, di(C$_1$–C$_6$)alkylaminothiocarbonyl group in which the (C$_1$–C$_6$)alkyl groups may be same or different, di(C$_1$–C$_6$)alkoxyphosphoryl group in which the (C$_1$–C$_6$) alkoxy groups may be same or different, di(C$_1$–C$_6$) alkoxythiophosphoryl group in which the (C$_1$–C$_6$)alkoxy groups may be same or different, phenyl group, substituted phenyl group having at least one, same or different substituents selected from the group consisting of halogen atom, C$_1$–C$_6$ alkyl group, halo C$_1$–C$_6$ alkyl group, C$_1$–C$_6$ alkoxy group, halo C$_1$–C$_6$ alkoxy group, C$_1$–C$_6$ alkylthio group, halo C$_1$–C$_6$ alkylthio group, C$_1$–C$_6$ alkylsulfinyl group, halo C$_1$–C$_6$ alkylsulfinyl group, C$_1$–C$_6$ alkylsulfonyl group and halo C$_1$–C$_6$ alkylsulfonyl group, phenyl C$_1$–C$_4$ alkyl group, substituted phenyl (C$_1$–C$_4$)alkyl group having, on the ring thereof, at least one, same or different substituents selected from the group consisting of halogen atom, C$_1$–C$_6$ alkyl group, halo C$_1$–C$_6$ alkyl group, C$_1$–C$_6$ alkoxy group, halo C$_1$–C$_6$ alkoxy group, C$_1$–C$_6$ alkylthio group, halo C$_1$C$_6$ alkylthio group, C$_1$–C$_6$ alkylsulfinyl group, halo C$_1$–C$_6$ alkylsulfinyl group, C$_1$–C$_6$ alkylsulfonyl group and halo C$_1$–C$_6$ alkylsulfonyl group, heterocyclic group (the term heterocyclic group is as defined above), or substituted heterocyclic group (the term heterocyclic group is as defined above) having at least one, same or different substituents selected from the group consisting of halogen atom, C$_1$–C$_6$ alkyl group, halo C$_1$–C$_6$ alkyl group, C$_1$–C$_6$ alkoxy group, halo C$_1$–C$_6$ alkoxy group, C$_1$–C$_6$ alkylthio group, halo C$_1$–C$_6$ alkylthio group, C$_1$–C$_6$ alkylsulfinyl group, halo C$_1$–C$_6$ alkylsulfinyl group, C$_1$–C$_6$ alkylsulfonyl group and halo C$_1$–C$_6$ alkylsulfonyl group); and r represents an integer of 1 to 4); further, R$^1$ and R$^2$ may be taken conjointly with the N to which they are attached to form 4- to 7-membered rings which may be intercepted by 1 to 3, same or different oxygen atom, sulfur atom or nitrogen atom;

X, which may be same or different, represents halogen atom, cyano group, nitro group, amino group, C$_1$–C$_6$ alkyl group, halo C$_1$–C$_6$ alkyl group, C$_3$–C$_6$ cycloalkyl group, halo C$_3$–C$_6$ cycloalkyl group, C$_1$–C$_6$ alkoxy group, halo C$_1$–C$_6$ alkoxy group, C$_1$–C$_6$ alkylthio group, halo C$_1$–C$_6$ alkylthio group, C$_1$–C$_6$ alkylsulfinyl group, halo C$_1$–C$_6$ alkylsulfinyl group, C$_1$–C$_6$ alkylsulfonyl group, halo C$_1$–C$_6$ alkylsulfonyl group, mono (C$_1$–C$_6$)alkylamino group, di(C$_1$–C$_6$)alkylamino group in which the (C$_1$–C$_6$)alkyl groups may be same or different, C$_1$–C$_6$ alkylcarbonylamino group, halo C$_1$–C$_6$ alkylcarbonylamino group, C$_1$–C$_6$ alkoxycarbonyl group, or tri(C$_1$–C$_6$)alkylsilylethynyl group in which the (C$_1$–C$_6$)alkyl groups may be same or different; and n represents an integer of 1 to 4; further, X may be taken conjointly with the adjacent carbon atom on the phenyl ring to form a fused ring (as used herein, the term fused ring means naphthalene, tetrahydronaphthalene, indene, indane, quinoline, quinazoline, chroman, isochroman, indole, indoline, benzodioxane, benzodioxole, benzofuran, dihydrobenzofuran, benzothiophene, dihydrobenzothiophene, benzoxazole, benzothiazole, benzimidazole or indazole), and said fused ring may have at least one, same or different substituents selected from the group consisting of halogen atom, C$_1$–C$_6$ alkyl group, halo C$_1$–C$_6$ alkyl group, C$_1$–C$_6$ alkoxy group, halo C$_1$–C$_6$ alkoxy group, C$_1$–C$_6$ alkylthio group, halo C$_1$–C$_6$ alkylthio group, C$_1$–C$_6$ alkylsulfinyl group, halo C$_1$–C$_6$ alkylsulfinyl group, C$_1$–C$_6$ alkylsulfonyl group, halo C$_1$–C$_6$ alkylsulfonyl group, phenyl group, substituted phenyl group having at least one, same or different substituents selected from the group consisting of halogen atom, C$_1$–C$_6$ alkyl group, halo C$_1$–C$_6$ alkyl group, C$_1$–C$_6$ alkoxy group, halo C$_1$–C$_6$ alkoxy group, C$_1$–C$_6$ alkylthio group, halo C$_1$–C$_6$ alkylthio group, C$_1$–C$_6$ alkylsulfinyl group, halo C$_1$–C$_6$ alkylsulfinyl group, C$_1$–C$_6$ alkylsulfonyl group and halo C$_1$–C$_6$ alkylsulfonyl group, heterocyclic group (the term heterocyclic group is as defined above), and substituted heterocyclic group (the term heterocyclic group is as defined above) having at least one, same or different substituents selected from the group consisting of halogen atom, C$_1$–C$_6$ alkyl group, halo C$_1$–C$_6$ alkyl group, C$_1$–C$_6$ alkoxy group, halo C$_1$–C$_6$ alkoxy group, C$_1$–C$_6$ alkylthio group, halo C$_1$–C$_6$ alkylthio group, C$_1$–C$_6$ alkylsulfinyl group, halo C$_1$–C$_6$ alkylsulfinyl group, C$_1$–C$_6$ alkylsulfonyl group and halo C$_1$–C$_6$ alkylsulfonyl group;

Q represents an optionally substituted, heterocyclic or fused heterocyclic group, having one of the following formulas Q26, Q27, or Q28:

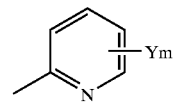

Q26

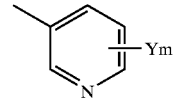

Q27

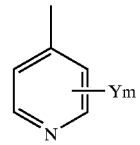

Q28

(in these formulas, Y, which may be same or different, represents halogen atom, cyano group, nitro group, $C_1$–$C_6$ alkyl group, halo $C_1$–$C_6$ alkyl group, halo $C_3$–$C_6$ cycloalkyl group, $C_1$–$C_6$ alkoxy group, halo $C_1$–$C_6$ alkoxy group, halo $C_1$–$C_6$ alkoxy halo $C_1$–$C_6$ alkoxy group, $C_1$–$C_6$ alkylthio group, halo $C_1$–$C_6$ alkylthio group, halo $C_1$–$C_6$ alkoxy halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, phenyl group, substituted phenyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, phenoxy group, substituted phenoxy group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group (the term heterocyclic group is as defined above), or substituted heterocyclic group (the term heterocyclic group is as defined above) having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group; and m represents an integer of 0 to 4;

alternatively, Y may be taken conjointly with adjacent carbon atom on the ring to form a fused ring (the fused ring is as defined above), and said fused ring may have at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, phenyl group, substituted phenyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group (the term heterocyclic group is as defined above), and substituted heterocyclic group (the term heterocyclic group is as defined above) having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group; and $Z^1$ and $Z^2$ represent oxygen atom or sulfur atom.

2. A heterocyclic amine derivative represented by the following formula (IV'):

$$Q'\text{—}NH_2 \qquad (IV')$$

wherein:

(1) in cases where Q' represents Q26,

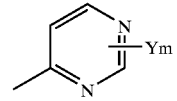

(Q26)

Y, which may be same or different, represents halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkyl-sulfonyl group or halo $C_1$–$C_6$ alkylsulfonyl group, m represents an integer of 1 to 4, and at least one of Y, of which total number is m, is perfluoro $C_3$–$C_6$ alkyl group; and (2) in a case where Q' represents Q27:

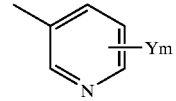

(Q27)

Y, which may be same or different, represents halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkyl-sulfonyl group or halo $C_1$–$C_6$ alkylsulfonyl group, m represents an integer of 1 to 4, and at least one of Y, of which total number is m, is perfluoro $C_2$–$C_6$ alkyl group, halo $C_1$–$C_6$ alkoxy group or halo $C_1$–$C_6$ alkylthio group.

3. An agrohorticultural insecticide containing, as an active ingredient thereof, a phthalamide derivative represented by the following formula (I):

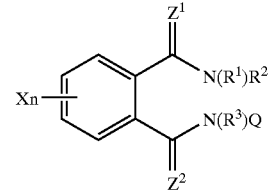

(I)

wherein $R^1$, $R^2$ and $R^3$, which may be same or different, represent hydrogen atom, $C_3$–$C_6$ cycloalkyl group, halo $C_3$–$C_6$ cycloalkyl group or —$A^1$—$(G)_r$ (in this formula, $A^1$ represents $C_1$–$C_8$ alkylene group, $C_3$–$C_6$ alkenylene group or $C_3$–$C_6$ alkynylene group; G, which may be same or different, represents hydrogen atom, halogen atom, cyano group, nitro group, halo $C_1$–$C_6$ alkyl group, $C_3$–$C_6$ cycloalkyl group, halo $C_3$–$C_6$ cycloalkyl group, $C_1$–$C_6$ alkoxycarbonyl group, di($C_1$–$C_6$)alkoxyphosphoryl group in which the ($C_1$–$C_6$)alkoxy groups may be same or different, di($C_1$–$C_6$) alkoxythiophosphoryl group in which the ($C_1$–$C_6$)alkoxy groups may be same or different, diphenylphosphino group, diphenylphosphono group, phenyl group, substituted phenyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group (as used herein, the term "heterocyclic group" means pyridyl group, pyridine-N-oxide group, pyrimidinyl group, furyl group, tetrahydrofuryl group, thienyl group, tetrahydrothienyl group, tetrahydropyranyl group, oxazolyl group, isoxazolyl group, oxadiazolyl group, thiazolyl group, isothiazolyl group, thiadiazolyl group, imidazolyl group, triazolyl group or pyrazolyl group), substituted heterocyclic group (the term heterocyclic group is as defined above) having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, or —$Z^3$—$R^4$ (in this formula, $Z^3$ represents —O—, —S—, —SO—, —$SO_2$—, —$N(R^5)$— (in this formula, $R^5$ represents hydrogen atom, $C_1$–$C_6$ alkylcarbonyl group, halo $C_1$–$C_6$ alkylcarbonyl group, $C_1$–$C_6$ alkoxycarbonyl group, phenylcarbonyl group, substituted phenylcarbonyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, phenyl $C_1$–$C_4$ alkoxycarbonyl group, substituted phenyl $C_1$–$C_4$ alkoxycarbonyl group having, on the ring thereof, at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, $C_1$–$C_6$ alkylsulfonyl group or halo $C_1$–$C_6$ alkylsulfonyl group), —C(=O)— or —C(=$NOR^6$)— (in this formula, $R^6$ represents hydrogen atom, $C_1$–$C_6$ alkyl group, halo $C_1$–$C_6$ alkyl group, $C_3$–$C_6$ alkenyl group, halo $C_3$–$C_6$ alkenyl group, $C_3$–$C_6$ alkynyl group, $C_3$–$C_6$ cycloalkyl group, phenyl $C_1$–$C_4$ alkyl group, or substituted phenyl $C_1$–$C_4$ alkyl group having, on the ring thereof, at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group), and $R^4$ represents hydrogen atom, $C_1$–$C_6$ alkyl group, halo $C_1$–$C_6$ alkyl group, $C_3$–$C_6$ alkenyl group, halo $C_3$–$C_6$ alkenyl group, $C_3$–$C_6$ alkynyl group, halo $C_3$–$C_6$ alkynyl group, $C_{3-C_6}$ cycloalkyl group, halo $C_3$–$C_6$ cycloalkyl group, $C_1$–$C_6$ alkoxy $C_1$–$C_6$ alkyl group, $C_1$–$C_6$ alkylthio $C_1$–$C_6$ alkyl group, formyl group, $C_1$–$C_6$ alkylcarbonyl group, halo $C_1$–$C_6$ alkylcarbonyl group, $C_1$–$C_6$ alkoxycarbonyl group, mono($C_1$–$C_6$)alkylaminocarbonyl group, di($C_1$–$C_6$) alkylaminocarbonyl group in which the ($C_1$–$C_6$)alkyl groups may be same or different, mono($C_1$–$C_6$) alkylaminothiocarbonyl group, di($C_1$–$C_6$) alkylaminothiocarbonyl group in which the ($C_1$–$C_6$)alkyl groups may be same or different, di($C_1$–$C_6$) alkoxyphosphoryl group in which the ($C_1$–$C_6$)alkoxy groups may be same or different, di($C_1$–$C_6$)alkoxythiophosphoryl group in which the ($C_1$–$C_6$)alkoxy groups may be same or different, phenyl group, substituted phenyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, phenyl $C_1$–$C_4$ alkyl group, substituted phenyl ($C_1$–$C_4$)alkyl group having, on the ring thereof, at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group (the term heterocyclic group is as defined above), or substituted heterocyclic group (the term heterocyclic group is as defined above) having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group); and r represents an integer of 1 to 4); further, $R^1$ and $R^2$ may be taken conjointly with the N to which they are attached to form 4- to 7-membered rings which may be intercepted by 1 to 3, same or different oxygen atom, sulfur atom or nitrogen atom;

X, which may be same or different, represents halogen atom, cyano group, nitro group, $C_3$–$C_6$ cycloalkyl group, halo $C_3$–$C_6$ cycloalkyl group, phenyl group, substituted phenyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group (the term heterocyclic group is as defined above), substituted heterocyclic group (the term heterocyclic group is as defined above) having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, or —$A^2$—$R^7$ n represents an integer of 0 to 4; further, X may be taken conjointly with the adjacent carbon atom on the phenyl ring to form a fused ring (as used herein, the term fused ring means naphthalene, tetrahydronaphthalene, indene, indane, quinoline, quinazoline, chroman, isochroman, indole, indoline, benzodioxane, benzodioxole, benzofuran, dihydrobenzofuran, benzothiophene, dihydrobenzothiophene, benzoxazole, benzothiazole, benzimidazole or indazole), and said fused ring may have at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, phenyl group, substituted phenyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group (the term heterocyclic group is as defined above), and substituted heterocyclic group (the term heterocyclic group is as defined above) having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group;

Q represents an N—, S— or O—containing, optionally substituted, heterocyclic group or fused heterocyclic group, selected from the group consisting of the following formulas Q26 to Q28 and Q46;

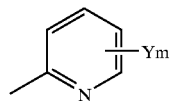
Q26

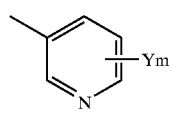
Q27

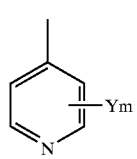
Q28

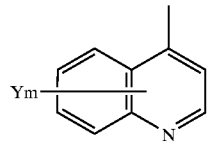
Q46

(in these formulas, Y, which may be same or different, represents halogen atom, cyano group, nitro group, halo $C_3$–$C_6$ cycloalkyl group, phenyl group, substituted phenyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group (the term heterocyclic group is as defined above), substituted heterocyclic group (the term heterocyclic group is as defined above) having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, or —$A^2$—$R^7$ (in this formula, $A^2$ and $R^7$ are as defined above); m represents an integer of 0 to 6;

alternatively, Y may be taken conjointly with adjacent carbon atom on the ring to form a fused ring (the fused ring is as defined above), and said fused ring may have at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, phenyl group, substituted phenyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group (the term heterocyclic group is as defined above), and substituted heterocyclic group (the term heterocyclic group is as defined above) having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group;

and $Z^1$ and $Z^2$ represent oxygen atom or sulfur atom.

4. An agrihorticultural insecticide according to claim 3, wherein $R^1$, $R^2$ and $R^3$, which may be same or different, represent hydrogen atom, $C_3$–$C_6$ cycloalkyl group, halo $C_3$–$C_6$ cycloalkyl group or —$A^1$—$(G)_r$ (in this formula, $A^1$ represents $C_1$–$C_8$ alkylene group, $C_3$–$C_6$ alkenylene group or $C_3$–$C_6$ alkynylene group; G, which may be same or different, represents hydrogen atom, halogen atom, cyano group, nitro group, halo $C_1$–$C_6$ alkyl group, $C_3$–$C_6$ cycloalkyl group, halo $C_3$–$C_6$ cycloalkyl group, $C_1$–$C_6$ alkoxycarbonyl group, di($C_1$–$C_6$)alkoxyphosphoryl group in which the ($C_1$–$C_6$)alkoxy groups may be same or different, di($C_1$–$C_6$)alkoxythiophosphoryl group in which the ($C_1$–$C_6$) alkoxy groups may be same or different, diphenylphosphino group, diphenylphosphono group, phenyl group, substituted phenyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group (as used herein, the term "heterocyclic group" means pyridyl group, pyridine-N-oxide group, pyrimidinyl group, furyl group, tetrahydrofuryl group, thienyl group, tetrahydrothienyl group, tetrahydropyranyl group, oxazolyl group, isoxazolyl group, oxadiazolyl group, thiazolyl group, isothiazolyl group, thiadiazolyl group, imidazolyl group, triazolyl group or pyrazolyl group), substituted heterocyclic group (the term heterocyclic group is as defined above) having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, or —$Z^3$—$R^4$ (in this formula, $Z^3$ represents —O—, —S—, —SO—, —$SO_2$—, —$N(R^5)$— (in this formula, $R^5$ represents hydrogen atom, $C_1$–$C_6$ alkylcarbonyl group, halo $C_1$–$C_6$ alkylcarbonyl group, $C_1$–$C_6$ alkoxycarbonyl group, phenylcarbonyl group, substituted phenylcarbonyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, phenyl $C_1$–$C_4$ alkoxycarbonyl group, substituted phenyl $C_1$–$C_4$ alkoxycarbonyl group having, on the ring thereof, at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, $C_1$–$C_6$ alkylsulfonyl group or halo $C_1$–$C_6$ alkylsulfonyl group), —C(=O)— or —C(=NOR$^6$)— (in this formula, R$^6$ represents hydrogen atom, $C_1$–$C_6$ alkyl group, halo $C_1$–$C_6$ alkyl group, $C_3$–$C_6$ alkenyl group, halo $C_3$–$C_6$ alkenyl group, $C_3$–$C_6$ alkynyl group, $C_3$–$C_6$ cycloalkyl group, phenyl $C_1$–$C_4$ alkyl group, or substituted phenyl $C_1$–$C_4$ alkyl group having, on the ring thereof, at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group), and R$^4$ represents hydrogen atom, $C_1$–$C_6$ alkyl group, halo $C_1$–$C_6$ alkyl group, $C_3$–$C_6$ alkenyl group, halo $C_3$–$C_6$ alkenyl group, $C_3$–$C_6$ alkynyl group, halo $C_3$–$C_6$ alkynyl group, $C_3$–$C_6$ cycloalkyl group, halo $C_3$–$C_6$ cycloalkyl group, $C_1$–$C_6$ alkoxy $C_1$–$C_6$ alkyl group, $C_1$–$C_6$ alkylthio $C_1$–$C_6$ alkyl group, formyl group, $C_1$–$C_6$ alkylcarbonyl group, halo $C_1$–$C_6$ alkylcarbonyl group, $C_1$–$C_6$ alkoxycarbonyl group, mono ($C_1$–$C_6$)alkylaminocarbonyl group, di($C_1$–$C_6$) alkylaminocarbonyl group in which the ($C_1$–$C_6$)alkyl groups may be same or different, mono($C_1$–$C_6$) alkylaminothiocarbonyl group, di($C_1$–$C_6$) alkylaminothiocarbonyl group in which the ($C_1$–$C_6$)alkyl groups may be same or different, di($C_1$–$C_6$) alkoxyphosphoryl group in which the ($C_1$–$C_6$)alkoxy groups may be same or different, di($C_1$–$C_6$)alkoxythiophosphoryl group in which the ($C_1$–$C_6$)alkoxy groups may be same or different, phenyl group, substituted phenyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, phenyl $C_1$–$C_4$ alkyl group, substituted phenyl ($C_1$–$C_4$)alkyl group having, on the ring thereof, at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group (the term heterocyclic group is as defined above), or substituted heterocyclic group (the term heterocyclic group is as defined above) having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group); and r represents an integer of 1 to 4); further, R$^1$ and R$^2$ may be taken conjointly with the N to which they are attached to form 4- to 7-membered rings which may be intercepted by 1 to 3, same or different oxygen atom, sulfur atom or nitrogen atom;

X, which may be same or different, represents halogen atom, cyano group, nitro group, $C_3$–$C_6$ cycloalkyl group, halo $C_3$–$C_6$ cycloalkyl group, phenyl group, substituted phenyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group (the term heterocyclic group is as defined above), substituted heterocyclic group (the term heterocyclic group is as defined above) having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, or —A$^2$—R$^7$ n represents an integer of 0 to 4; further, X may be taken conjointly with the adjacent carbon atom on the phenyl ring to form a fused ring (as used herein, the term fused ring means naphthalene, tetrahydronaphthalene, indene, indane, quinoline, quinazoline, chroman, isochroman, indole, indoline, benzodioxane, benzodioxole, benzofuran, dihydrobenzofuran, benzothiophene, dihydrobenzothiophene, benzoxazole, benzothiazole, benzimidazole or indazole), and said fused ring may have at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, phenyl group, substituted phenyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group (the term heterocyclic group is as defined above), and substituted heterocyclic group (the term heterocyclic group is as defined above) having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group;

Q is an optionally substituted, heterocyclic or fused heterocyclic group represented by one of the following formulas Q26 to Q28;

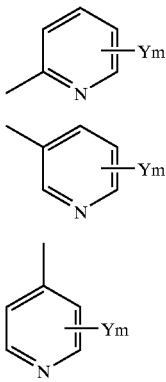

Q26

Q27

Q28

(in these formulas, Y, which may be same or different, represents halogen atom, cyano group, nitro group, halo $C_3$–$C_6$ cycloalkyl group, phenyl group, substituted phenyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group (the term heterocyclic group is as defined above), substituted heterocyclic group (the term heterocyclic group is as defined above) having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, or —$A^2$—$R^7$ (in this formula, $A^2$ and $R^7$ are as defined above); m represents an integer of 0 to 4;

alternatively, Y may be taken conjointly with adjacent carbon atom on the ring to form a fused ring (the fused ring is as defined above), and said fused ring may have at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, phenyl group, substituted phenyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group (the term heterocyclic group is as defined above), and substituted heterocyclic group (the term heterocyclic group is as defined above) having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group; and $Z^1$ and $Z^2$ represent oxygen atom or sulfur atom.

5. An agrihorticultural insecticide according to claim 4, wherein $R^1$, $R^2$ and $R^3$, which may be same or different, represent hydrogen atom, $C_3$–$C_6$ cycloalkyl group, halo $C_3$–$C_6$ cycloalkyl group or —$A^1$—$(G)_r$ (in this formula, $A^1$ represents $C_1$–$C_8$ alkylene group, $C_3$–$C_6$ alkenylene group or $C_3$–$C_6$ alkynylene group; G, which may be same or different, represents hydrogen atom, halogen atom, cyano group, nitro group, halo $C_1$–$C_6$ alkyl group, $C_3$–$C_6$ cycloalkyl group, halo $C_3$–$C_6$ cycloalkyl group, $C_1$–$C_6$ alkoxycarbonyl group, di($C_1$–$C_6$) alkoxyphosphoryl group in which the ($C_1$–$C_6$)alkoxy groups may be same or different, di($C_1$–$C_6$)alkoxythiophosphoryl group in which the ($C_1$–$C_6$)alkoxy groups may be same or different, diphenylphosphino group, diphenylphosphono group, phenyl group, substituted phenyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group (as used herein, the term "heterocyclic group" means pyridyl group, pyridine-N-oxide group, pyrimidinyl group, furyl group, tetrahydrofuryl group, thienyl group, tetrahydrothienyl group, tetrahydropyranyl group, oxazolyl group, isoxazolyl group, oxadiazolyl group, thiazolyl group, isothiazolyl group, thiadiazolyl group, imidazolyl group, triazolyl group or pyrazolyl group), substituted heterocyclic group (the term heterocyclic group is as defined above) having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, or —$Z^3$—$R^4$ (in this formula, $Z^3$ represents —O—, —S—, —SO—, —SO$_2$—, —N($R^5$)— (in this formula, $R^5$ represents hydrogen atom, $C_1$–$C_6$ alkylcarbonyl group, halo $C_1$–$C_6$ alkylcarbonyl group, $C_1$–$C_6$ alkoxycarbonyl group, phenylcarbonyl group, substituted phenylcarbonyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, phenyl $C_1$–$C_4$ alkoxycarbonyl group, substituted phenyl $C_1$–$C_4$ alkoxycarbonyl group having, on the ring thereof, at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, $C_1$–$C_6$ alkylsulfonyl group or halo $C_1$–$C_6$ alkylsulfonyl group), —C(=O)— or —C(=NOR$^6$)— (in this formula, $R^6$ represents hydrogen atom, $C_1$–$C_6$ alkyl group, halo $C_1$–$C_6$ alkyl group, $C_3$–$C_6$ alkenyl group, halo $C_3$–$C_6$ alkenyl group, $C_3$–$C_6$ alkynyl group, $C_3$–$C_6$ cycloalkyl group, phenyl $C_1$–$C_4$ alkyl group, or substituted phenyl $C_1$–$C_4$ alkyl group having, on the ring thereof, at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group), and $R^4$ represents hydrogen atom, $C_1$–$C_6$ alkyl group, halo $C_1$–$C_6$ alkyl group, $C_3$–$C_6$ alkenyl group, halo $C_3$–$C_6$ alkenyl group, $C_3$–$C_6$ alkynyl group, halo $C_3$–$C_6$ alkynyl group, $C_3$–$C_6$ cycloalkyl group, halo $C_3$–$C_6$ cycloalkyl group, $C_1$–$C_6$ alkoxy $C_1$–$C_6$ alkyl group, $C_1$–$C_6$ alkylthio $C_1$–$C_6$ alkyl group, formyl group, $C_1$–$C_6$ alkylcarbonyl group, halo $C_1$–$C_6$ alkylcarbonyl group, $C_1$–$C_6$ alkoxycarbonyl group, mono($C_1$–$C_6$)alkylaminocarbonyl group, di($C_1$–$C_6$)alkylaminocarbonyl group in which the ($C_1$–$C_6$)alkyl groups may be same or different, mono($C_1$–$C_6$)alkylaminothiocarbonyl group, di($C_1$–$C_6$)alkylaminothiocarbonyl group in which the ($C_1$–$C_6$)alkyl groups may be same or different, di($C_1$–$C_6$)alkoxyphosphoryl group in which the ($C_1$–$C_6$)alkoxy groups may be same or different, di($C_1$–$C_6$)alkoxythiophosphoryl group in which the ($C_1$–$C_6$)alkoxy groups may be same or different, phenyl group, substituted phenyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, phenyl $C_1$–$C_4$ alkyl group, substituted phenyl ($C_1$–$C_4$)alkyl group having, on the ring thereof, at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group (the term heterocyclic group is as defined above), or substituted heterocyclic group (the term heterocyclic group is as defined above) having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group); and r represents an integer of 1 to 4); further, $R^1$ and $R^2$ may be taken conjointly with the N to which they are attached to form 4- to 7-membered rings which may be intercepted by 1 to 3, same or different oxygen atom, sulfur atom or nitrogen atom;

X, which may be same or different, represents halogen atom, cyano group, nitro group, amino group, $C_1$–$C_6$ alkyl group, halo $C_1$–$C_6$ alkyl group, $C_3$–$C_6$ cycloalkyl group, halo $C_3$–$C_6$ cycloalkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, mono ($C_1$–$C_6$)alkylamino group, di($C_1$–$C_6$)alkylamino group in which the ($C_1$–$C_6$)alkyl groups may be same or different, $C_1$–$C_6$ alkylcarbonylamino group, halo $C_1$–$C_6$ alkylcarbonylamino group, $C_1$–$C_6$ alkoxycarbonyl group, or tri($C_1$–$C_6$ )alkylsilylethynyl group in which the ($C_1$–$C_6$)alkyl groups may be same or different; and n represents an integer of 0 to 4; further, X may be taken conjointly with the adjacent carbon atom on the phenyl ring to form a fused ring (as used herein, the term fused ring means naphthalene, tetrahydronaphthalene, indene, indane, quinoline, quinazoline, chroman, isochroman, indole, indoline, benzodioxane, benzodioxole, benzofuran, dihydrobenzofuran, benzothiophene, dihydrobenzothiophene, benzoxazole, benzothiazole, benzimidazole or indazole), and said fused ring may have at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, phenyl group, substituted phenyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group (the term heterocyclic group is as defined above), and substituted heterocyclic group (the term heterocyclic group is as defined above) having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group;

Q represents an optionally substituted, heterocyclic or fused heterocyclic group represented by one of the following formulas Q26, Q27, and Q28:

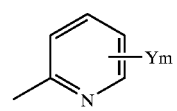

Q26

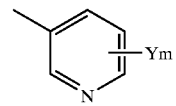

Q27

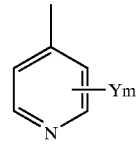

Q28

(in these formulas, Y, which may be same or different, represents halogen atom, cyano group, nitro group, $C_1$–$C_6$ alkyl group, halo $C_1$–$C_6$ alkyl group, halo $C_3$–$C_6$ cycloalkyl group, $C_1$–$C_6$ alkoxy group, halo $C_1$–$C_6$ alkoxy group, halo $C_1$–$C_6$ alkoxy halo $C_1$–$C_6$ alkoxy group, $C_1$–$C_6$ alkylthio group, halo $C_1$–$C_6$ alkylthio group, halo $C_1$–$C_6$ alkoxy halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, phenyl group, substituted phenyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, phenoxy group, substituted phenoxy group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group (the term heterocyclic group is as defined above), or substituted heterocyclic group (the term heterocyclic group is as defined above) having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group; and m represents an integer of 0 to 4;

alternatively, Y may be taken conjointly with adjacent carbon atom on the ring to form a fused ring (the fused ring is as defined above), and said fused ring may have at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group, halo $C_1$–$C_6$ alkylsulfonyl group, phenyl group, substituted phenyl group having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group, heterocyclic group (the term heterocyclic group is as defined above), and substituted heterocyclic group (the term heterocyclic group is as defined above) having at least one, same or different substituents selected from the group consisting of halogen atom, $C_1$–$C_6$ alkyl group, halo $C_1$–$C_6$ alkyl group, $C_1$–$C_6$ alkoxy group, halo $C_1$–$C_6$ alkoxy group, $C_1$–$C_6$ alkylthio group, halo $C_1$–$C_6$ alkylthio group, $C_1$–$C_6$ alkylsulfinyl group, halo $C_1$–$C_6$ alkylsulfinyl group, $C_1$–$C_6$ alkylsulfonyl group and halo $C_1$–$C_6$ alkylsulfonyl group; and $Z^1$ and $Z^2$ represent oxygen atom or sulfur atom.

6. A method for using an agrohorticultural insecticide characterized by treating an objective crop or applying to soil with an effective quantity of an agrohorticultural insecticide according to claim 3 for the purpose of controlling noxious organisms doing harm to useful crops.

* * * * *